US012655101B2

(12) United States Patent
Turner et al.

(10) Patent No.: US 12,655,101 B2
(45) Date of Patent: Jun. 16, 2026

(54) SMALL MOLECULES WITH ANTIBACTERIAL ACTIVITY

(71) Applicant: NEW MEXICO TECH UNIVERSITY RESEARCH PARK CORPORATION, Socorro, NM (US)

(72) Inventors: Danielle Nicole Turner, Roswell, NM (US); Liliya Frolova, Socorro, NM (US); Alexander Kornienko, San Marcos, TX (US); Snezna Rogelj, Socorro, NM (US)

(73) Assignee: NEW MEXICO TECH UNIVERSITY RESEARCH PARK CORPORATION, Socorro, NM (US)

( * ) Notice: Subject to any disclaimer, the term of this patent is extended or adjusted under 35 U.S.C. 154(b) by 318 days.

(21) Appl. No.: 18/347,446

(22) Filed: Jul. 5, 2023

(65) Prior Publication Data

US 2024/0010619 A1 Jan. 11, 2024

Related U.S. Application Data

(63) Continuation of application No. PCT/US2022/011428, filed on Jan. 6, 2022.

(60) Provisional application No. 63/134,471, filed on Jan. 6, 2021.

(51) Int. Cl.

| | |
|---|---|
| *C07D 209/10* | (2006.01) |
| *A61P 31/04* | (2006.01) |
| *C07D 209/36* | (2006.01) |
| *C07D 209/40* | (2006.01) |
| *C07D 231/56* | (2006.01) |
| *C07D 235/08* | (2006.01) |
| *C07D 333/58* | (2006.01) |
| *C07D 401/12* | (2006.01) |
| *C07D 403/12* | (2006.01) |
| *C07D 471/04* | (2006.01) |
| *C07D 487/04* | (2006.01) |

(52) U.S. Cl.

CPC ............ *C07D 209/10* (2013.01); *A61P 31/04* (2018.01); *C07D 209/36* (2013.01); *C07D 209/40* (2013.01); *C07D 231/56* (2013.01); *C07D 235/08* (2013.01); *C07D 333/58* (2013.01); *C07D 401/12* (2013.01); *C07D 403/12* (2013.01); *C07D 471/04* (2013.01); *C07D 487/04* (2013.01)

(58) Field of Classification Search

CPC .. C07D 209/10; C07D 209/36; C07D 209/40; C07D 231/56; C07D 235/08; C07D 307/81; C07D 333/58; C07D 401/12; C07D 403/12; C07D 471/04; C07D 487/04

See application file for complete search history.

(56) References Cited

PUBLICATIONS

Ge et al., CA 2007:1143370, 2007. (Year: 2007).*
Wang et al., CA 2007:148:308128, 2007. (Year: 2007).*
Tehrani et al., Iranian Journal of Pharmaceutical Research (2015), 14(4), 1077-1086. (Year: 2015).*
Galano et al., Theoretical Chemistry Accounts (2016), 135(6), 1-12. (Year: 2016).*
Chemical Abstracts Registry No. 301347-59-1, indexed in the Registry file on STN CAS Online Nov. 6, 2000. (Year: 2000).*
Chemical Abstracts Registry No. 26303-27-5, indexed in the Registry file on STN CAS Online Nov. 16, 1984. (Year: 1984).*

* cited by examiner

*Primary Examiner* — Laura L Stockton
(74) *Attorney, Agent, or Firm* — Neal, Gerber & Eisenberg LLP

(57) ABSTRACT

The present disclosure describes a method to treat conditions, including bacterial infections. The compounds of the disclosure can also interact synergistically with antibiotics used concomitantly to kill drug-resistant bacteria.

18 Claims, 43 Drawing Sheets

SMALL MOLECULES WITH ANTIBACTERIAL ACTIVITY

CROSS REFERENCE

This Application is a Continuation of PCT/US22/11428 filed Jan. 6, 2022, which claims the benefit of U.S. Provisional Application No. 63/134,471, filed Jan. 6, 2021, which is incorporated herein by reference in its entirety.

BACKGROUND

Antibiotics have become a mainstay of anti-microbial therapy, especially in treatment of bacterial infections. However, overuse of antibiotics has led to the emergence of drug-resistant bacteria due to antibiotic effectiveness and ease of access. The pathogenic bacteria that were initially sensitive to specific antibiotics are rapidly evolving to evade targeting by antibiotics. The development of a therapy that can combat the emergence of drug-resistant bacteria can assist in controlling the widespread evolution of pathogenic microbes.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, disclosed herein is a compound of formula:

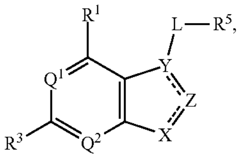

wherein:

- one ------ is a single bond and the other ------ is a double bond;
- X is O, S, N, NH, or $N(R^N)$;
- $R^N$ is alkyl, alkylene, acyl, or alkoxycarbonyl, any of which is substituted or unsubstituted;
- Z is CH, C(alkyl that is substituted or unsubstituted), C(aryl that is substituted or unsubstituted), C(heteroaryl that is substituted or unsubstituted), or N;
- Y is C or N, wherein when Y is N, the ------ connecting Y and Z is the single bond, and X is N, and wherein when Y is C, the ------ connecting Y and Z is the double bond, and X is O, S, NH, or $N(R^N)$;
- L is —CH═N—NH—, —N═N—, or —CH═N—$NHSO_2$—;
- $Q^1$ is N or $CR^2$;
- $Q^2$ is N or $CR^4$;
- $R^1$ is OH, $OR^{1a}$, SH, $SR^{1a}$, $NH_2$, $NHR^{1a}$, $N(R^{1a})_2$, $N(R^{1a})_3$, $OC(O)NH_2$, $OC(O)NHR^{1a}$, $OC(O)N(R^{1a})_2$, $NHC(NH)NH_2$, $NHC(NH)NHR^{1a}$, $NHC(NH)N(R^a)_2$, $NHC(O)NH_2$, $NHC(O)NHR^{1a}$, $NHC(O)N(R^{1a})_2$, or H;
- each $R^{1a}$ is independently $C(O)R^{1b}$, alkyl, alkenyl, alkynyl, aryl, cycloalkyl, heterocyclyl, heteroaryl, or an amino acid residue, any of which is substituted or unsubstituted;
- $R^{1b}$ is alkyl, alkenyl, alkynyl, aryl, cycloalkyl, heterocyclyl, or heteroaryl, any of which is substituted or unsubstituted;
- $R^2$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;
- $R^3$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;
- $R^4$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;
- $R^5$ is aryl, cycloalkyl, heterocyclyl, heteroaryl, or $C(O)R^6$, any of which is substituted or unsubstituted; and
- $R^6$ is alkyl, alkenyl, alkynyl, aryl, cycloalkyl, heterocyclyl, or heteroaryl, any of which is substituted or unsubstituted, or a pharmaceutically-acceptable salt thereof.

In some embodiments, disclosed herein is a method of treating a condition, the method comprising administering to a subject in need thereof a therapeutically-effective amount of a compound of formula:

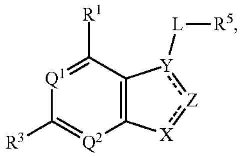

wherein:

- one ------ is a single bond and the other ------ is a double bond;
- X is O, S, N, NH, or $N(R^N)$;
- $R^N$ is alkyl, alkylene, acyl, or alkoxycarbonyl, any of which is substituted or unsubstituted;
- Z is CH, C(alkyl that is substituted or unsubstituted), C(aryl that is substituted or unsubstituted), C(heteroaryl that is substituted or unsubstituted), or N;
- Y is C or N, wherein when Y is N, the ------ connecting Y and Z is the single bond, and X is N, and wherein when Y is C, the ------ connecting Y and Z is the double bond, and X is O, S, NH, or $N(R^N)$;
- L is a linker group;
- $Q^1$ is N or $CR^2$;
- $Q^2$ is N or $CR^4$;
- $R^1$ is OH, $OR^{1a}$, SH, $SR^{1a}$, $NH_2$, $NHR^{1a}$, $N(R^{1a})_2$, $N(R^{1a})_3$, $OC(O)NH_2$, $OC(O)NHR^{1a}$, $OC(O)N(R^{1a})_2$, $NHC(NH)NH_2$, $NHC(NH)NHR^{1a}$, $NHC(NH)N(R^{1a})_2$, $NHC(O)NH_2$, $NHC(O)NHR^{1a}$, $NHC(O)N(R^{1a})_2$, or H;
- each $R^{1a}$ is independently $C(O)R^{1b}$, alkyl, alkenyl, alkynyl, aryl, cycloalkyl, heterocyclyl, heteroaryl, or an amino acid residue, any of which is substituted or unsubstituted;
- $R^{1b}$ is alkyl, alkenyl, alkynyl, aryl, cycloalkyl, heterocyclyl, or heteroaryl, any of which is substituted or unsubstituted;
- $R^2$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;
- $R^3$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;

$R^4$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;

$R^5$ is aryl, cycloalkyl, heterocyclyl, heteroaryl, or $C(O)R^6$, any of which is substituted or unsubstituted; and $R^6$ is alkyl, alkenyl, alkynyl, aryl, cycloalkyl, heterocyclyl, or heteroaryl, any of which is substituted or unsubstituted, or a pharmaceutically-acceptable salt thereof.

BRIEF DESCRIPTION OF THE FIGURES

FIGS. 26A-1 to 26A-5 show IC50 toxicity of Compound 25 (FIG. 26A-1), Compound 26 (FIG. 26A-2), Compound 27 (FIG. 26A-3), Compound 14 (FIG. 26A-4), and Compound 15 (FIG. 26A-5) on HeLa cells in 10% FBS. FIGS. 26B-1 to 26B-5 show IC50 toxicity of Compound 25 (FIG. 26B-1), Compound 26 (FIG. 26B-2), Compound 27 (FIG. 26B-3), Compound 14 (FIG. 26B-4), and Compound 15 (FIG. 26B-5) on HeLa cells in 40% FBS.

FIGS. 30F-301 show filamentation with ciprofloxacin and Compound 25 on *E. coli.*

DETAILED DESCRIPTION

Figure 1:
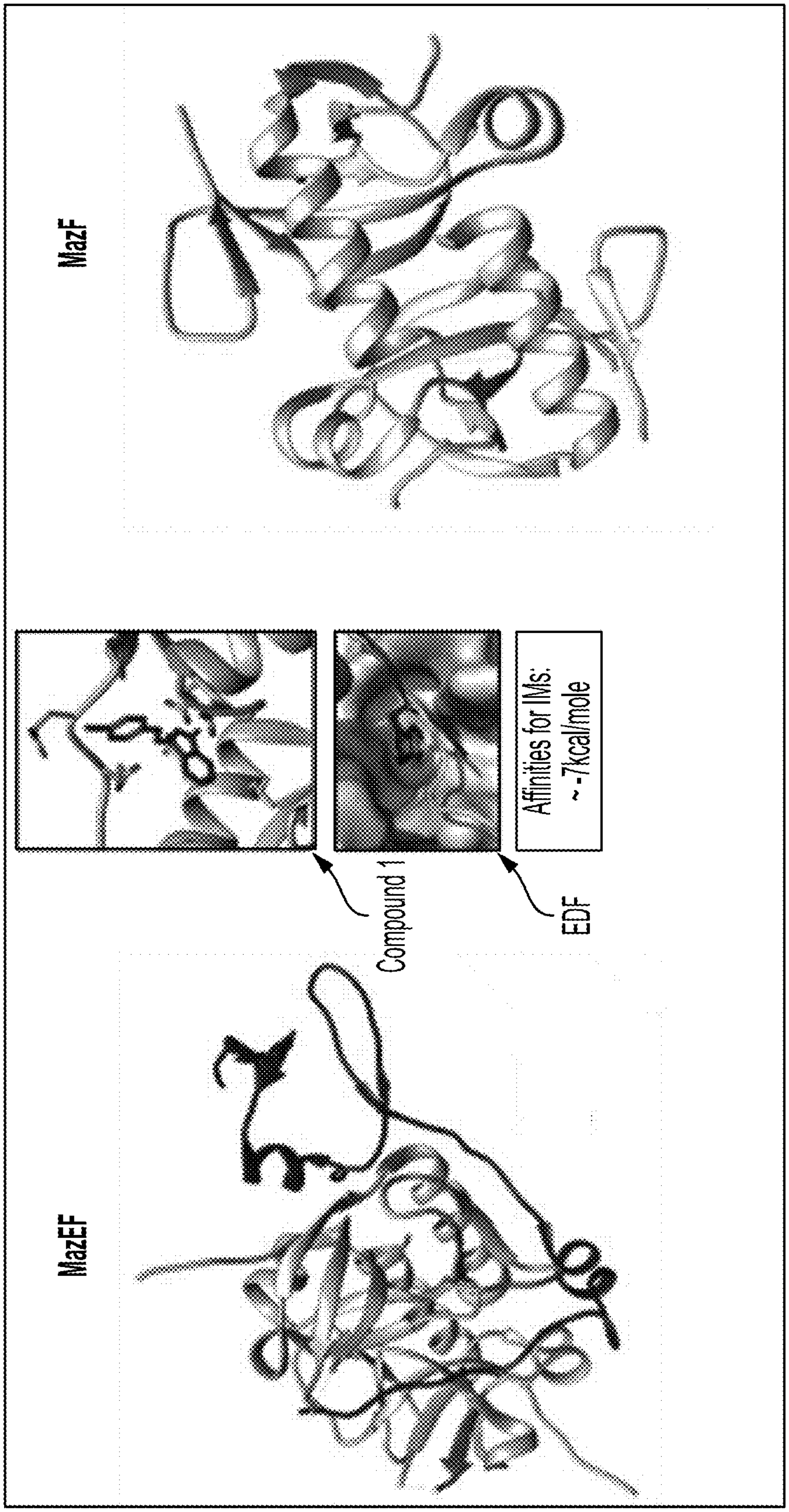
FIG. 1 shows docking images of a compound of the disclosure and EDF with MazEF and MazF.

Antibiotics.

Antibiotics are used globally as therapy in the treatment of, for example, bacterial infections. Antibiotics can also be effective against some fungi and protozoa. Antibiotics can be classified as bacteriostatic, wherein the antibiotic inhibits reproduction of the bacteria, and bactericidal, wherein the antibiotic kills the bacteria. Antibiotics can be further classified by mechanism of action, which can include, for example, inhibition of bacterial cell wall synthesis, inhibition of bacterial cell membrane synthesis, inhibition of essential bacterial enzymes, inhibition of cell division, inhibition of peptidoglycan synthesis, inhibition of protein synthesis via binding to a 30S or 50S subunit of bacterial ribosome, inhibition of isoprenyl pyrophosphate, inhibition of folate synthesis, and production of toxic free radicals.

Antibiotics can be used to treat bacterial infections. Antibiotics can also be used prophylactically for a subject, for example, having a wound that is likely to become infected, a subject about to undergo surgery, a subject about to receive dental treatment, or a subject who suffers from recurring infections including, for example, cellulitis, urinary tract infections, and rheumatic fever.

Overuse of antibiotics in the healthcare and agricultural industries, and misuse of antibiotics, including use of antibiotics in the treatment of viral infections, cessation of antibiotic therapy prior to end of prescribed period, and prophylactic use of antibiotics by travelers, has led to the emergence of drug-resistant bacteria. Mutations that can help bacteria survive treatment with an antibiotic can quickly become prevalent throughout a bacterial population, and genetic elements encoding resistance mechanisms can be transferred between bacterial species.

Mechanisms of Bacterial Resistance to Antibiotics.

Bacteria can use various mechanisms to avoid killing by an antibiotic. Bacteria can, for example, modify the protein targeted by the antibiotic, enzymatically inactivate the antibiotic, decrease the ability of the antibiotic to enter the cell, transfer resistance genes between organisms via conjugation, transduction, or transformation, or increase the exit of the antibiotic from the cell using efflux pumps. In some embodiments, the compounds disclosed herein can affect bacterial growth by modulating the MazEF pathway. In some embodiments, the compounds disclosed herein can affect bacterial growth by modulating the RecA/LexA pathway. In some embodiments, the compounds disclosed herein can affect bacterial growth by modulating the MazEF pathway and the RecA/LexA pathway.

MazEF pathway: A toxin-antitoxin (TA) system is a set of two or more bacterial genes that together encode both a protein "poison" and a corresponding "antidote." Bacterial TA systems consist of a toxin and an antitoxin protein. When expressed, the toxin kills the bacterium. However, under normal circumstances, the antitoxin binds to the toxin and neutralizes the toxin, thereby preventing bacterial death. When the antitoxin is degraded or not functional, the toxin produced kills the bacterium. This pathway is known as programmed cell death (PCD).

The MazEF TA system, one of the widely distributed TA systems, is implicated in PCD of *Escherichia coli* and other pathogens. Nutrient starvation, antibiotic stress, heat shock, DNA damage, and other kinds of stressors can elicit MazEF-mediated-PCD. These stressful conditions can prevent the expression of MazE (antitoxin), leading to a reduction in MazE and thereby permitting MazF (toxin) to exert its toxic effect. If a cell produces MazF in response to stress, MazF must be deactivated by binding to MazE to prevent the death cascade. In some embodiments, the compounds of the disclosure can inhibit the binding of MazE to MazF by mimicking extracellular death factor (EDF).

Under stress, antitoxin MazE is destroyed by ClpAP protease, and the more stable MazF toxin causes cell death. Activity of stress-induced ClpXP protease leads to the formation of EDF peptide, which is a Quorum Sensing factor that inhibits the formation of the MazEF complex. EDF can amplify the in vitro endoribonucleolytic activity of MazF in *E. coli* and overcome the in vitro inhibitory effect of the antitoxin MazE on the MazF toxin. EDF peptide is a linear pentapeptide containing a central tryptophan (W) residue. This residue is conserved across a broad spectrum of bacterial genera, including Mycobacteria.

In some embodiments, compounds of the disclosure can mimic the central tryptophan of EDF. In some embodiments, the compounds of the disclosure can interfere with MazEF partners binding to each other, allowing PCD to proceed in the same manner as is induced by EDF.

RecA/LexA stress response and apoptosis-like death: Inhibition of the RecA/LexA stress response can lead to blockage of evolution of resistance to compounds of the disclosure, and under extreme stress, apoptosis-like death (ALD). In some embodiments, compounds of the disclosure can affect bacterial growth by modulating the RecA/LexA pathway.

The SOS response is a widely conserved DNA damage repair network that allows bacteria to survive severe DNA damage at the cost of elevated mutagenesis but with the potential benefit of acquired resistance to genotoxic stressors. The transcription-requiring process repairs DNA lesions through mutagenic DNA polymerization and repair. Under normal circumstances, the LexA protein negatively regulates expression of the SOS response. When DNA-lesion-dependent RecA inactivates this LexA repressor, transcription of the SOS gene products takes place. Among these products is an error-prone DNA polymerase V encoded by UmuC and UmuD genes, and a RecA protein. Genetic integrity is sacrificed for cell survival. However, when expression of the error-prone polymerase or the additional RecA is blocked or overwhelmed, the SOS response leads to apoptosis-like cell death. In some embodiments, the compounds of the disclosure can interfere with the RecA/LexA-mediated bacterial SOS response and trigger apoptosis-like death.

Compounds of the Invention.

Disclosed herein are compounds that can kill bacteria. In some embodiments, the compounds of the disclosure can kill Gram-negative bacteria. In some embodiments, the compounds of the disclosure can kill gram-negative bacteria at low micromolar concentrations. In some embodiments, the compounds of the disclosure are not susceptible to bacterial evolution of resistance. In some embodiments, the compounds of the disclosure can selectively kill bacteria in a co-culture with human cells. In some embodiments, the compounds of the disclosure are active in the presence of serum. In some embodiments, the compounds of the disclosure do not work by permeabilizing bacterial membranes. In some embodiments, the compounds of the disclosure do not cause significant hemolysis at relevant concentrations. In some embodiments, the compounds of the disclosure can rapidly dissipate bacterial membrane potential. In some embodiments, the compounds of the disclosure can synergize with clinically used antibiotics to increase the efficacy of the compounds.

Disclosed herein is a compound of formula:

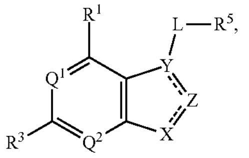

wherein:

one ------ is a single bond and the other ------ is a double bond;

X is O, S, N, NH, or $N(R^N)$;

$R^N$ is alkyl, alkylene, acyl, or alkoxycarbonyl, any of which is substituted or unsubstituted;

Z is CH, C(alkyl that is substituted or unsubstituted), C(aryl that is substituted or unsubstituted), C(heteroaryl that is substituted or unsubstituted), or N;

Y is C or N, wherein when Y is N, the ------ connecting Y and Z is the single bond, and X is N, and wherein when Y is C, the ------ connecting Y and Z is the double bond, and X is O, S, NH, or $N(R^N)$;

L is —$C_{1-6}$alkylene-CH═N—NH—, —N═N—, or —CH═N—$NHSO_2$—, wherein the —$C_{1-6}$alkylene is substituted or unsubstituted;

$Q^1$ is N or $CR^2$;

$Q^2$ is N or $CR^4$;

$R^1$ is OH, $OR^{1a}$, SH, $SR^{1a}$, $NH_2$, $NHR^{1a}$, $N(R^{1a})_2$, $N(R^{1a})_3$, $OC(O)NH_2$, $OC(O)NHR^{1a}$, $OC(O)N(R^{1a})_2$, $NHC(NH)NH_2$, $NHC(NH)NHR^{1a}$, $NHC(NH)N(R^{1a})_2$, $NHC(O)NH_2$, $NHC(O)NHR^{1a}$, $NHC(O)N(R^{1a})_2$, or H;

each $R^{1a}$ is independently $C(O)R^{1b}$, alkyl, alkenyl, alkynyl, aryl, cycloalkyl, heterocyclyl, heteroaryl, or an amino acid residue, any of which is substituted or unsubstituted;

$R^{1b}$ is alkyl, alkenyl, alkynyl, aryl, cycloalkyl, heterocyclyl, or heteroaryl, any of which is substituted or unsubstituted;

$R^2$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;

$R^3$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;

$R^4$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;

$R^5$ is aryl, cycloalkyl, heterocyclyl, heteroaryl, or $C(O)R^6$, any of which is substituted or unsubstituted; and $R^6$ is alkyl, alkenyl, alkynyl, aryl, cycloalkyl, heterocyclyl, or heteroaryl, any of which is substituted or unsubstituted, or a pharmaceutically-acceptable salt thereof.

Disclosed herein is a compound of formula:

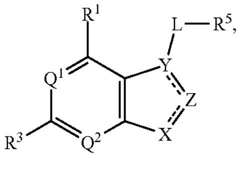

wherein:

one ------ is a single bond and the other ------ is a double bond;

X is O, S, N, NH, or $N(R^N)$;

$R^N$ is alkyl, alkylene, acyl, or alkoxycarbonyl, any of which is substituted or unsubstituted;

Z is CH, C(alkyl that is substituted or unsubstituted), C(aryl that is substituted or unsubstituted), C(heteroaryl that is substituted or unsubstituted), or N;

Y is C or N, wherein when Y is N, the ------ connecting Y and Z is the single bond, and X is N, and wherein when Y is C, the ------ connecting Y and Z is the double bond, and X is O, S, NH, or $N(R^N)$;

L is —CH═N—NH—, —N═N—, or —CH═N—$NHSO_2$—;

$Q^1$ is N or $CR^2$;

$Q^2$ is N or $CR^4$;

$R^1$ is OH, $OR^{1a}$, SH, $SR^{1a}$, $NH_2$, $NHR^{1a}$, $N(R^{1a})_2$, $N(R^{1a})_3$, $OC(O)NH_2$, $OC(O)NHR^{1a}$, $OC(O)N(R^{1a})_2$, $NHC(NH)NH_2$, $NHC(NH)NHR^{1a}$, $NHC(NH)N(R^{1a})_2$, $NHC(O)NH_2$, $NHC(O)NHR^{1a}$, $NHC(O)N(R^{1a})_2$, or H;

each $R^{1a}$ is independently $C(O)R^{1b}$, alkyl, alkenyl, alkynyl, aryl, cycloalkyl, heterocyclyl, heteroaryl, or an amino acid residue, any of which is substituted or unsubstituted;

$R^{1b}$ is alkyl, alkenyl, alkynyl, aryl, cycloalkyl, heterocyclyl, or heteroaryl, any of which is substituted or unsubstituted;

$R^2$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;

$R^3$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;

$R^4$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;

$R^5$ is aryl, cycloalkyl, heterocyclyl, heteroaryl, or $C(O)R^6$, any of which is substituted or unsubstituted; and $R^6$ is alkyl, alkenyl, alkynyl, aryl, cycloalkyl, heterocyclyl, or heteroaryl, any of which is substituted or unsubstituted, or a pharmaceutically-acceptable salt thereof In some embodiments, disclosed herein is a compound of the formula:

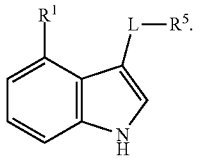

In some embodiments, disclosed herein is a compound of the formula:

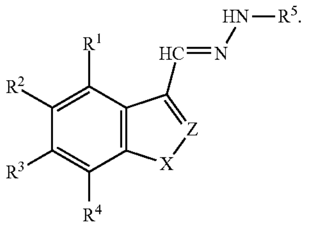

In some embodiments, disclosed herein is a compound of the formula:

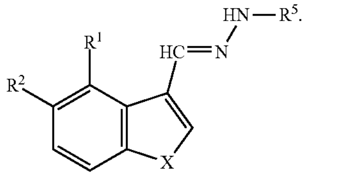

In some embodiments, disclosed herein is a compound of the formula:

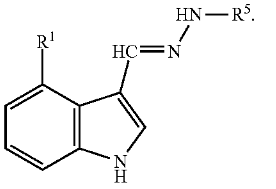

In some embodiments, $R^2$ is H.

In some embodiments, L is —CH═N—NH—. In some embodiments, L is —$C_{1-6}$alkylene-CH═N—NH— that is substituted or unsubstituted. In some embodiments, L is —$CH_2$—CH═N—NH—. In some embodiments, L is —$CH_2CH_2$—CH═N—NH—.

In some embodiments, $R^1$ is OH, $OR^{1a}$, $NH_2$, $NHR^{1a}$, or $N(R^{1a})_2$. In some embodiments, $R^1$ is OH, $NH_2$, $NMe_3$; NH(1H-benzotriazol-1-yl; $NHC(O)CH(NH_2)CH_2C(O)NH_2$, $NHC(O)CH(NH_2)(CH_2)_3NHC(NH)NH_2$, $OC(O)(CH_2)_3Me$, $OC(O)CH(NH_2)(CH_2)_3NHC(NH)NH_2$, $OC(O)CH(NHC(O)OCMe_3)(CH_2)_3NHC(NH)NH_2$, $NHC(O)OCMe_3$, O-benzyl, $OC(O)(CH_2)_3NH_2$, $O(CH_2)_4NMe_3$, 2-(4-methylpipyrazin-1-yl)-ethoxy, 2-(1-methylpipyradin-4-yl)-ethoxy, or 2-(1,1-dimethylpipyradin-4-yl)-ethoxy. $R^1$ is $OR^{1a}$, and $R^{1a}$ is alkyl that is substituted. In some embodiments, $R^1$ is $OR^{1a}$, and $R^{1a}$ is alkyl that is substituted with aryl, heteroaryl, or amino. In some embodiments, $R^1$ is O-benzyl.

In some embodiments, $R^5$ is phenyl, substituted phenyl, C(O)(substituted alkyl), pyrimidinyl, substituted naphthalene, tetrahydropyrimidine, substituted methyl, substituted quinoline, or C(O)phenyl. In some embodiments, $R^5$ is 4-substituted phenyl, 2,4-disubstituted phenyl, C(O)(substituted methyl), 2-pyrimidinyl, 5-substituted naphthalene, 2-tetrahydropyrimidine, trisubstituted methyl, 7-substituted quinoline-4-yl, or C(O)phenyl. In some embodiments, $R^5$ is bromophenyl, chlorophenyl, dichlorophenyl, fluorophenyl, nitrophenyl, benzoic acid, C(O)(cyanoalkyl), 2-pyrimidinyl, benzonitrile, anisole, aminonaphthalene, 3,4,5,6-tetrahydropyrimidine, fluoromethyl, aniline, bromoquinoline, or —C(O)phenyl. In some embodiments, $R^5$ is 4-bromophenyl, 2-chlorophenyl, 4-chlorophenyl, 4-fluorophenyl, 4-nitrophenyl, 4-benzoic acid, C(O)(cyanomethyl), 2-pyrimidinyl, 4-benzonitrile, 4-anisole, 2,4-dichlorophenyl, 5-aminonaphthalene, 2-(3,4,5,6-tetrahydropyrimidine), trifluoromethyl, 4-aniline, 7-bromoquinolin-4-yl, or C(O)phenyl. In some embodiments, In some embodiments, $R^5$ is substituted aryl. In some embodiments, $R^5$ is substituted phenyl. In some embodiments, $R^5$ is 4-substituted phenyl. In some embodiments, $R^5$ is 4-bromophenyl. In some embodiments, $R^5$ is 4-chlorophenyl.

In some embodiments, the compound is:

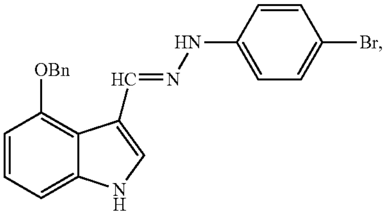 [SMILES: Brc1ccc(N/N=C/c2c[nH]c3cccc(OCc4ccccc4)c23)cc1]

or a pharmaceutically-acceptable salt thereof.

In some embodiments, the compound is:

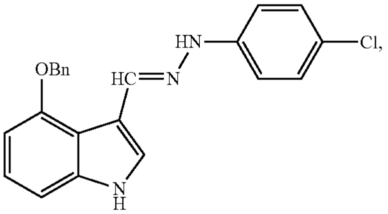 [SMILES: Clc1ccc(N/N=C/c2c[nH]c3cccc(OCc4ccccc4)c23)cc1]

or a pharmaceutically-acceptable salt thereof.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, and ester groups.

Non-limiting examples of alkyl and alkylene groups include straight, branched, and cyclic alkyl and alkylene groups. An alkyl or alkylene group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of cyclic alkyl groups include cyclopropyl, cyclobutyl, cyclopentyl, cyclohexyl, cycloheptlyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl.

An aryloxy group can be, for example, an oxygen atom substituted with any aryl group, such as phenoxy.

An aralkyl group can be, for example, any alkyl group substituted with any aryl group, such as benzyl.

An arylalkoxy group can be, for example, an oxygen atom substituted with any aralkyl group, such as benzyloxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group. A non-limiting example of an acyloxy group, or an ester group, is acetate.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

In some embodiments, disclosed herein is a compound of the formula:

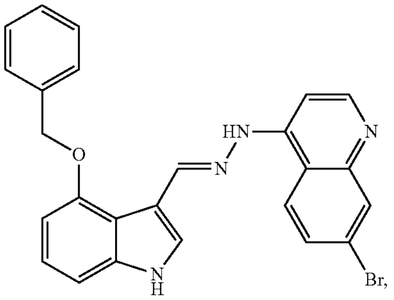
,
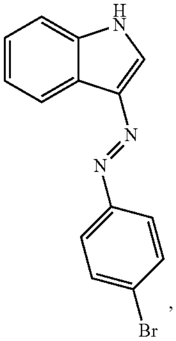
,
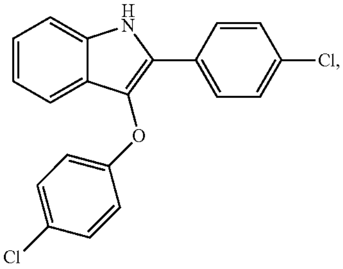
,
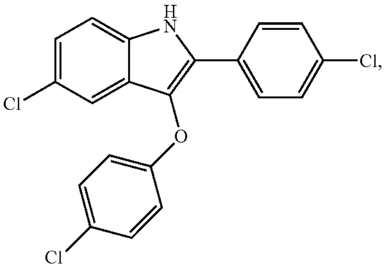
,
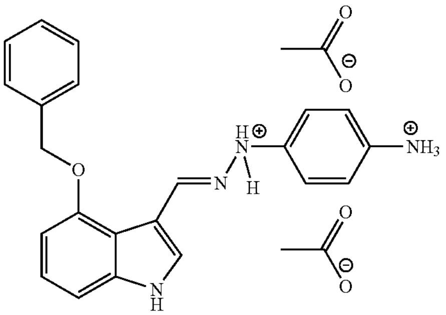

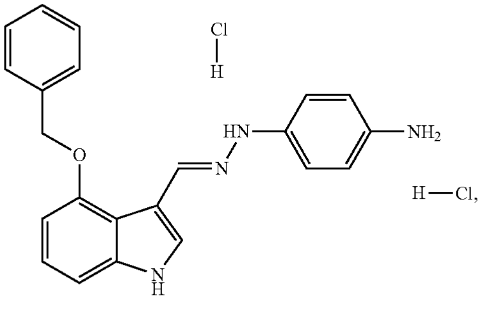
,

-continued
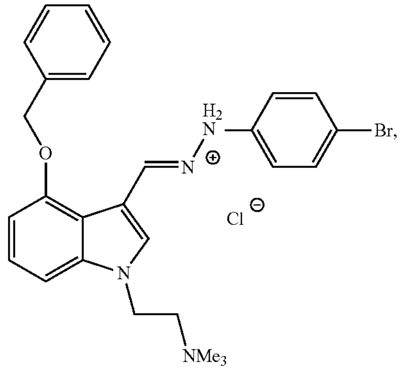
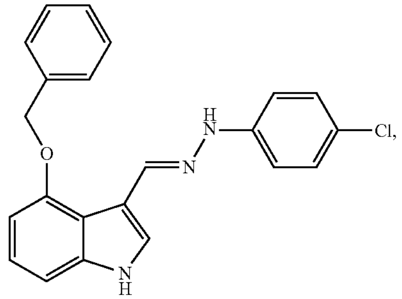
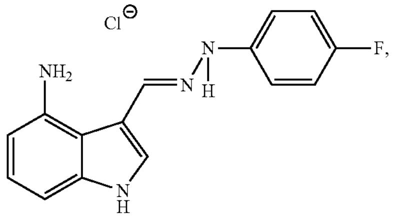
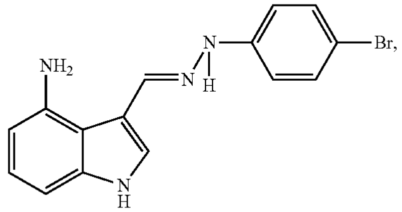
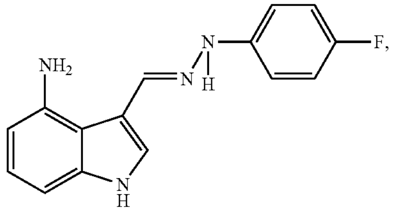
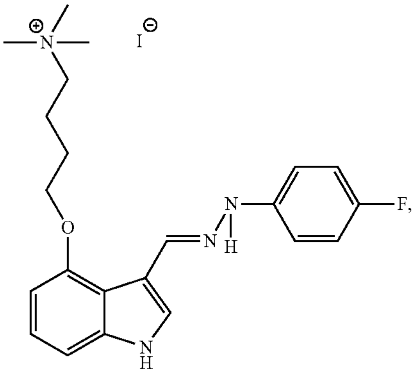
-continued
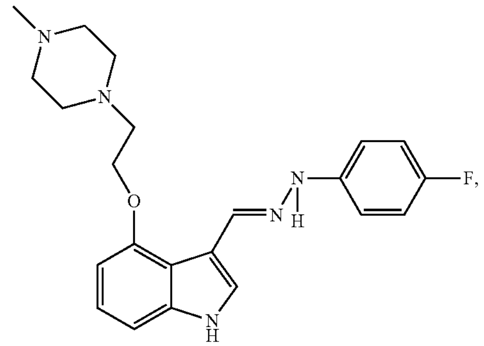
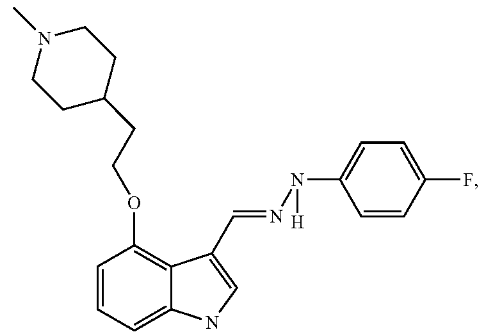
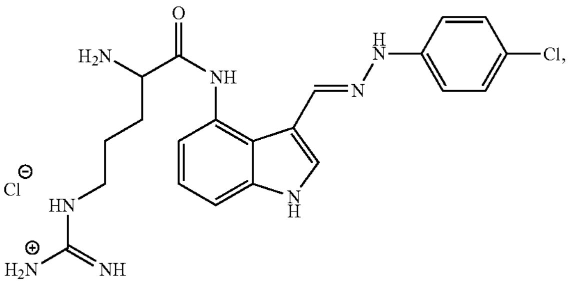
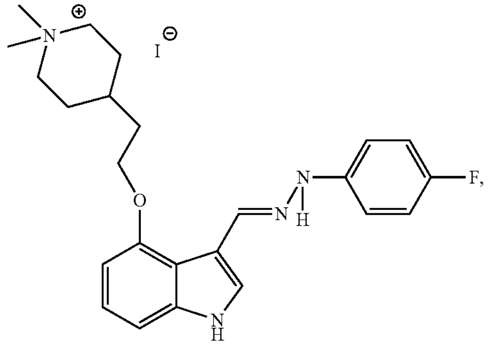
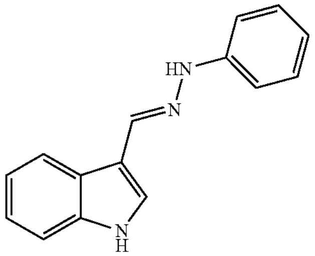
, -continued
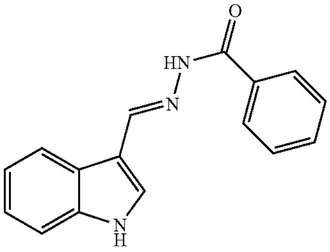
,
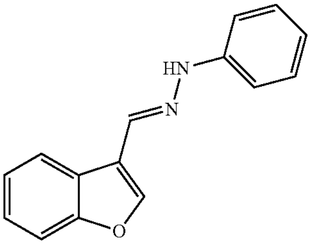
,
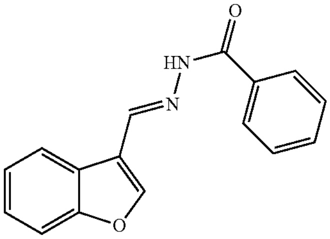
,
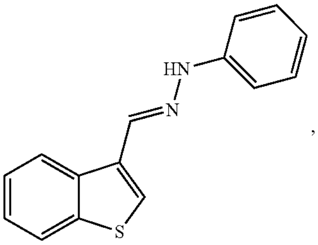
,
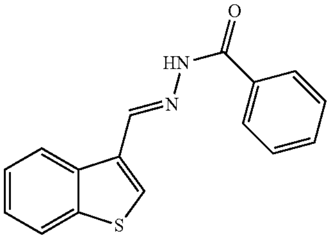
,
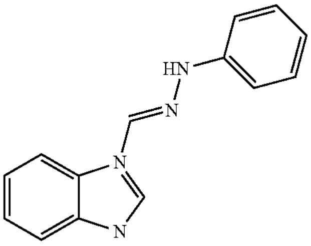
,
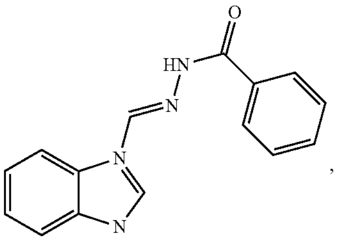
,
-continued
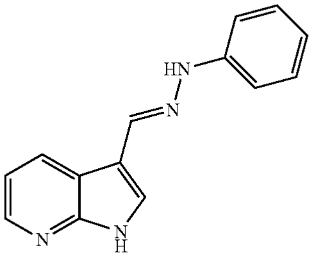
,
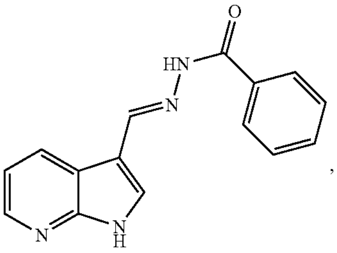
,
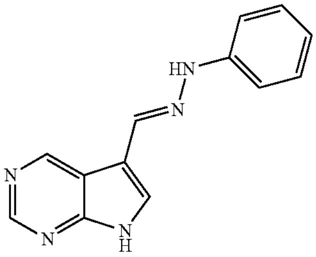
,
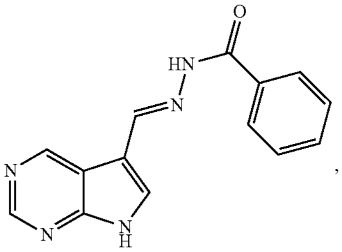
,
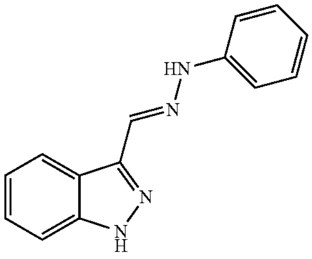
,
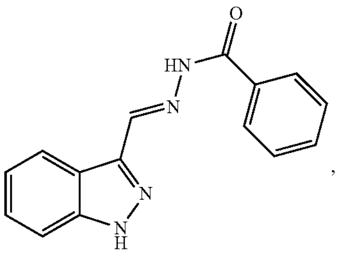
, -continued
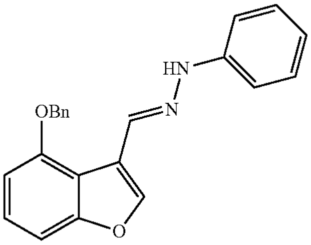
,
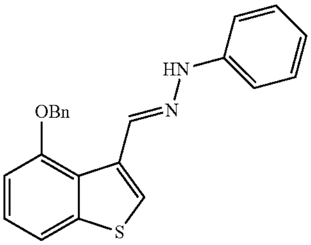
,
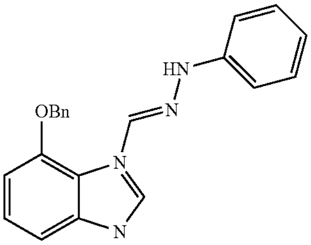
,
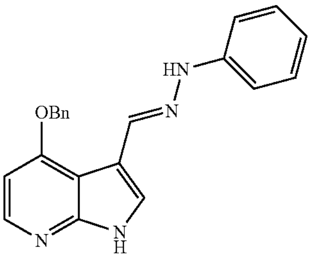
,
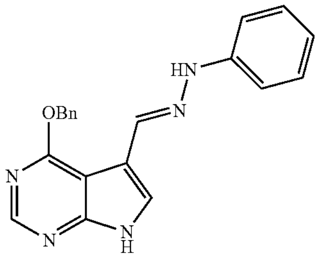
,
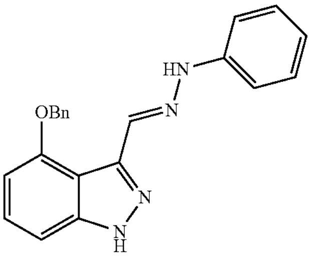
,
-continued
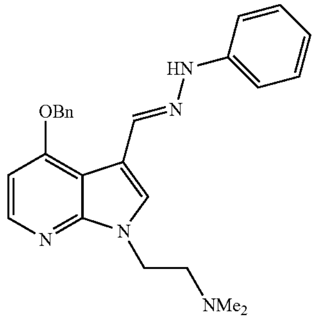
,
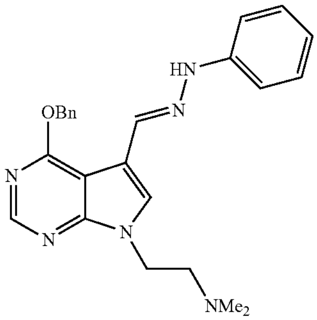
,
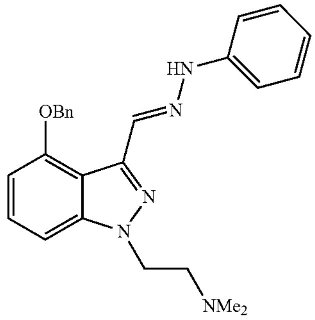
,
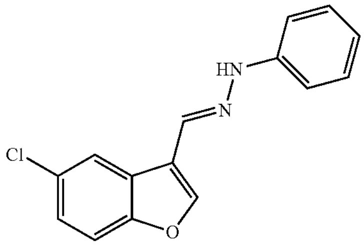
,
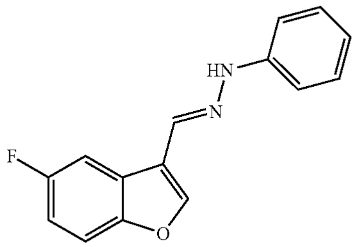
,
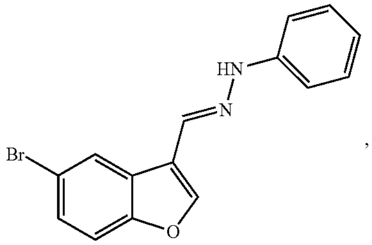
, -continued
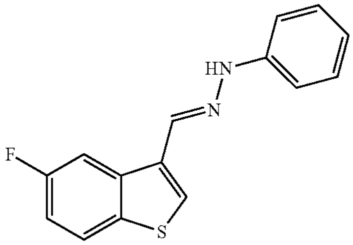
,
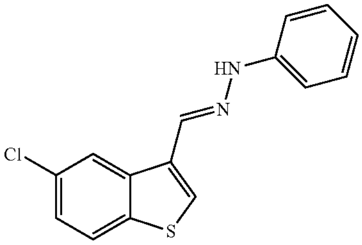
,
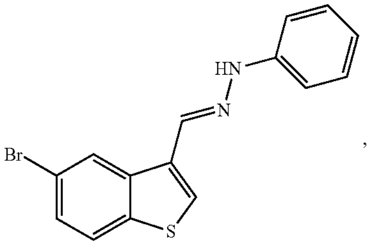
,
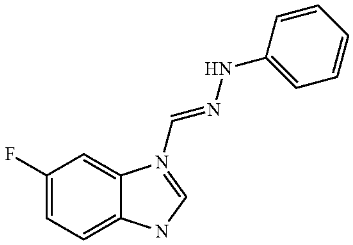
,
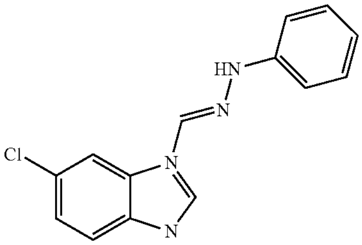
,
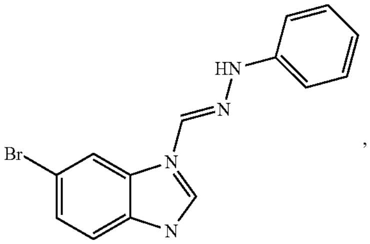
,
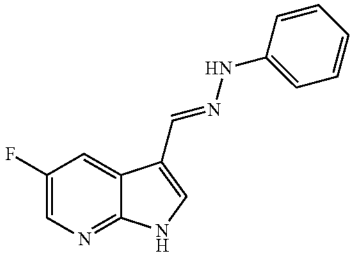
,
-continued
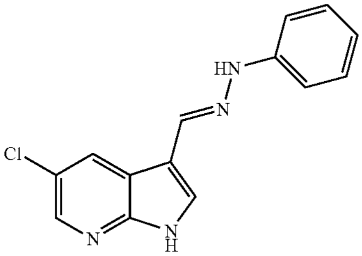
,
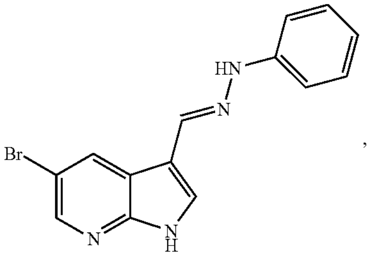
,
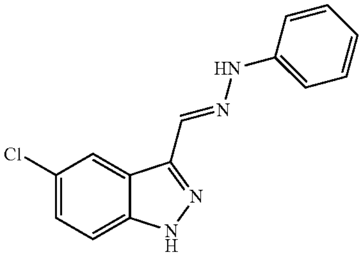
,
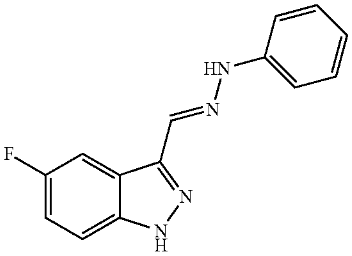
,
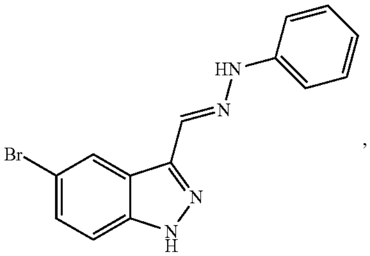
,
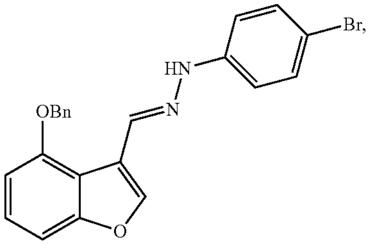

-continued
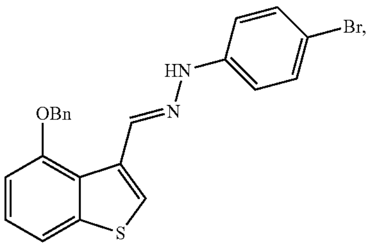
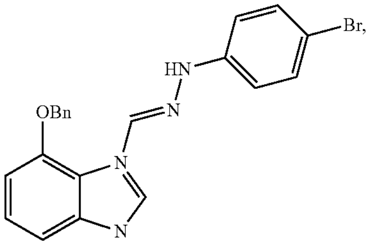
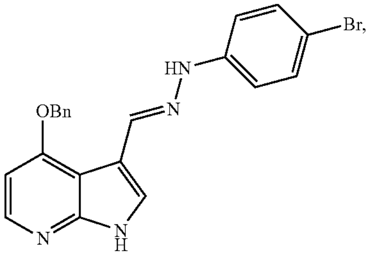
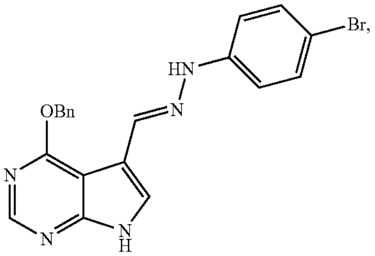
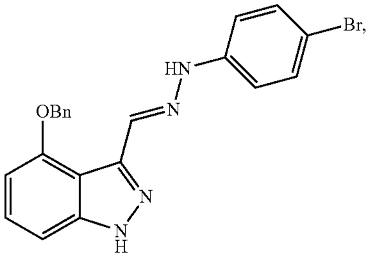
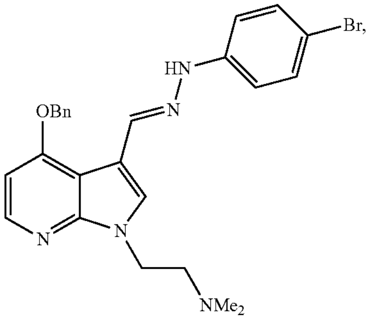
-continued
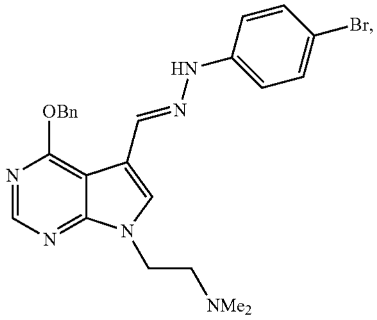
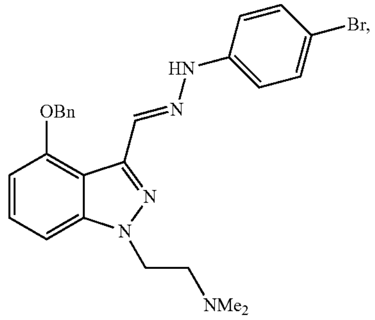
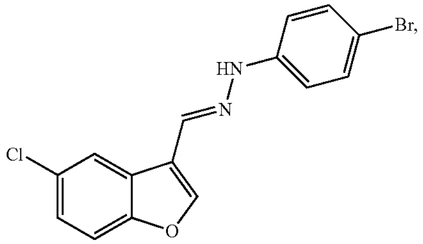
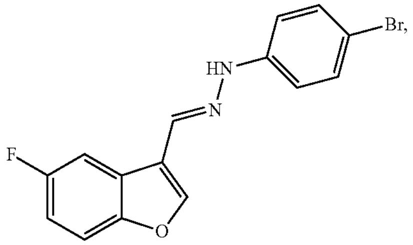
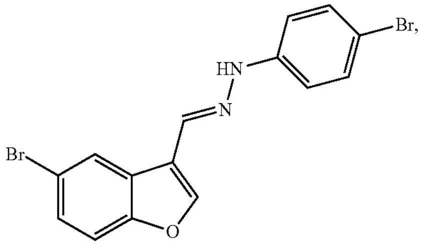
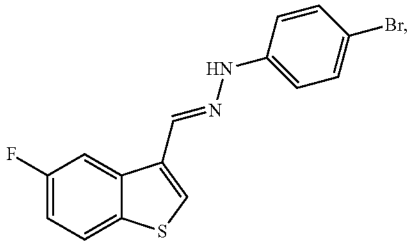

-continued

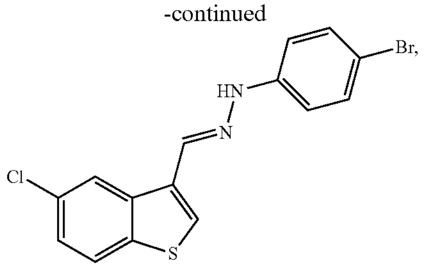

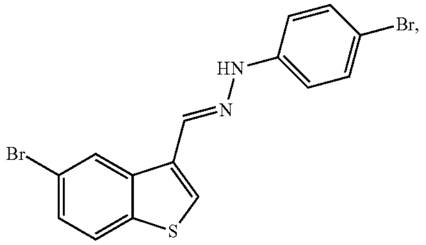

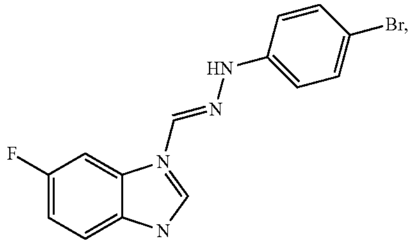

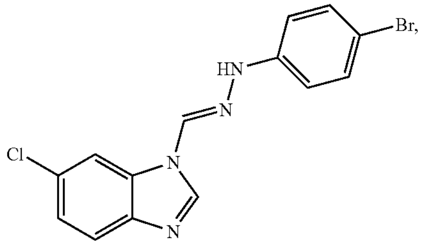

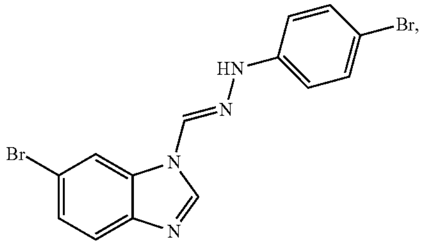

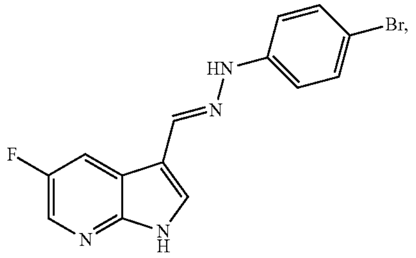

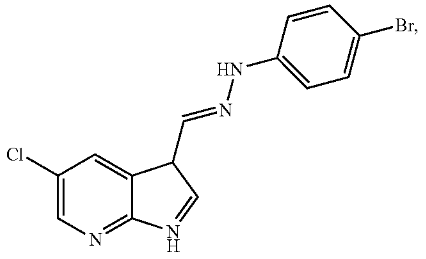

-continued

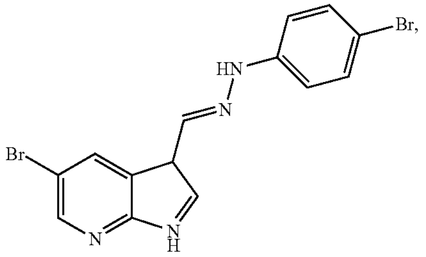

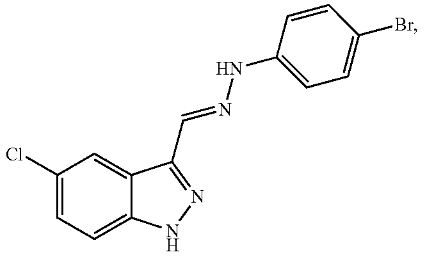

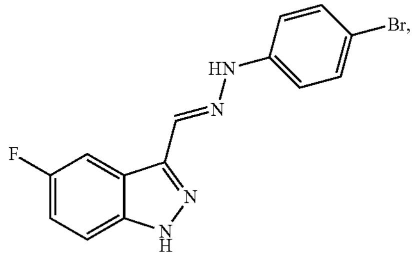

or

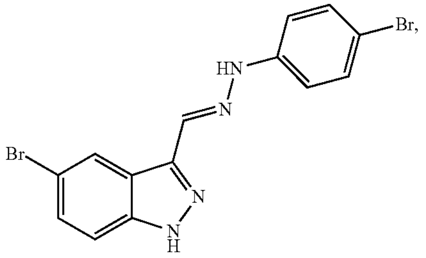

or a pharmaceutically-acceptable salt thereof.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Pharmaceutically-Acceptable Salts.

The invention provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

METHODS OF USE

Disclosed herein is a method of treating a condition, the method comprising administering to a subject in need thereof a therapeutically-effective amount of a compound of the disclosure. In some embodiments, the condition is caused by a microbe. In some embodiments, the microbe can be a bacterium, fungus, or protozoa. In some embodiments, the microbe is a bacterium. In some embodiments, the microbe is a gram-positive bacterium. In some embodiments, the microbe is a gram-negative bacterium. In some embodiments, the microbe is a drug-resistant or drug-sensitive bacterium. Non-limiting examples of microbes that can be treated by a method of the invention include *Acinetobacter baumannii*, carbapenem-resistant Enterobacteriaceae (CRE), clindamycin-resistant Group B *Streptococcus, Clostridium difficile*, drug-resistant *Campylobacter*, drug-resistant *Neisseria gonorrhoeae*, drug-resistant non-typhoidal *Salmonella*, drug-resistant *Salmonella Typhi*, drug-resistant *Shigella*, drug-resistant *Streptococcus pneumoniae*, drug-resistant tuberculosis, erythromycin-resistant Group A *Streptococcus, Escherichia coli*, extended spectrum β-lactamase producing Enterobacteriaceae (ESBLs), fluconazole-resistant *Candida*, methicillin-resistant *S. aureus* (MRSA), multidrug-resistant *Acinetobacter*, multidrug-resistant *Pseudomonas aeruginosa, S. aureus*, VRE, and vancomycin-resistant *S. aureus* (VRSA). In some embodiments, a method of the disclosure can be used to treat *Helicobacter pylori*. In some embodiments, a method of the disclosure can be used to treat *Campylobacter jejuni*. In some embodiments, the methods of the invention can be applied to agricultural pathogens.

*Helicobacter pylori: Helicobacter pylori* (*H. pylori*), is a spiral-shaped gram-negative bacterium often found in the human stomach. To avoid the acidic environment found in the interior of the stomach, *H. pylori* possesses flagella to burrow into the mucus lining of the stomach and reach the epithelial cells found there. *H. pylori* is microaerophilic (i.e., requires oxygen but at lower than atmospheric concentrations) and produces a hydrogenase that can oxidize molecular hydrogen made by intestinal bacteria to extract energy.

*H. pylori* infections are usually asymptomatic but can result in gastritis or ulcers of both the stomach and the upper section of the small intestine. *H. pylori* has also been associated with lymphomas of the mucosa-associated lymphoid tissue in the stomach, esophagus, colon, and rectum, as well as tissues around the eye (extranodal marginal zone B-cell lymphoma of the effected organ), and of lymphoid tissue in the stomach (diffuse large B-cell lymphoma). The infection's association with these cancers occurs in less than 20% of cases.

In uncomplicated *H. pylori* infections in patients with peptic ulcer, therapy is administered to eliminate the pathogen and allow the ulcer(s) to heal. Standard first-line therapy consists of 7 days of combination therapy of proton-pump inhibitors (e.g., omeprazole) with the antibiotics clarithromycin and amoxicillin. Metronidazole can be used for subjects allergic to penicillins. The incidence of antibiotic-resistant *H. pylori* has been increasing, necessitating longer courses of therapy with additional antibiotics (e.g., tetracycline, nitroimidazole, levofloxacin, etc.).

*Campylobacter jejuni: Campylobacter jejuni*, a gram-negative bacterium, is one of the most common causes of food poisoning in both the United States and Europe. The majority of infections result from exposure to raw or under-cooked poultry. *Campylobacter* infection the most common cause of diarrheal disease in the United States. The infection can progress to irritable bowel syndrome (IBS), arthritis, and Guillian-Barre syndrome (GBS).

Although most infections are self-limited, groups at higher risk of progression to severe disease exist. These include those over the age of 65 years, pregnant women, and patients with weakened immune systems. Antimicrobial therapy is indicated for people who are severely ill or at risk for developing severe disease. Azithromycin and fluoroquinolones (e.g., ciprofloxacin) are often used for treatment, but resistance to fluoroquinolones is increasingly common. As a result, antimicrobial susceptibility testing can help guide appropriate therapy.

In some embodiments, the condition is an infection of the gastrointestinal tract. In some embodiments, the condition is a peptic ulcer, gastroenteritis, urinary tract infection, or a lower respiratory tract infection. In some embodiments, the condition is an infection associated with a burn, laceration, abrasion, bite, surgical wound, puncture wound, ulcer, complicated skin and soft tissue infection (cSSTI), skin and skin structure infection (SSSI), venous stasis ulcer, diabetic ulcer, pressure ulcer, post-surgical ulcer, post traumatic ulcer, or spontaneous ulcer.

In some embodiments, the administering is oral. In some embodiments, the administering is topical. In some embodiments, the administering is intravenous. In some embodiments, the administering is subcutaneous. In some embodiments, the administering is ocular. In some embodiments, the administering is by inhalation.

In some embodiments, the compound lessens an activity of a drug resistance mechanism in the microbe. In some embodiments, the compound blocks a RecA pathway. In some embodiments, the compound blocks a MazEF pathway. In some embodiments, the compound triggers programmed cell death. In some embodiments, the compound triggers error prone DNA polymerase repair.

In some embodiments, a therapy of the disclosure has synergistic activity in combination with an antibiotic. Synergy can refer to the observation that the combination of two therapeutic agents can have an overall effect that is greater than the sum of the two individual effects. Synergy can also refer to the observation that a single drug produces no effect but, when administered with a second drug produces an effect that is greater than the effect produced by the second therapeutic agent alone.

Classes of antibiotics that can be used in a method of invention include, for example, aminoglycosides, ansamycins, β-lactams, carbapenems, cephalosporins, glycopeptides, lincosamides, lipopeptides, macrolides, monobactams, nitrofurans, oxazolidinones, penicillins, polypeptides, quinolones, fluroquinolones, sulfonamides, and tetracyclines.

Non-limiting examples of antibiotics that can be used in a method of the invention include ampicillin, amoxicillin, azithromycin, carbenicillin, clarithromycin, dicloxicillin, doxycycline, erythromycin, gentamicin, kanamycin, methicillin, neomycin, norfloxacin, oxacillin, PMB, colisitin, penicillin, penicillin G, penicillin V, streptomycin, tetracycline, tobramycin, polyethyleneimine, lactic acid, benzoic acid bacitracin, imipenem, and vancomycin.

Subjects can be, for example, elderly adults, adults, adolescents, pre-adolescents, children, toddlers, infants, and non-human animals. In some embodiments, a subject is a patient. Non-human animal subjects can be, for example, a mouse, rat, a chicken, a rabbit, a dog, a cat, or a cow. Compounds of the invention can be employed in places where the spread of drug-resistant bacteria can be more likely, for example, hospitals, nursing homes, dormitories, homeless shelters, military barracks, schools, locker rooms, gymnasiums, and prisons. The methods of the invention can be applied to, for example, fomites, surgical instruments, tables, chairs, doors, eating utensils, bedding, beds, and keyboards.

In some embodiments, the methods of the invention can be applied to, for example, a plant, a fungus, or a parasite. Administration can, for example, kill or inhibit the Plant, fungus, or parasite, or kill or inhibit an agent that harms or presents a risk of harm to a plant or fungus, or lessen a likelihood of such risk. For example, agricultural applications to inhibit the spread of and damage by agriculturally-detrimental microbes are possible.

Pharmaceutical Compositions of the Invention.

A pharmaceutical composition of the invention can be used, for example, before, during, or after treatment of a subject with light, antibiotics, or another pharmaceutical agent.

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N,N'-bis(2-ethanesulfonic acid) buffer (PIPES), and saline sodium citrate buffer (SSC). Non-limiting examples of cosolvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the invention is administered in combination with, before, or after an antibiotic. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules.

Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg. In some embodiments, a compound is administered in an amount of about 100 mg. In some embodiments, a compound is administered in an amount of about 250 mg. In some embodiments, a compound is administered in an amount of about 500 mg. In some embodiments, a compound is administered in an amount of about 1000 mg. In some embodiments, a compound is administered in an amount of about 1200 mg. In some embodiments, a compound is administered in an amount of about 1500 mg. In some embodiments, a compound is administered in an amount of about 2000 mg.

In some embodiments, a dose can be expressed in terms of an amount of the drug divided by the mass of the subject, for example, milligrams of drug per kilograms of subject body mass. In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg. In some embodiments, a compound is administered in an amount of about 1 mg/kg. In some embodiments, a compound is administered in an amount of about 10 mg/kg. In some embodiments, a compound is administered in an amount of about 25 mg/kg. In some embodiments, a compound is administered in an amount of about 50 mg/kg. In some embodiments, a compound is administered in an amount of about 100 mg/kg.

EXAMPLES

Example 1: Synthetic Methods

General procedure for the synthesis of 4-benzyloxy-3-((2-arylhydrazineylidene) methyl)-1H-indoles. 4-Benzyloxyindole-3-aldehyde (0.5 mM) and p-bromophenyl hadrazine hydrochloride (0.8 mM) were mixed together and dissolved in ethanol. Compounds were stirred under room temperature or heat for several hours. Completion of the reaction was monitored using TLC analysis. In some cases, completion of the reaction required adding 0.16 mM of sodium acetate to the reaction mixture. The product was precipitated or separated by column chromatography.

Example 2: Compounds of the Disclosure

Compounds synthesized using methods analogous to the procedure of EXAMPLE 1 are shown in TABLE 1 below.

TABLE 1

| Compound No. | Structure | IUPAC |
|---|---|---|
| 1 | 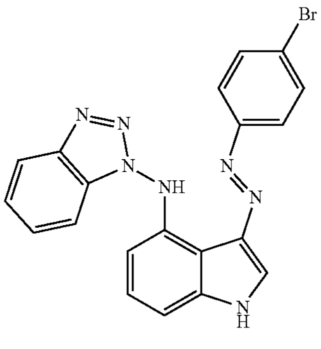 [SMILES: Brc1ccc(/N=N/c2c[nH]c3cccc(Nn4nnc5ccccc54)c23)cc1] | (E)-N-(3-((4-bromophenyl)diazenyl)-1H-indol-4-yl)-1H-benzo[d][1,2,3]triazol-1-amine |

TABLE 1-continued
| Compound No. | Structure | IUPAC |
| --- | --- | --- |
| 2 | 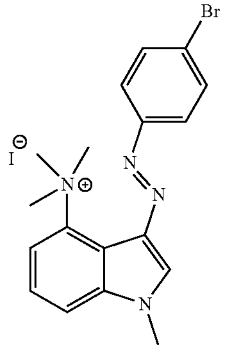 [SMILES: [I-] ; Cn1cc(/N=N/c2ccc(Br)cc2)c2c([N+](C)(C)C)cccc21] | (E)-3-((4-bromophenyl)diazenyl)-N,N,N,1-tetramethyl-1H-indol-4-aminium iodide |
| 3 | 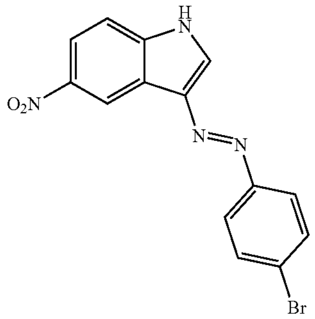 [SMILES: O=[N+]([O-])c1ccc2[nH]cc(/N=N/c3ccc(Br)cc3)c2c1] | (E)-3-((4-bromophenyl)diazenyl)-5-nitro-1H-indole |
| 4 | 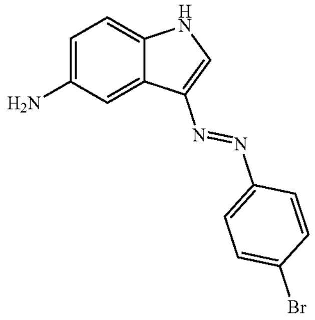 | (E)-3-((4-bromophenyl)diazenyl)-1H-indol-5-amine |
| 5 | 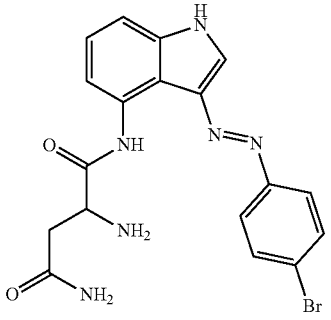 [SMILES: NC(=O)CC(N)C(=O)Nc1cccc2[nH]cc(/N=N/c3ccc(Br)cc3)c12] | (E)-2-amino-$N^1$-(3-((4-bromophenyl)diazenyl)-1H-indol-4-yl)succinamide |

TABLE 1-continued
| Compound No. | Structure | IUPAC |
| --- | --- | --- |
| 6 | 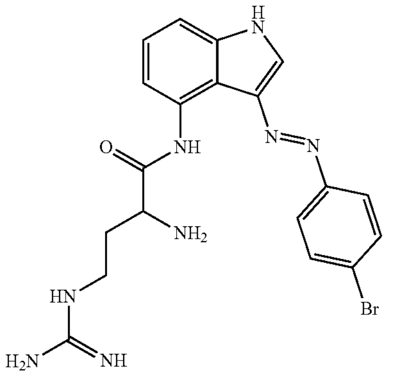 [SMILES: N=C(N)NCCC(N)C(=O)Nc1cccc2[nH]cc(/N=N/c3ccc(Br)cc3)c12] | (E)-2-amino-N-(3-((4-bromophenyl)diazenyl)-1H-indol-4-yl)-4-guanidinobutanamide |
| 7 | 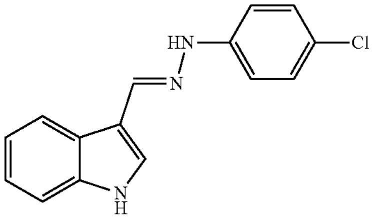 [SMILES: Clc1ccc(N/N=C/c2c[nH]c3ccccc23)cc1] | (E)-3-((2-(4-chlorophenyl)hydrazineylidene)methyl)-1H-indole |
| 8 | 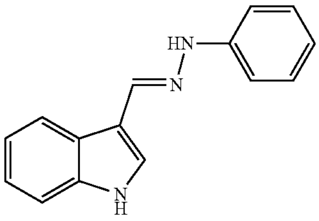 [SMILES: C(=N\Nc1ccccc1)/c1c[nH]c2ccccc12] | (E)-3-((2-phenylhydrazineylidene)methyl)-1H-indole |
| 9 | 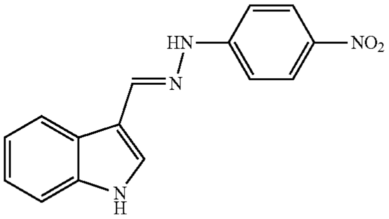 [SMILES: O=[N+]([O-])c1ccc(N/N=C/c2c[nH]c3ccccc23)cc1] | (E)-3-((2-(4-nitrophenyl)hydrazineylidene)methyl)-1H-indole |
| 10 | 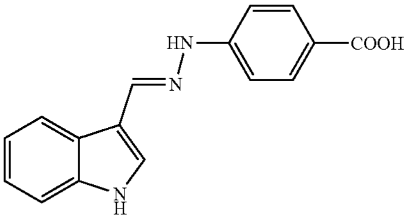 [SMILES: O=C(O)c1ccc(N/N=C/c2c[nH]c3ccccc23)cc1] | (E)-4-(2-((1H-indol-3-yl)methylene)hydrazineyl)benzoic acid |
| 11 | 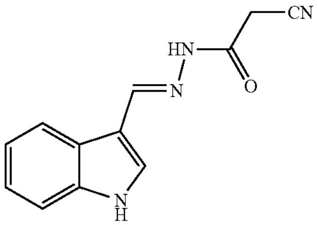 [SMILES: N#CCC(=O)N/N=C/c1c[nH]c2ccccc12] | (E)-N'-((1H-indol-3-yl)methylene)-2-cyanoacetohydrazide |

TABLE 1-continued
| Compound No. | Structure | IUPAC |
| --- | --- | --- |
| 12 | 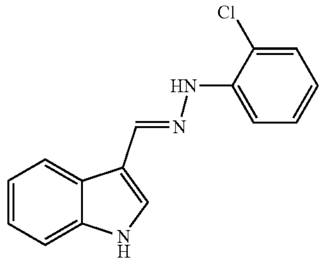 [SMILES: Clc1ccccc1N/N=C/c1c[nH]c2ccccc12] | (E)-3-((2-(2-chlorophenyl)hydrazineylidene) methyl)-1H-indole |
| 13 | 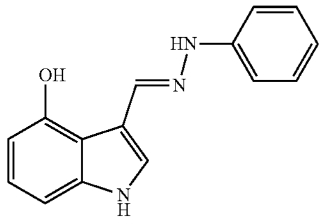 [SMILES: Oc1cccc2[nH]cc(/C=N/Nc3ccccc3)c12] | (E)-3-((2-phenylhydrazineylidene) methyl)-1H-indol-4-ol |
| 14 | 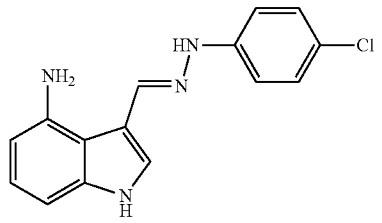 [SMILES: Nc1cccc2[nH]cc(/C=N/Nc3ccc(Cl)cc3)c12] | (E)-3-((2-(4-chlorophenyl)hydrazineylidene) methyl)-1H-indol-4-amine |
| 15 | 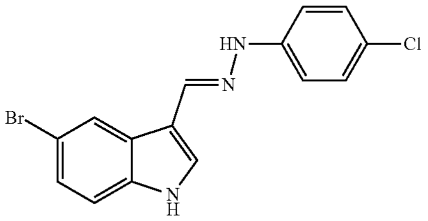 [SMILES: Clc1ccc(N/N=C/c2c[nH]c3ccc(Br)cc23)cc1] | (E)-5-bromo-3-((2-(4-chlorophenyl)hydrazineylidene) methyl)-1H-indole |
| 16 | 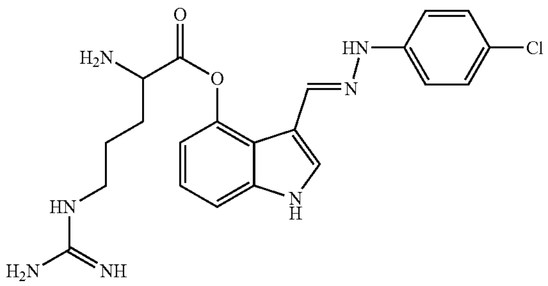 [SMILES: N=C(N)NCCCC(N)C(=O)Oc1cccc2[nH]cc(/C=N/Nc3ccc(Cl)cc3)c12] | (E)-3-((2-(4-chlorophenyl)hydrazineylidene) methyl)-1H-indol-4-yl argininate |

TABLE 1-continued
| Compound No. | Structure | IUPAC |
| --- | --- | --- |
| 17 | 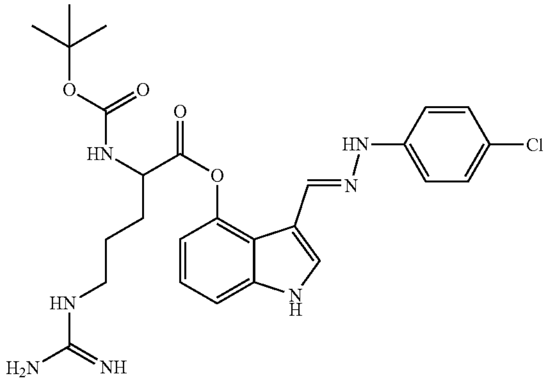 [SMILES: CC(C)(C)OC(=O)NC(CCCNC(=N)N)C(=O)Oc1cccc2[nH]cc(/C=N/Nc3ccc(Cl)cc3)c12] | (E)-3-((2-(4-chlorophenyl)hydrazineylidene) methyl)-1H-indol-4-yl (tert-butoxycarbonyl) argininate |
| 18 | 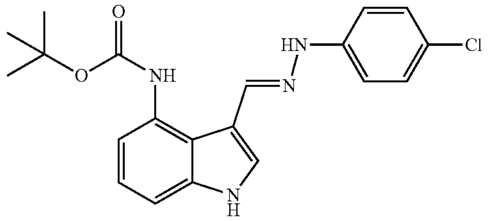 [SMILES: CC(C)(C)OC(=O)Nc1cccc2[nH]cc(/C=N/Nc3ccc(Cl)cc3)c12] | tert-butyl (E)-3-((2-(4-chlorophenyl)hydrazineylidene) methyl)-1H-indol-4-yl)carbamate |
| 19 | 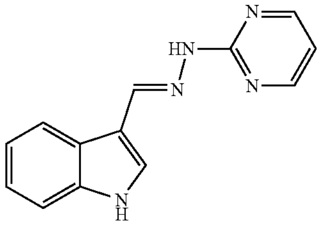 [SMILES: C(=N\Nc1ncccn1)/c1c[nH]c2ccccc12] | (E)-3-((2-(pyrimidin-2-yl)hydrazineylidene)methyl)-1H-indole |
| 20 | 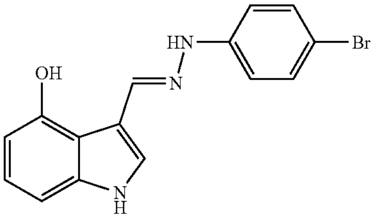 [SMILES: Oc1cccc2[nH]cc(/C=N/Nc3ccc(Br)cc3)c12] | (E)-3-((2-(4-bromophenyl)hydrazineylidene) methyl)-1H-indol-4-ol |
| 21 | 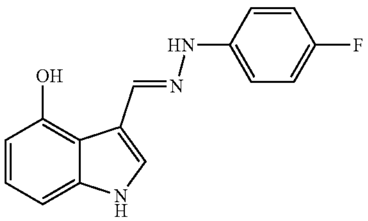 [SMILES: Oc1cccc2[nH]cc(/C=N/Nc3ccc(F)cc3)c12] | (E)-3-((2-(4-fluorophenyl)hydrazineylidene) methyl)-1H-indol-4-ol |

TABLE 1-continued

| Compound No. | Structure | IUPAC |
| --- | --- | --- |
| 22 | 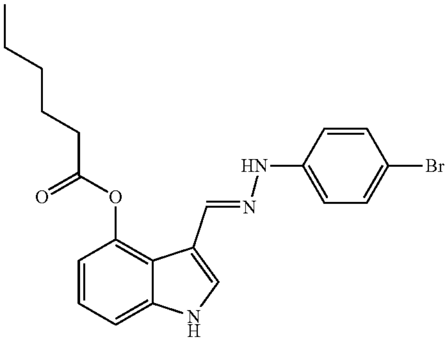 [SMILES: CCCCCC(=O)Oc1cccc2[nH]cc(/C=N/Nc3ccc(Br)cc3)c12] | (E)-3-((2-(4-bromophenyl)hydrazineylidene) methyl)-1H-indol-4-yl hexanoate |
| 23 | 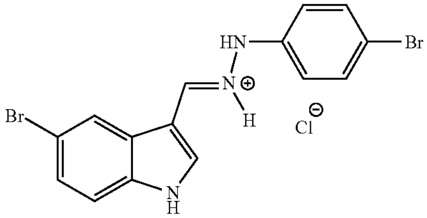 [SMILES: Brc1ccc(N/[NH+]=C/c2c[nH]c3ccc(Br)cc23)cc1 ; [Cl-]] | (E)-1-((5-bromo-1H-indol-3-yl)methylene)-2-(4-bromophenyl)hydrazin-1-ium chloride |
| 24 | 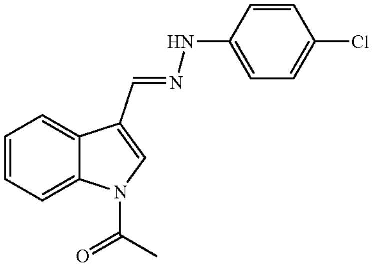 [SMILES: CC(=O)n1cc(/C=N/Nc2ccc(Cl)cc2)c2ccccc21] | (E)-1-(3-((2-(4-chlorophenyl)hydrazineylidene) methyl)-1H-indol-1-yl)ethan-1-one |
| 25 | 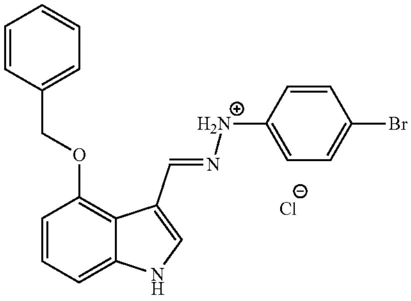 [SMILES: Brc1ccc([NH2+]/N=C/c2c[nH]c3cccc(OCc4ccccc4)c23)cc1 ; [Cl-]] | (E)-2-((4-(benzyloxy)-1H-indol-3-yl)methylene)-1-(4-bromophenyl)hydrazin-1-ium chloride |
| 26 | 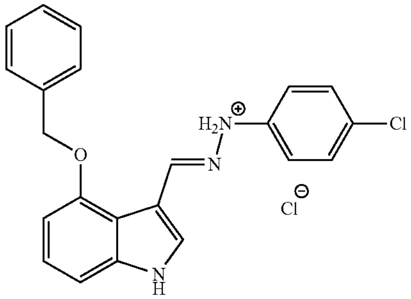 [SMILES: Clc1ccc([NH2+]/N=C/c2c[nH]c3cccc(OCc4ccccc4)c23)cc1 ; [Cl-]] | (E)-2-((4-(benzyloxy)-1H-indol-3-yl)methylene)-1-(4-chlorophenyl)hydrazin-1-ium |

TABLE 1-continued
| Compound No. | Structure | IUPAC |
|---|---|---|
| 27 | 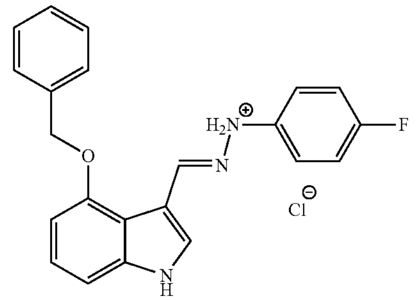 [SMILES: Fc1ccc([NH2+]/N=C/c2c[nH]c3cccc(OCc4ccccc4)c23)cc1 ; [Cl-]] | (E)-2-((4-(benzyloxy)-1H-indol-3-yl)methylene)-1-(4-fluorophenyl)hydrazin-1-ium |
| 28 | 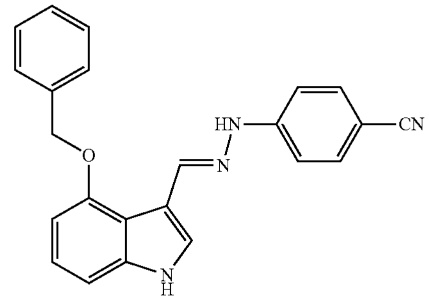 [SMILES: N#Cc1ccc(N/N=C/c2c[nH]c3cccc(OCc4ccccc4)c23)cc1] | (E)-4-(2-((4-benzyloxy)-1H-indol-3-yl)methylene)hydrazineyl) benzonitrile |
| 29 | 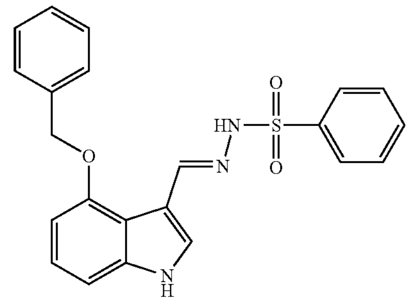 [SMILES: O=S(=O)(N/N=C/c1c[nH]c2cccc(OCc3ccccc3)c12)c1ccccc1] | (E)-N'-((4-(benzloxy)-1H-indol-3-yl)methylene)benzenesulfonohydrazide |
| 30 | 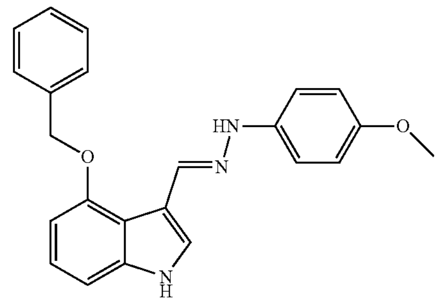 [SMILES: COc1ccc(N/N=C/c2c[nH]c3cccc(OCc4ccccc4)c23)cc1] | (E)-4-(benzyloxy)-3-((2-(4-methoxyphenyl) hydrazineylidene)methyl)-1H-indole |
| 31 | 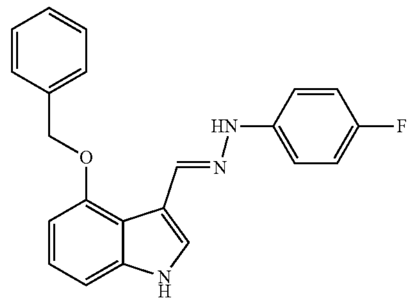 [SMILES: Fc1ccc(N/N=C/c2c[nH]c3cccc(OCc4ccccc4)c23)cc1] | (E)-4-(benzyloxy)-3-((2-(4-fluorophenyl)hydrazineylidene) methyl)-1H-indole |

TABLE 1-continued

| Compound No. | Structure | IUPAC |
|---|---|---|
| 32 | 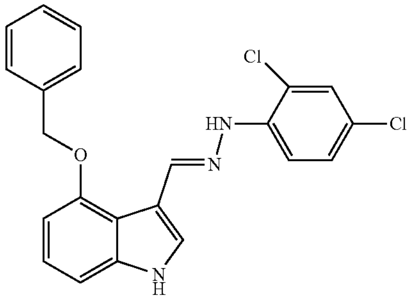 [SMILES: Clc1ccc(N/N=C/c2c[nH]c3cccc(OCc4ccccc4)c23)c(Cl)c1] | (E)-4-(benzyloxy)-3-((2-(2,4-dichlorophenyl)hydrazineylidene) methyl)-1H-indole |
| 33 | 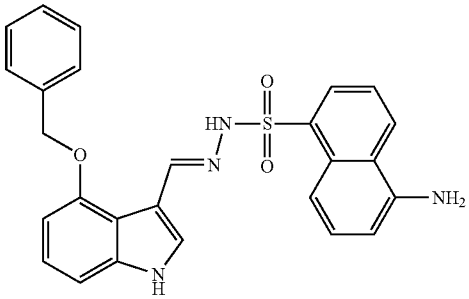 [SMILES: Nc1cccc2c(S(=O)(=O)N/N=C/c3c[nH]c4cccc(OCc5ccccc5)c34)cccc12] | (E)-5-amino-N'-((4-(benzyloxy)-1H-indol-3-yl)methylene)naphthalene-1-sulfonohydrazide |
| 34 | 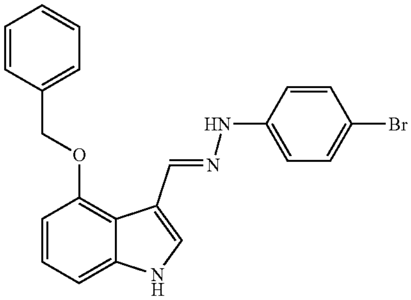 [SMILES: Brc1ccc(N/N=C/c2c[nH]c3cccc(OCc4ccccc4)c23)cc1] | (E)-4-(benzyloxy)-3-((2-(4-bromophenyl)hydrazineylidene) methyl)-1H-indole |
| 35 | 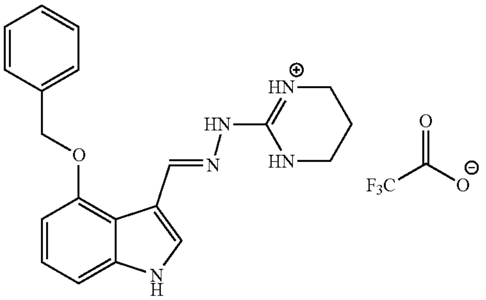 [SMILES: C(=N\NC1=[NH+]CCCN1)/c1c[nH]c2cccc(OCc3ccccc3)c12 ; O=C([O-])C(F)(F)F] | (E)-2-(2-((4-(benzyloxy)-1H-indol-3-yl)methylene)hydrazineyl)-3,4,5,6-tetrahydropyrimidin-1-ium 2,2,2-trifluoroacetate |
| 36 | 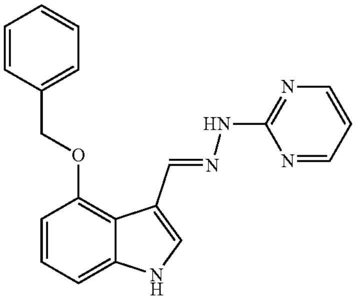 [SMILES: C(=N\Nc1ncccn1)/c1c[nH]c2cccc(OCc3ccccc3)c12] | (E)-4-(benzyloxy)-3-((2-(pyrimidin-2-yl)hydrazineylidene)methyl)-1H-indole |

TABLE 1-continued

| Compound No. | Structure | IUPAC |
|---|---|---|
| 37 | 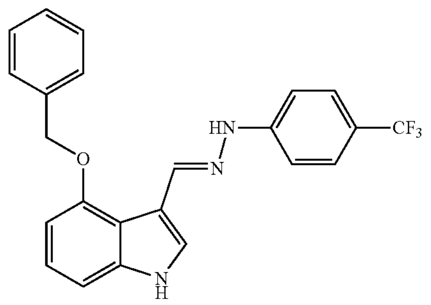 [SMILES: FC(F)(F)c1ccc(N/N=C/c2c[nH]c3cccc(OCc4ccccc4)c23)cc1] | (E)-4-(benzyloxy)-3-((2-(4-(trifluoromethyl)phenyl) hydrazineylidene)methyl)-1H-indole |
| 38 | 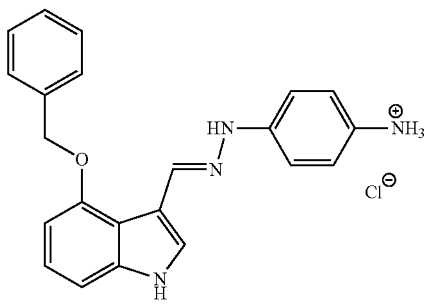 [SMILES: [NH3+]c1ccc(N/N=C/c2c[nH]c3cccc(OCc4ccccc4)c23)cc1 ; [Cl-]] | (E)-4-(2-((4-(benzyloxy)-1H-indol-3-yl)methylene)hydrazineyl) benzenaminium chloride |
| 39 | 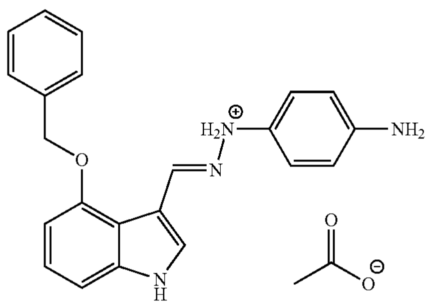 | (E)-1-(4-aminophenyl)-2-((4-(benzyloxy)-1H-indol-3-yl)methylene)hydrazin-1-ium acetate |
| 40 | 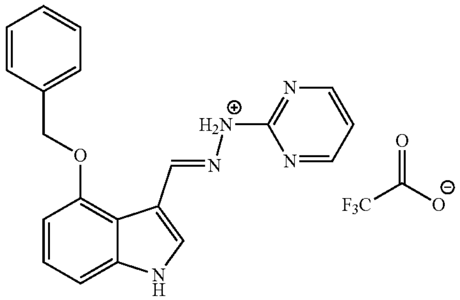 [SMILES: C(=N\[NH2+]c1ncccn1)/c1c[nH]c2cccc(OCc3ccccc3)c12 ; O=C([O-])C(F)(F)F] | (E)-2-((4-(benzyloxy)-1H-indol-3-yl)methylene)-1-(pyrimidin-2-yl)hydrazin-1-ium 2,2,2-trifluoroacetate |
| 41 | 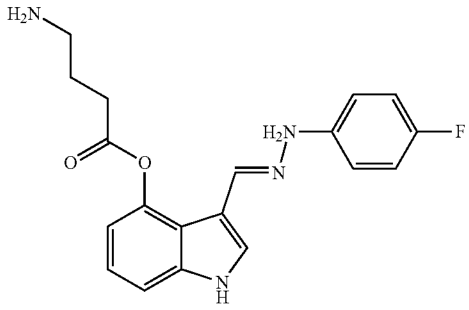 [SMILES: NCCCC(=O)Oc1cccc2[nH]cc(/C=N/Nc3ccc(F)cc3)c12] | (E)-3-((2-(4-fluorophenyl)hydrazineylidene) methyl)-1H-indol-4-yl 4-aminobutanoate |

TABLE 1-continued
| Compound No. | Structure | IUPAC |
|---|---|---|
| 42 | 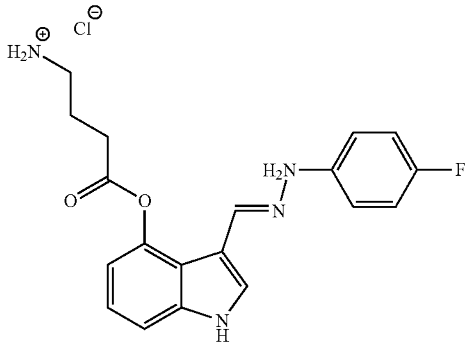 [SMILES: [Cl-] ; [NH3+]CCCC(=O)Oc1cccc2[nH]cc(/C=N/Nc3ccc(F)cc3)c12] | (E)-4-((3-((2-(4-fluorophenyl)hydrazineylidene) methyl)-1H-indol-4-yl)oxy)-4-oxobutan-1-aminium chloride |
| 43 | 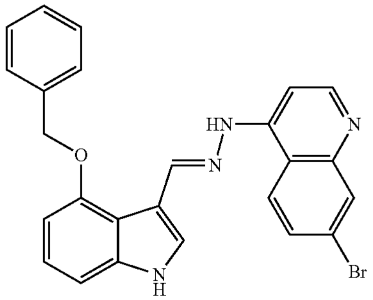 [SMILES: Brc1ccc2c(N/N=C/c3c[nH]c4cccc(OCc5ccccc5)c34)ccnc2c1] | (E)-4-(2-((4-(benzyloxy)-1H-indol-3-yl)methylene)hydrazineyl)-7-bromoquinoline |
| 44 | 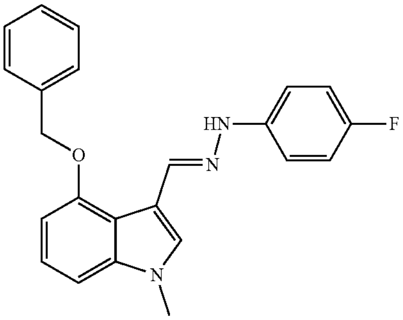 [SMILES: Cn1cc(/C=N/Nc2ccc(F)cc2)c2c(OCc3ccccc3)cccc21] | (E)-4-(benzyloxy)-3-((2-(4-fluorophenyl)hydrazineylidene) methyl)-1-methyl-1H-indole |
| 45 | 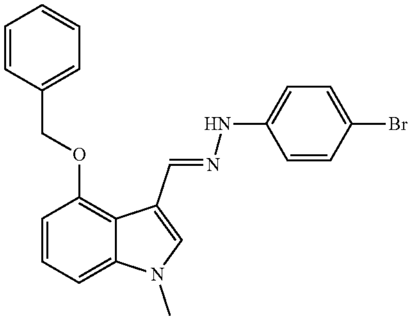 [SMILES: Cn1cc(/C=N/Nc2ccc(Br)cc2)c2c(OCc3ccccc3)cccc21] | (E)-4-(benzyloxy)-3-((2-(4-bromophenyl)hydrazineylidene) methyl)-1-methyl-1H-indole |

TABLE 1-continued
| Compound No. | Structure | IUPAC |
|---|---|---|
| 46 | 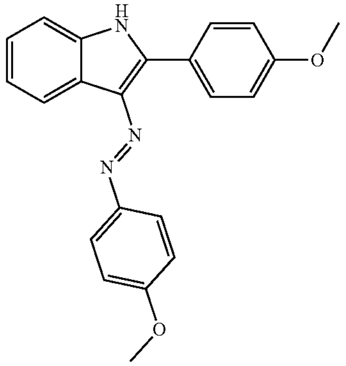 [SMILES: COc1ccc(/N=N/c2c(-c3ccc(OC)cc3)[nH]c3ccccc23)cc1] | (E)-2-(4-methoxyphenyl)-3-((4-methoxyphenyl)diazenyl)-1H-indole |
| 47 | 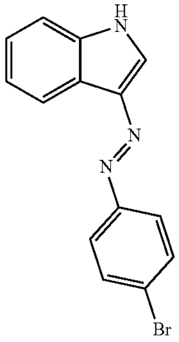 [SMILES: Brc1ccc(/N=N/c2c[nH]c3ccccc23)cc1] | (E)-3-((4-bromophenyl)diazenyl)-1H-indole |
| 48 | 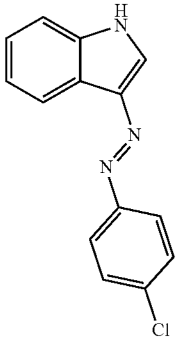 [SMILES: Clc1ccc(/N=N/c2c[nH]c3ccccc23)cc1] | (E)-3-((4-chlorophenyl)diazenyl)-1H-indole |
| 49 | 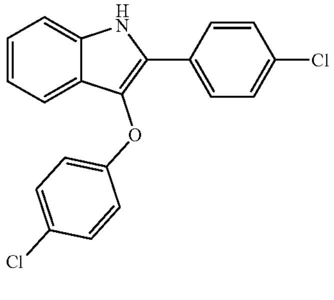 [SMILES: Clc1ccc(Oc2c(-c3ccc(Cl)cc3)[nH]c3ccccc23)cc1] | 3-(4-chlorophenoxy)-2-(4-chlorophenyl)-1H-indole |

TABLE 1-continued

| Compound No. | Structure | IUPAC |
| --- | --- | --- |
| 50 | 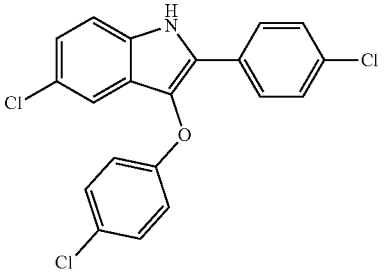 [SMILES: Clc1ccc(Oc2c(-c3ccc(Cl)cc3)[nH]c3ccc(Cl)cc23)cc1] | 5-chloro-3-(4-chlorophenoxy)-2-(4-chlorophenyl)-1H-indole |

Figure 5A:
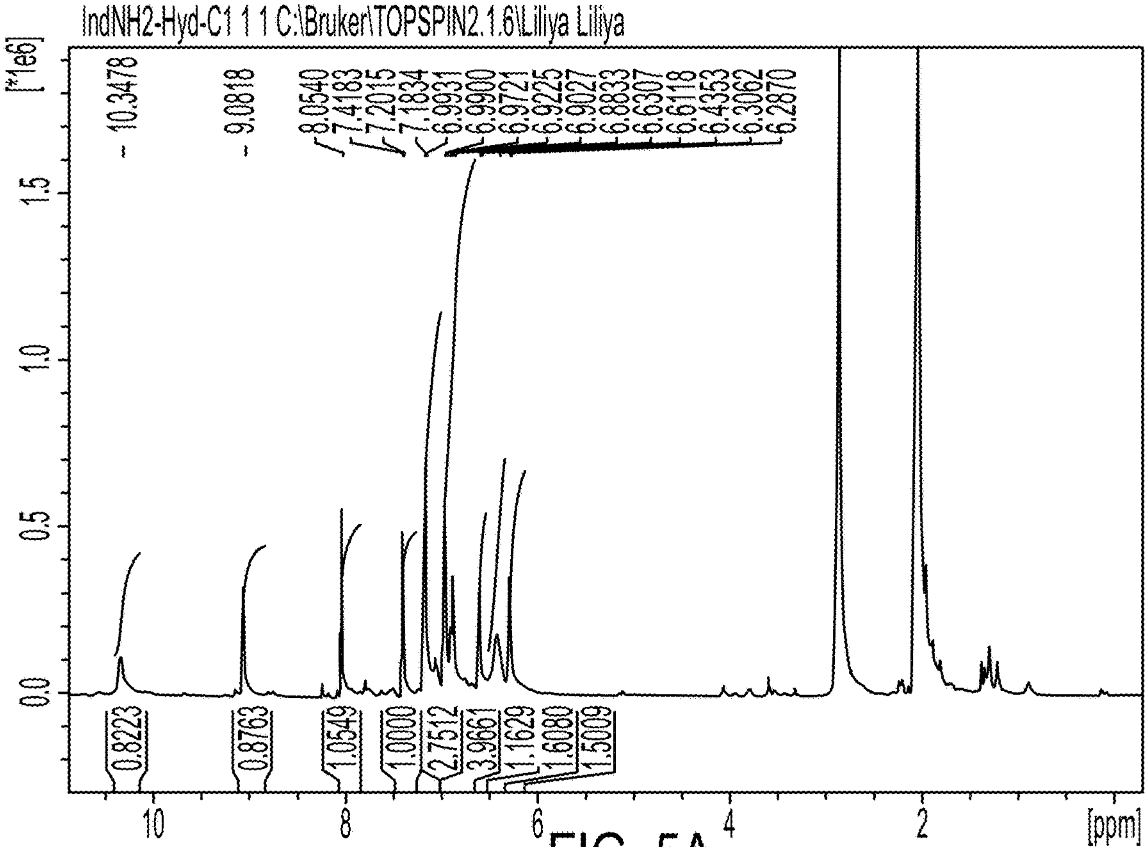
FIGS. 5A and 5B show NMR characterization data for Compound 14.
Figure 5B:
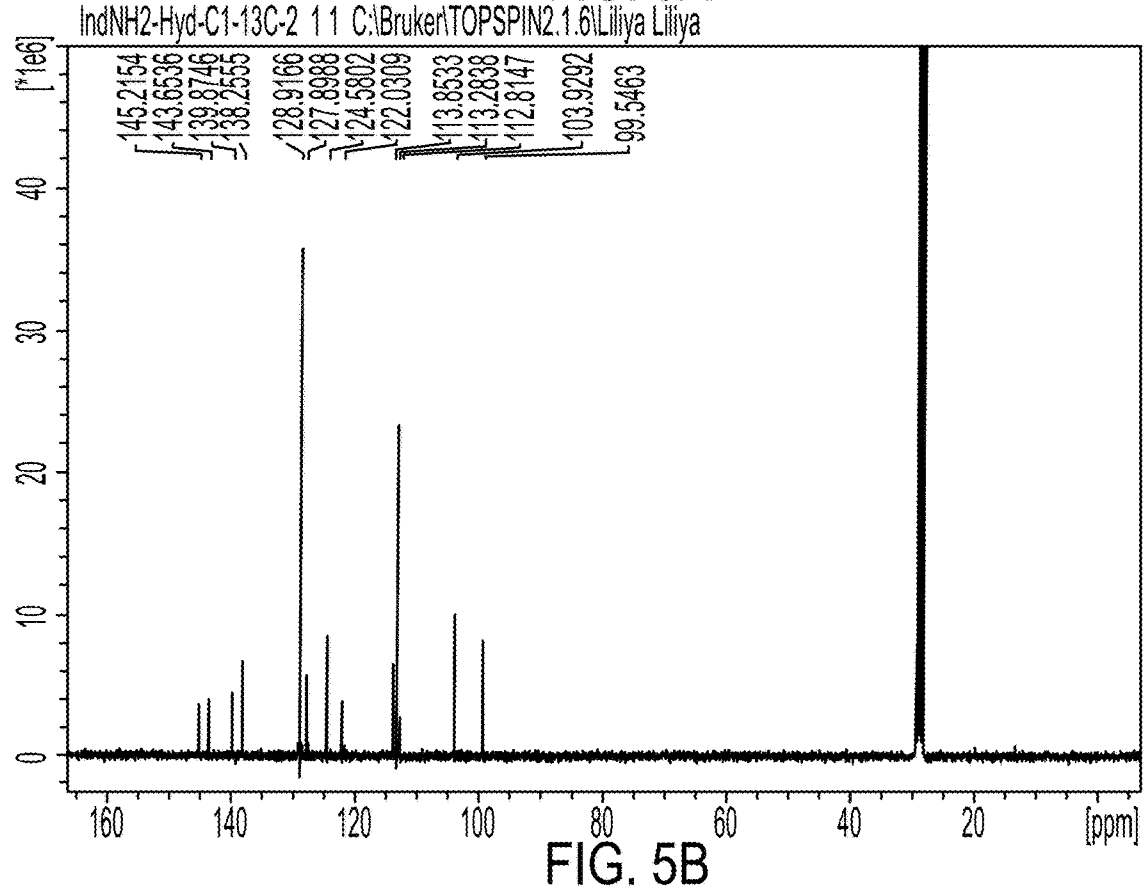

Compound 14: Yield 2.35%, 1H NMR (400 MHZ, DMSO) d 10.34 (br s, 1H), 9.08 (1H), 8.05 (1H), 7.42 (1H), 7.20-6.88 (m, 6H), 6.62 (d, J=7.6 Hz, 1H), 6.43 (br s, 2H), 6.29 (d, J=7.7 Hz, 1H); 13C NMR (100 MHz, DMSO) δ 145.2, 143.7, 139.9, 138.3, 128.9, 127.9, 124.6, 122.0, 113.9, 113.3, 112.8, 103.9, 99.5. FIG. 5A and FIG. 5B show NMR characterization data for Compound 14.

Figure 6A:
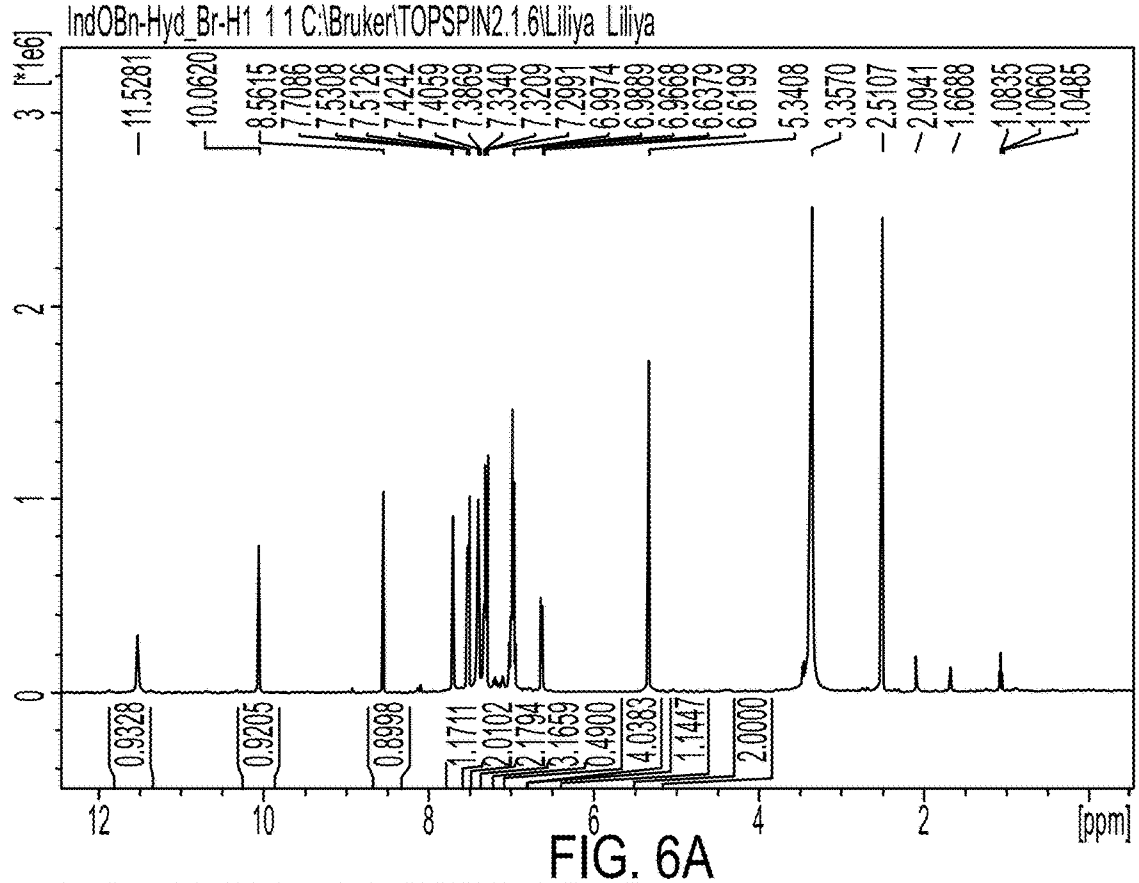
FIGS. 6A and 6B show NMR characterization data for Compound 25.
Figure 6B:
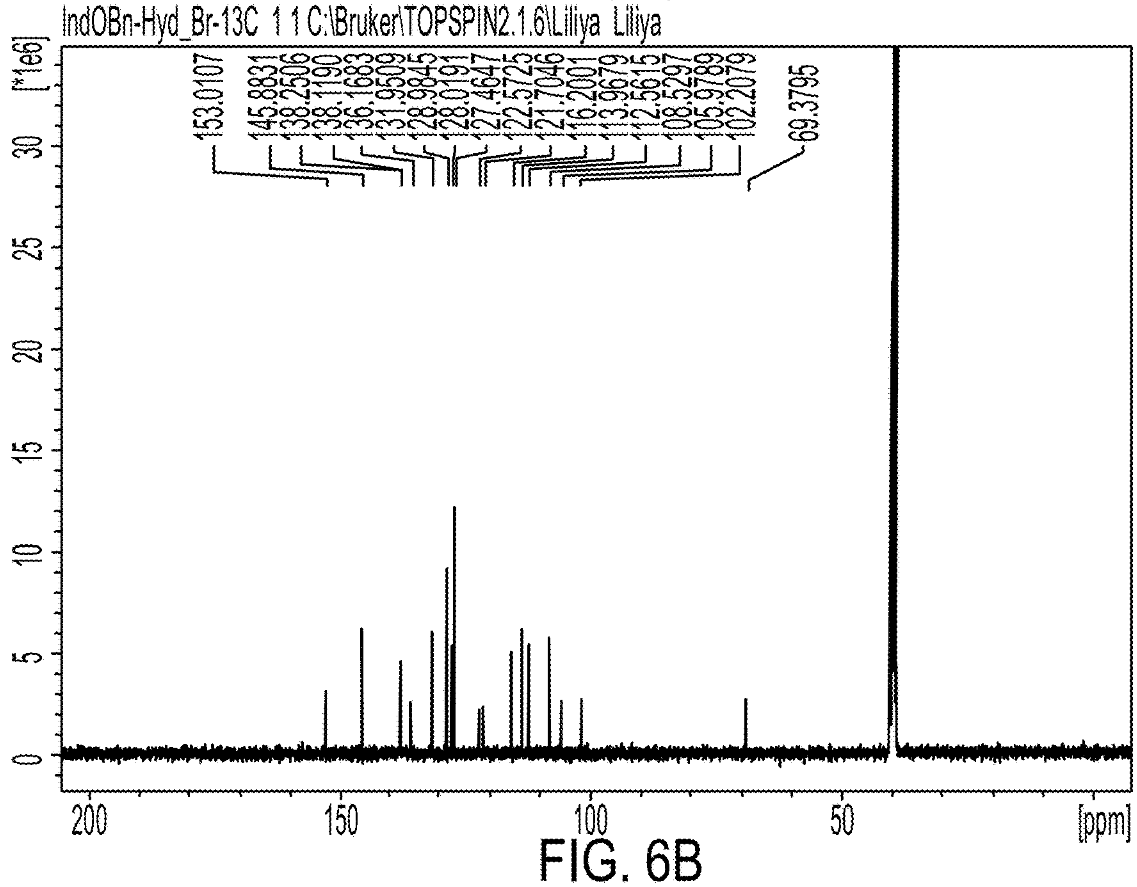

Compound 25: Yield 83%, 1H NMR (400 MHZ, DMSO) d 11.52 (br s, 1H), 10.06 (1H), 8.56 (1H), 7.71 (11H), 7.53-6.97 (m, 7H), 7.00-6.97 (m, 4H), 6.63 (d, J=7.2 Hz, 11H), 5.34 (2H); $^{13}C$ NMR (100 MHz, DMSO) δ 153.0, 145.9, 138.3, 138.1, 136.2, 131.9, 129.0, 128.0, 127.5, 122.6, 121.7, 116.2, 114.0, 112.6, 108.5, 106.0, 102.2, 69.4. HRMS calculated for $C_{22}H_{19}BrN_3O$ (M+H$^+$) 420.0711, found 420.0724. FIG. 6A and FIG. 6B show NMR characterization data for Compound 25.

Compound 26: Yield 43%. $^1H$ NMR (400 MHz, DMSO) δ 10.62 (br s, 1H), 9.17 (11H), 8.68 (11H), 7.82 (d, J=2.4 Hz, 1H), 7.56 (d, J=7.5 Hz, 2H), 7.44-7.32 (m, 3H), 7.21-7.01 (m, 6H), 6.67 (d, J=7.6 Hz, 1H), 5.33 (2H).

Figure 7:
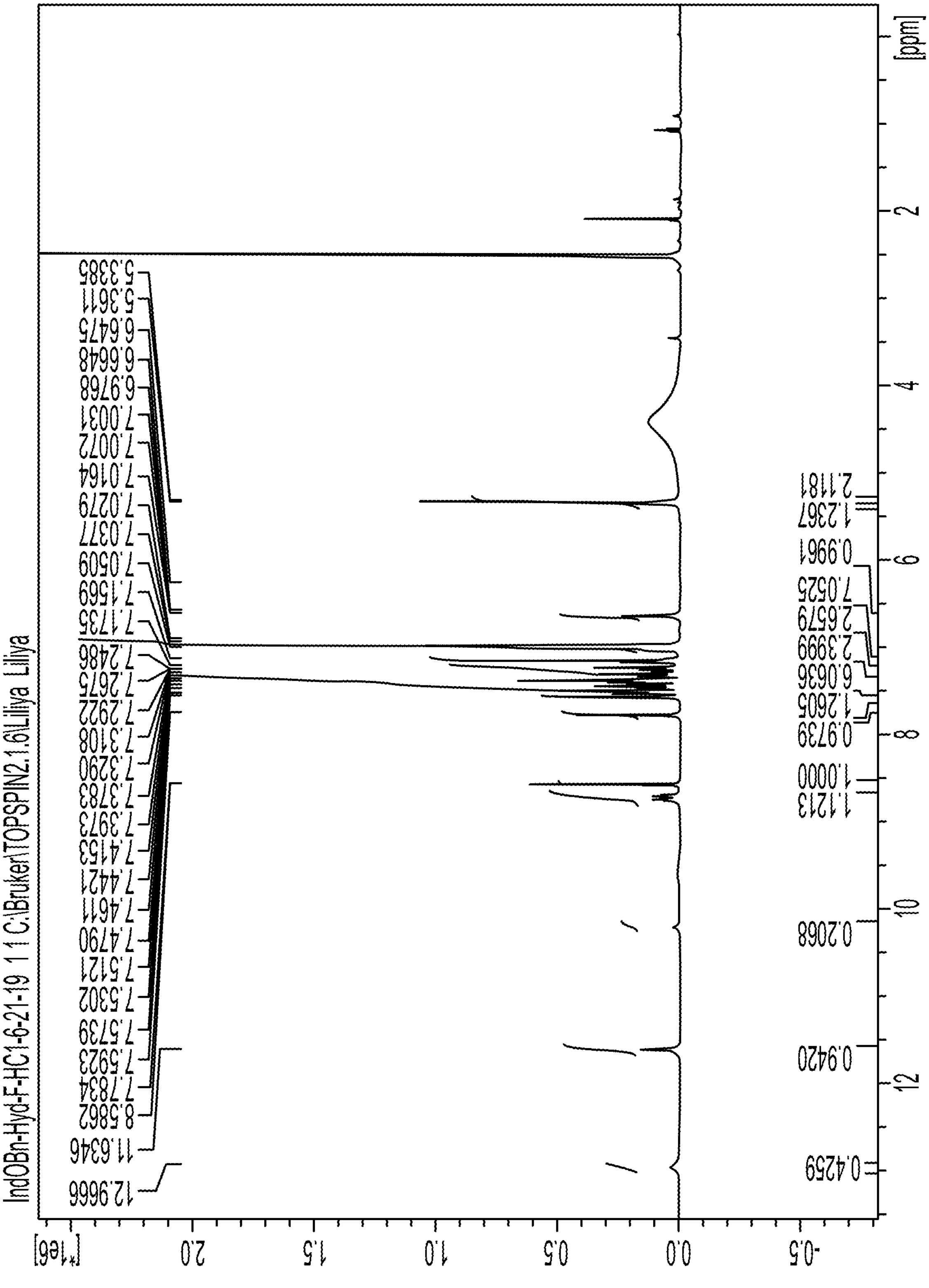
FIG. 7 shows NMR characterization data for Compound 27.

Compound 27: Yield 91%. $^1H$ NMR (400 MHz, DMSO) δ 10.22 (br s, 1H), 8.60 (11H), 7.82 (1H), 7.52 (d, J=7.4 Hz, 2H), 7.41-7.29 (m, 3H), 7.05-6.99 (m, 6H), 6.66 (d, J=6.8 Hz, 1H), 5.34 (2H). HRMS calculated for $C_{22}H_{19}FN_3O$ (M+H$^+$) 360.1512, found 360.1500. FIG. 7 shows NMR characterization data for Compound 27.

Figure 8A:
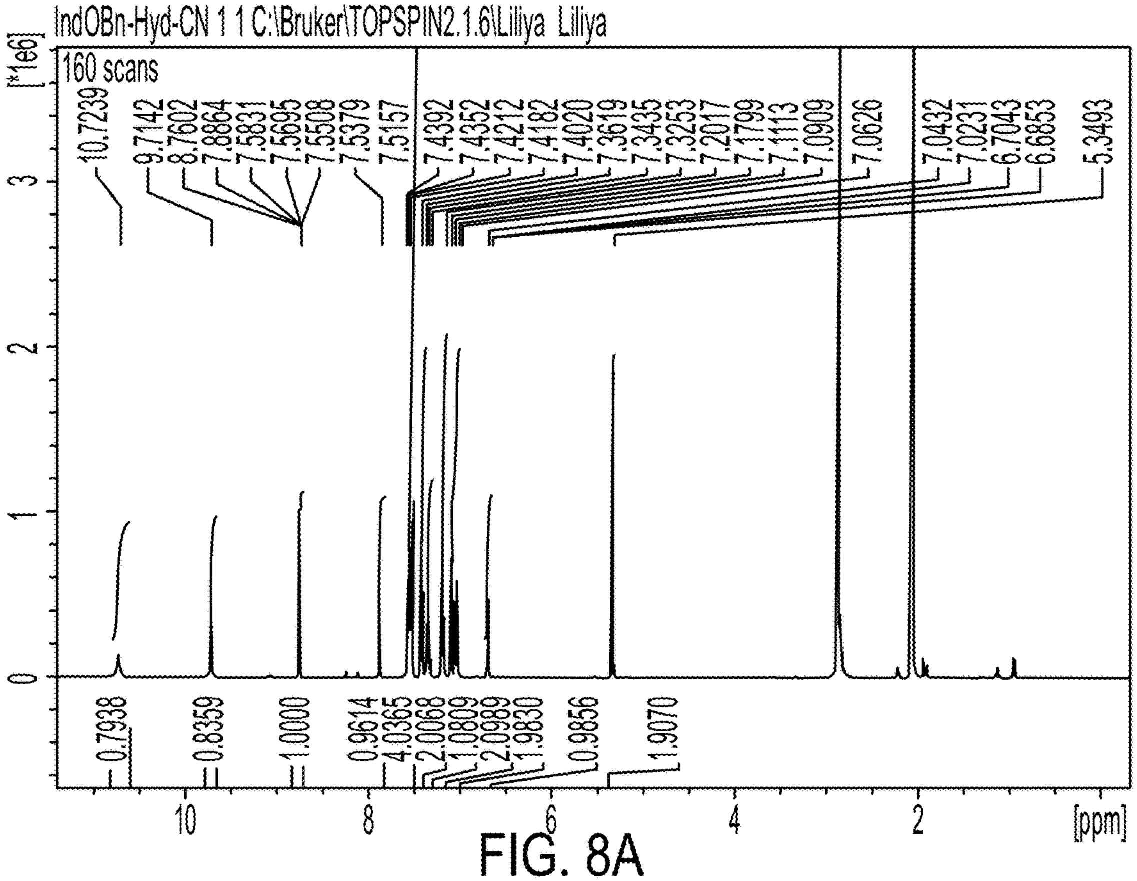
FIGS. 8A and 8B show NMR characterization data for Compound 28.
Figure 8B:
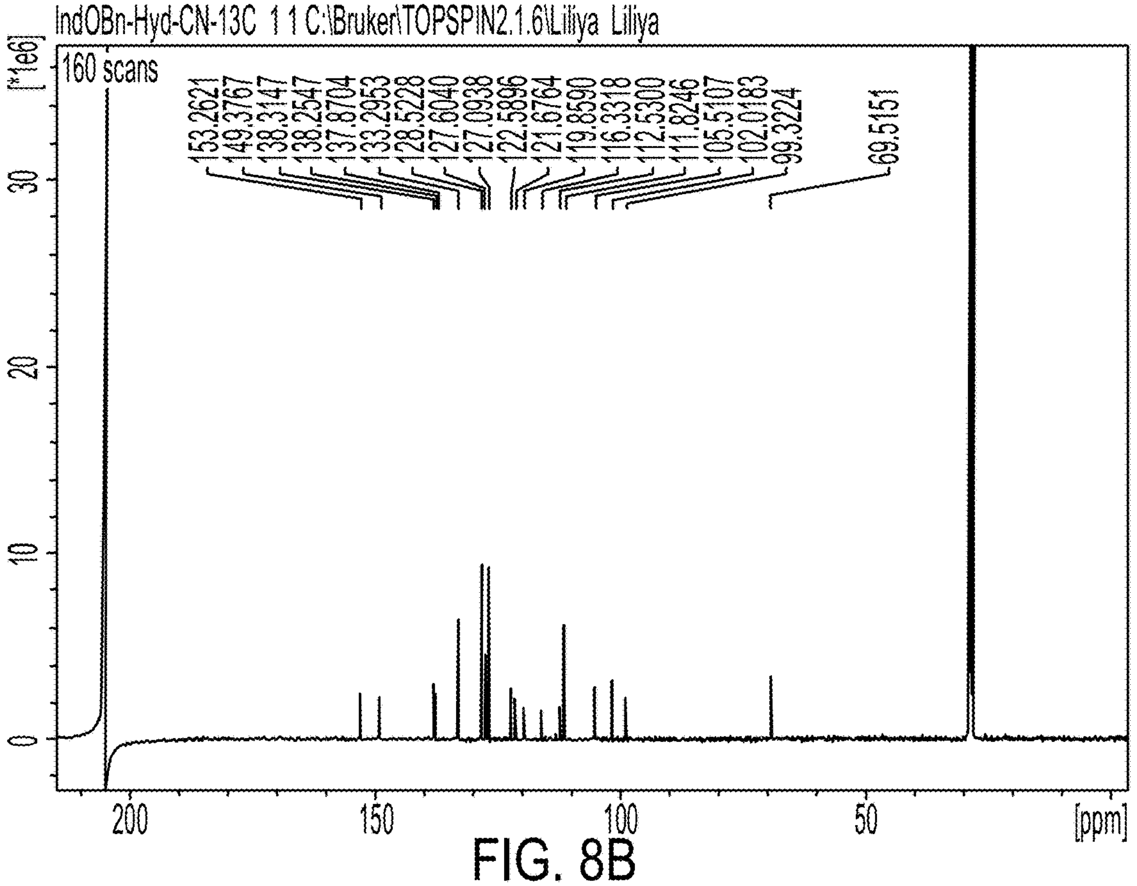

Compound 28: Yield 37%. $^1H$ NMR (400 MHz, DMSO) δ 10.72 (br s, 1H), 9.71 (1H), 8.76 (1H), 7.87 (1H), 7.58-7.32 (m, 7H), 7.20-7.02 (m, 3H), 6.69 (d, J=7.6 Hz, 1H), 5.35 (2H); $^{13}C$ NMR (100 MHz, DMSO) δ 153.3, 149.4, 138.3, 138.2, 137.9, 133.3, 128.5, 127.6, 127.1, 122.6, 121.7, 119.9, 116.3, 112.5, 111.8, 105.5, 102.0, 99.3, 69.5. FIG. 8A and FIG. 8B show NMR characterization data for Compound 28.

Example 3: Method for Obtaining MIC Data

MRSA BAA-44: MRSA ATCC BAA-44 was grown from a glycerol stock by placing a small volume of cells onto a Mueller-Hinton agar plate (MHA). The MHA plate was incubated overnight at 37° C. A single colony was used to inoculate Mueller-Hinton broth (MHB) to obtain a bacterial broth suspension. The MHB broth suspension was grown at 37° C. on a rotary shaking incubator (100 rpm) for 12 hours. The bacterial cell concentration was adjusted to ~5×10$^5$ colony forming units per milliliter (CFU/mL) in MHB−/+ 10, 20, or 40% FBS using optical density (OD) at 595 nm. 500 μL aliquots of the adjusted bacterial cell suspension were placed into borosilicate glass tubes. The cell suspensions were treated with 100 μM compound of interest and serially diluted two-fold. The culture tubes were incubated for 18 hours at 37° C. Efficacy was either assessed visually or by adding 10% v/v MTT (5 mg/mL stock) after the 18 hour incubation period, where the cell suspensions were subsequently incubated for 10 minutes to allow the MTT reagent to carry out the colorimetric reaction.

*A. baumannii: A. baumannii* ATCC BAA-1797 was grown from a glycerol stock by placing a small volume of cells onto a MHA plate. The MHA plate was incubated overnight at 37° C. A single colony was used to inoculate MHB to obtain a bacterial broth suspension. The MHB broth suspension was grown at 37° C. on a rotary shaking incubator (100 rpm) for 12 hours. The bacterial cell concentration was adjusted to ~5×10$^5$ CFU/mL in MHB or MHB+10%, 20% or 40% FBS using OD at 595 nm. 500 μL aliquots of the adjusted bacterial cell suspension were placed into borosilicate glass tubes. The cell suspensions were treated with a compound of interest, and the treatments were serially diluted two-fold. The culture tubes were incubated for 18 hours at 37° C. Efficacy was either assessed visually or by adding 10% v/v MTT (5 mg/mL stock) after the 18 hour incubation period. The cell suspensions were subsequently incubated for 10 minutes to allow the MTT reagent to carry out the colorimetric reaction. The OD was read at 595 nm.

HeLa cells: HeLa cells were trypsinized and counted in number of cells/mL using a hemocytometer. Cells were then plated at 4×10$^3$ HeLa cells/100 μL in tissue culture-treated 96-well plates in DMEM+1% penicillin/streptomycin (P/S)+10% FBS. HeLa cells were treated with 100 μM of a compound of interest and serially diluted two-fold. Samples were also prepared with no treatment, 1% DMSO, and 100 μM PAO. The cells were incubated for 48 hours at 37° C. in a humidified incubator with 5% $CO_2$. 10% v/v MTT reagent (5 mg/mL stock) was added to each sample, and the samples were incubated for 2 hours before removing the supernatant and solubilizing the samples in 100 μL DMSO. OD readings were obtained at 595 nm. $IC_{50}$ values were reported.

Example 4: Docking Study of a Compound of the Disclosure and MazEF and MazF

FIG. 1 shows molecular docking program Autodock Vina 1.1.2 ligand-protein docking images of a compound of the disclosure and EDF with MazEF and MazF. The data show that the compound interfered with MazEF partners binding to each other, allowing PCD to proceed in the same manner as induced by EDF.

Example 5: Effects of Compounds of the Disclosure and Antibiotic Resistance in *S. aureus*

Over a period of 32 days, *S. aureus* cells were exposed to sub-inhibitory concentrations of the indicated compound, norfloxacin, or oxacillin and sub-cultured at the newly emerged, sub-inhibitory concentration. Dramatic resistance to norfloxacin and oxacillin was observed. 4 out of 5 structurally-distinct compounds did not permit any increase in MIC values. The compounds of the disclosure prevented evolution of bacterial resistance to the compounds and to any co-administered stressor.

TABLE 2 shows that *S. aureus* did not develop resistance against selected compounds of the disclosure. The bolded compounds exhibited no resistance after a month of continuous sub-optimal treatment.

TABLE 2

| Compound | Initial MIC Day 0 (μM) | Final MIC Day 32 (μM) |
|---|---|---|
| **46** | **1-2** | **1-2** |
| **47** | **4** | **4** |
| **48** | **8** | **8** |
| **49** | **2** | **1** |
| 50 | 0.25-0.5 | >32 |
| Oxacillin | 0.25 μg/mL | >200 μg/mL |
| Norfloxacin | 2 μg/mL | >100 μg/mL |

Example 6: Effects of Compounds of the Disclosure on RecA/LexA Pathway in *E. coli*

An increase in DNA damage-induced RecA protein expression is required for identification and repair of DNA lesions. LexA-repressed transcription of a norfloxacin-triggered SOS response was measured by detecting an increase in RecA-GFP fusion protein fluorescence in an *E. coli* recombinant model. The compounds of the disclosure inhibited RecA-GFP induction and presumably, the concurrent SOS response. Inhibition of RecA-GFP expression correlated with an increase in cell death, most likely as a result of ALD activation. Sub-potent concentrations of Polymixin E were used to facilitate entry of the compounds into cells.

Figure 2:
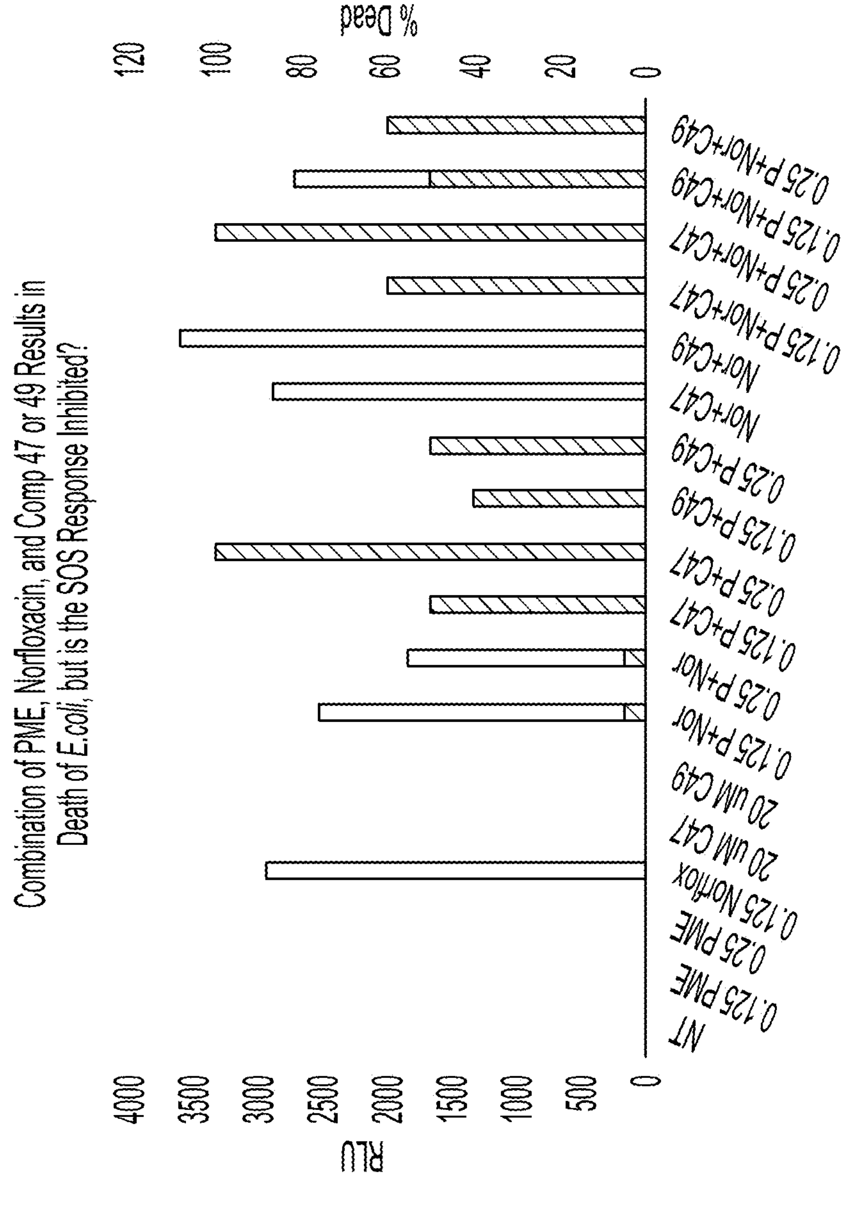
FIG. 2 shows the effect of treating *E. coli* with PME, norfloxacin, and Compound 47 or Compound 49.

*E. coli* MG1655 was grown from a glycerol stock by placing a small volume of cells onto a MHA plate. The MHA plate was incubated overnight at 37° C. A single colony was subsequently used to inoculate MHB+10 μg/mL kanamycin to obtain a bacterial broth suspension. This was grown in at 37° C. on a rotary shaking incubator (100 rpm) for 12 hours. The bacterial cell concentration was adjusted to ~5×105 colony forming units per milliliter (CFU/mL) in MHB using optical density at 595 nm. Treated cells with polymyxin E (PME) or norfloxacin (in μg/ml) at indicated concentrations for 30 minutes at 37° C. and then added a compound of the disclosure at indicated micromolar concentrations. Incubated for 3.5 hours at 37° C. Cell samples were read on the flow cytometer to detect (green fluorescent) RLU RecA expression and/or shutdown. FIG. 2 shows the effect of treating *E. coli* with PME, norfloxacin, Compound 47, or Compound 49. The data show that the compounds killed *E. coli* and inhibited the SOS response.

Figure 3:
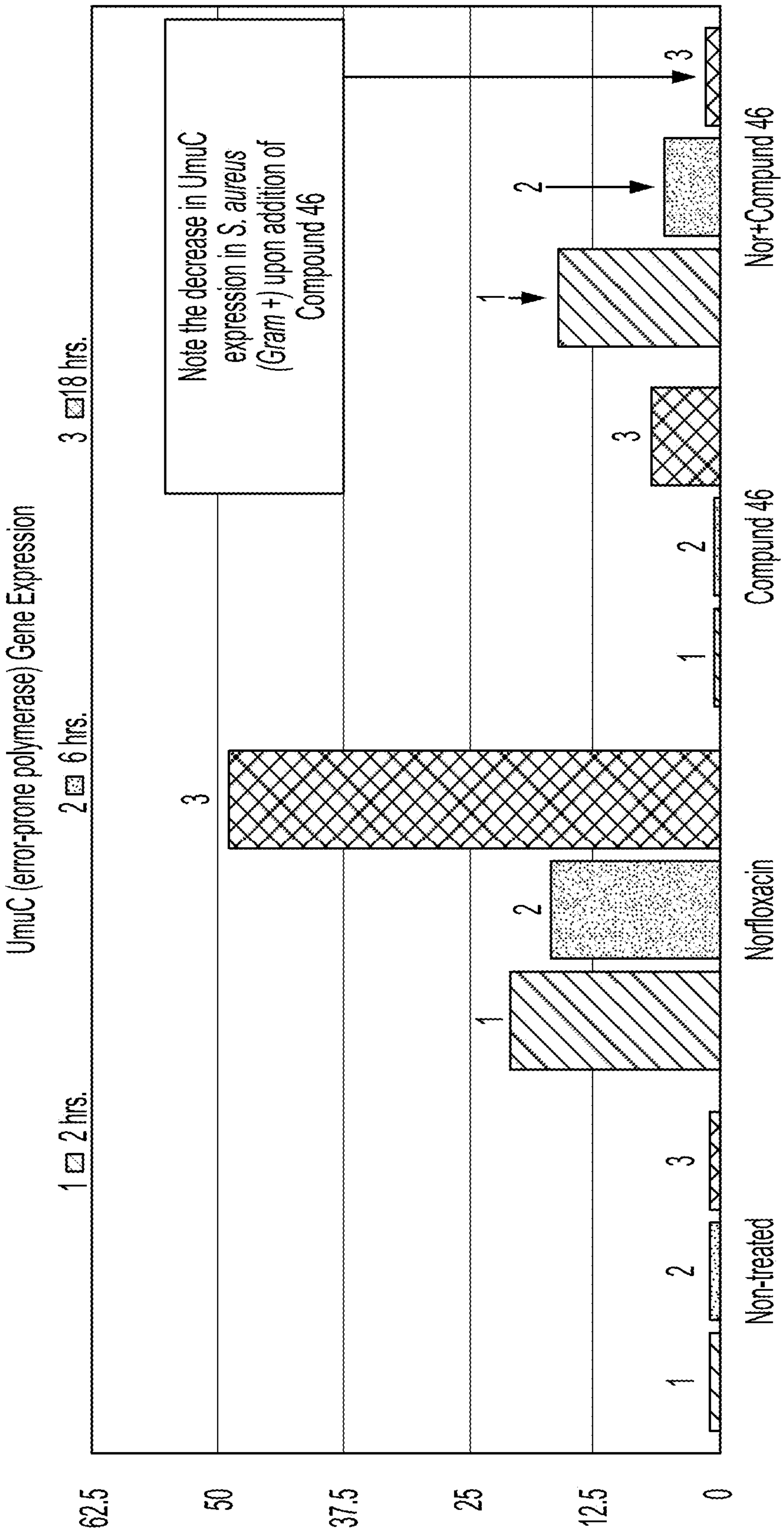
FIG. 3 shows UmuC (error-prone polymerase) Gene expression of *S. aureus* upon treatment with norfloxacin, Compound 46, or norfloxacin and Compound 46.

RecA and error-prone polymerase subunit UmuC transcripts were quantitatively measured using rtPCR in *S. aureus. S. aureus* was challenged with sub-inhibitory concentrations of DNA-damaging norfloxacin. The data demonstrated transcriptional inhibition of the error-prone polymerase component of the SOS-response activating LexA regulon. FIG. 3 shows UmuC (error-prone polymerase) Gene expression of *S. aureus* upon treatment with norfloxacin, Compound 46, or norfloxacin and Compound 46.

Figure 4:
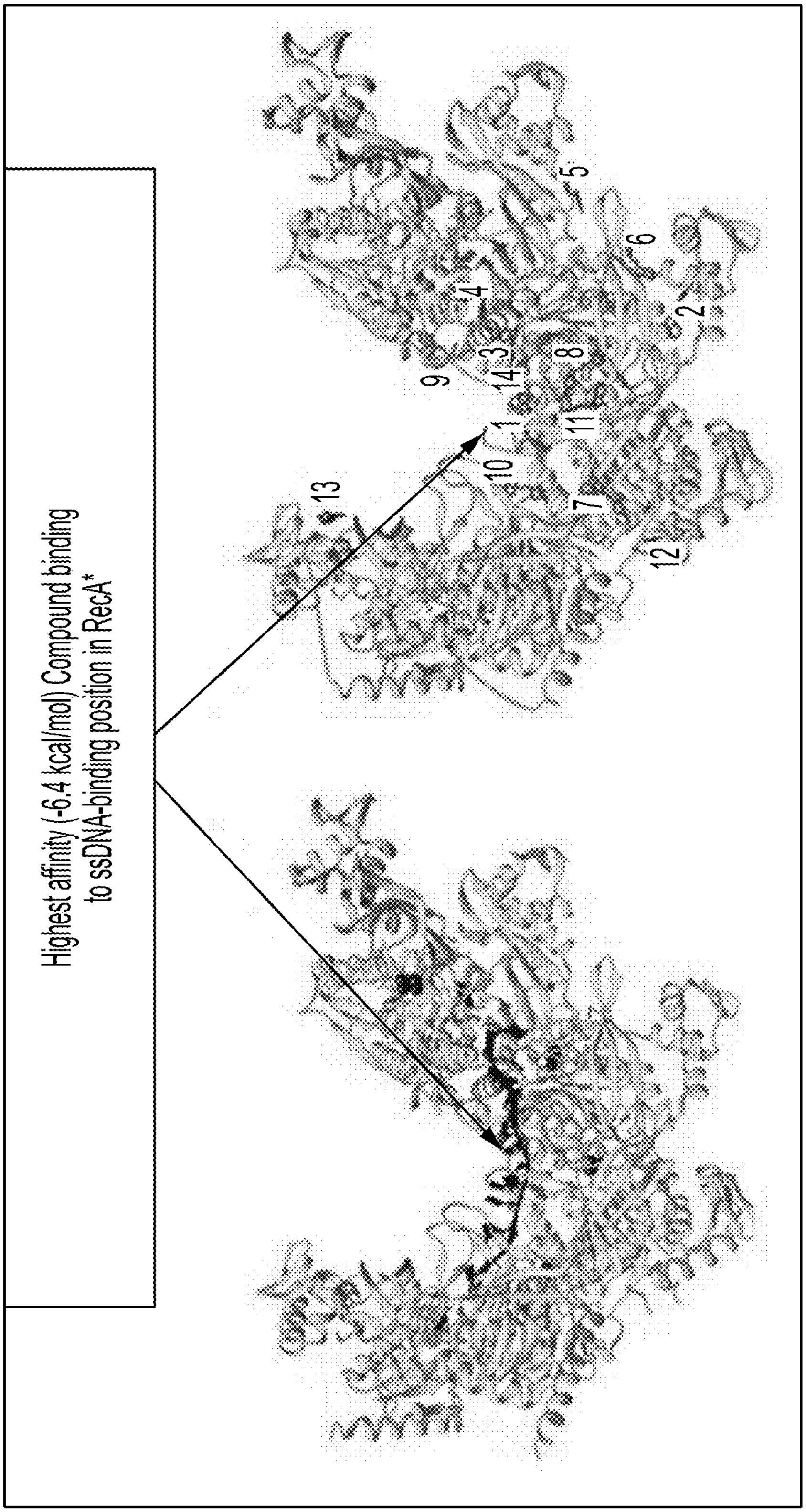
FIG. 4 illustrates results of a docking study showing binding of compounds of the disclosure to the DNA-lesion-activated multimeric RecA (RecA* filament) at the sites where RecA* protein binds the broken ssDNA.

Docking studies showed that compounds of the disclosure bound to the DNA-lesion-activated multimeric RecA (RecA* filament) at the sites where RecA* protein binds the broken ssDNA. This binding interference prevents RecA recognition of the DNA lesion, and as such, prevents activation of LexA-repressed transcription and initiates the overall SOS response. The binding interferences also prevented expression of the error-prone polymerase, mutational recovery did not occur, and resistance to the stressor did not evolve in the presence of compounds of the disclosure. FIG. 4 illustrates results of a docking study showing binding of compounds of the disclosure to the DNA-lesion-activated multimeric RecA (RecA* filament) at the sites where RecA* protein binds the broken ssDNA.

Example 7: Evaluating the Toxicity Profile of Compound 14 on MRSA ATCC BAA-44

MIC data were collected using the method described in EXAMPLE 3 above. The MIC of Compound 14 was between 50 μM and 100 μM.

Figure 9A:
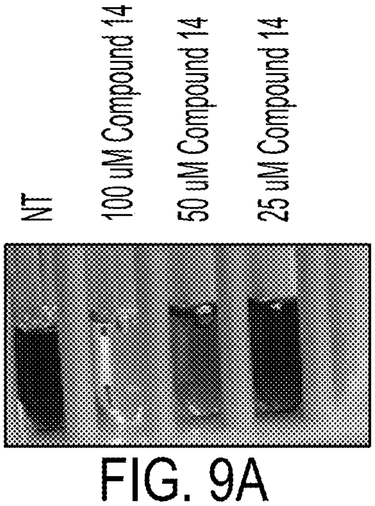
FIG. 9A shows that the minimum inhibitory concentration (MIC) of Compound 14 was between 50 μM and 100 M.
Figure 9B:
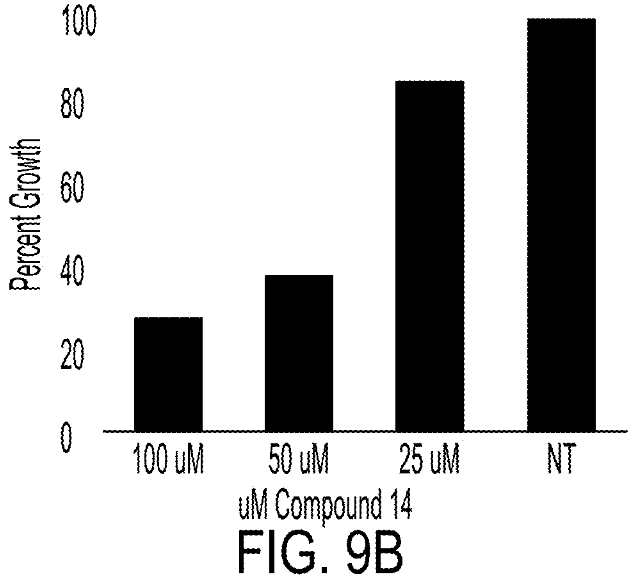
FIG. 9B shows that Compound 14 was toxic to MRSA BAA-44 in the absence of serum.
Figure 9C:
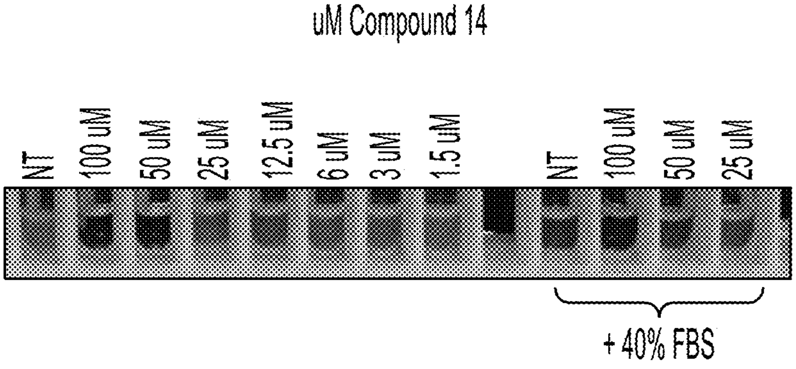
FIG. 9C shows that the MIC of Compound 14 was 50 M in the absence of serum and 100 μM in the presence of 40% FBS.
Figure 10A:
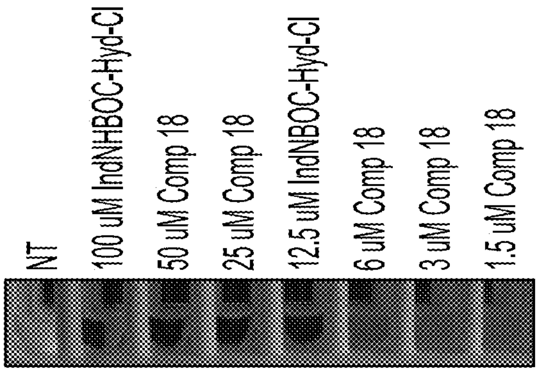
FIG. 10A shows images of experiments used to determine the MIC values of Compound 18.
Figure 10B:
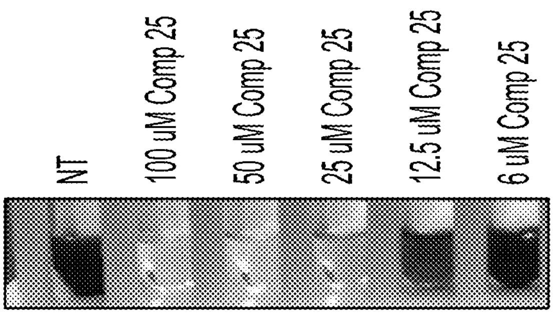
FIG. 10B shows images of experiments used to determine the MIC values of Compound 25.
Figure 10C:
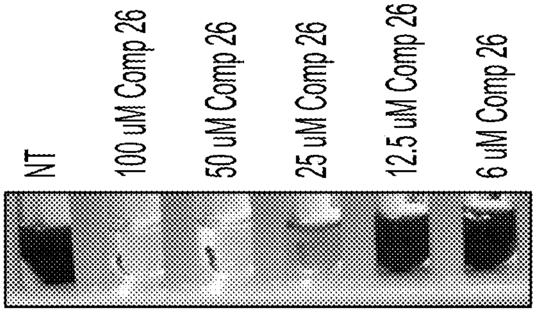
FIG. 10C shows images of experiments used to determine the MIC values of Compound 26.
Figure 10D:
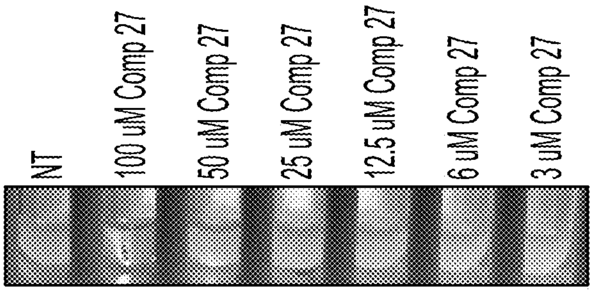
FIG. 10D shows images of experiments used to determine the MIC values of Compound 27.

FIG. 9A shows that the MIC of Compound 14 was between 50 μM and 100 μM. FIG. 9B shows that Compound 14 was toxic to MRSA BAA-44 in the absence of serum. FIG. 9C shows that the MIC of Compound 14 was 50 μM in the absence of serum and 100 μM in the presence of 40% FBS.

Example 8: Direct Activity of Compound 15 on MRSA ATCC BAA-44−/+40% FBS

MIC data were collected using the method described in EXAMPLE 3 above. The MIC of Compound 15 was 50 μM in the absence of serum and >100 μM in the presence of 40% FBS.

Example 9: Effect of Compounds 18, 25, 26, and 27 on MRSA ATCC BAA-44 and *A. baumannii* ATCC 15151

MIC data were collected using the method described in EXAMPLE 3 above. The ATCC BAA-44 MIC of compound 18 was 12.5 M; the MIC of compound 25 was 25 μM; the MIC of compound 26 was 25 μM; and the MIC of compound 27 was 100 μM. FIGS. 10A-10D show images of experiments used to determine the ATCC-BAA-44 MIC values of Compounds 18, 25, 26, and 27, respectively.

Figure 11:
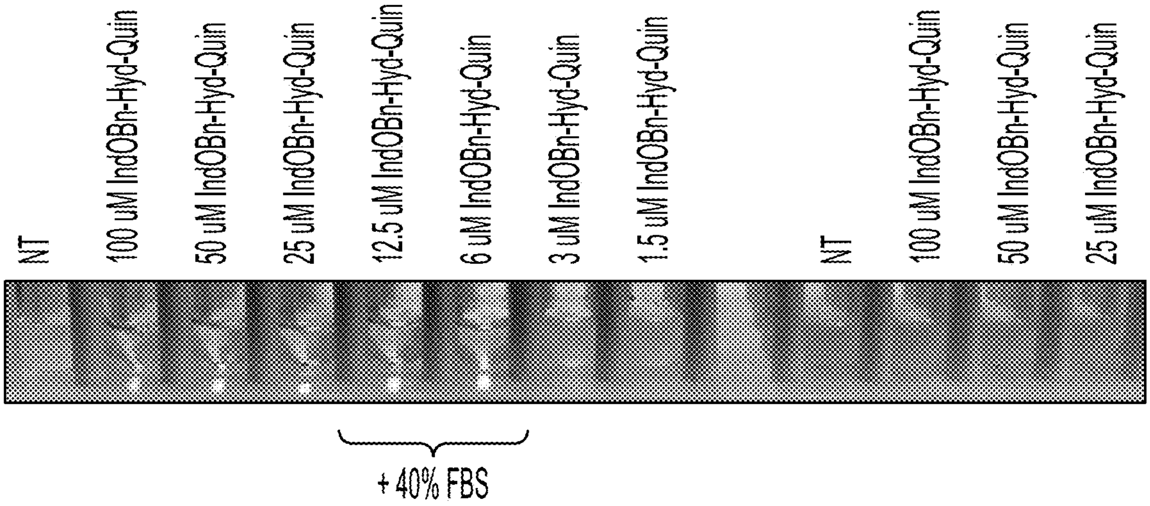
FIG. 11 shows an image from the experiment used to determine the MIC value of Compound 43.

The MIC of Compound 43 was 6 μM in the absence of serum and >100 μM in the presence of 40% FBS. FIG. 11 shows an image from the experiment used to determine the MIC value of Compound 43.

Figure 12A:
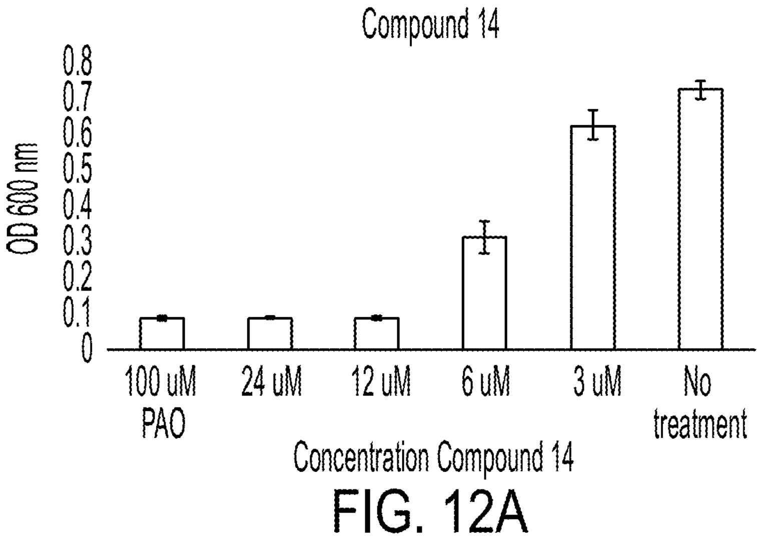
FIGS. 12A-12C show OD data obtained for compounds 14 (FIG. 12A), 25 (FIG. 12B), and 26 (FIG. 12C) used to determined MIC values.
Figure 12B:
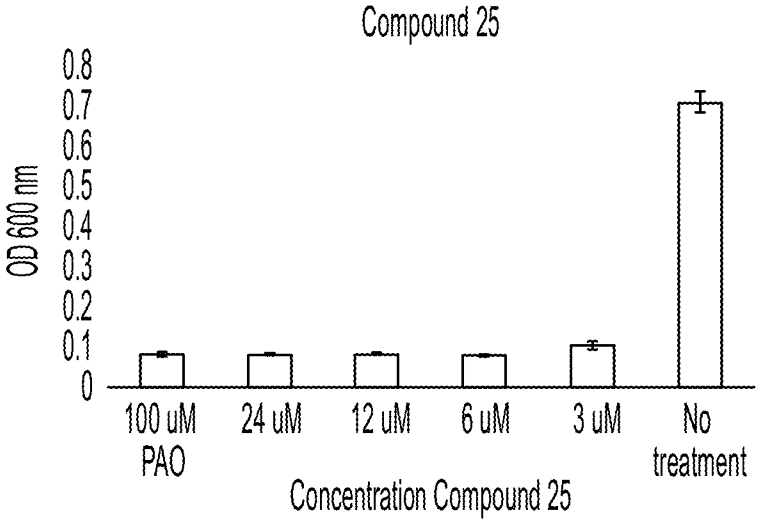
Figure 12C:
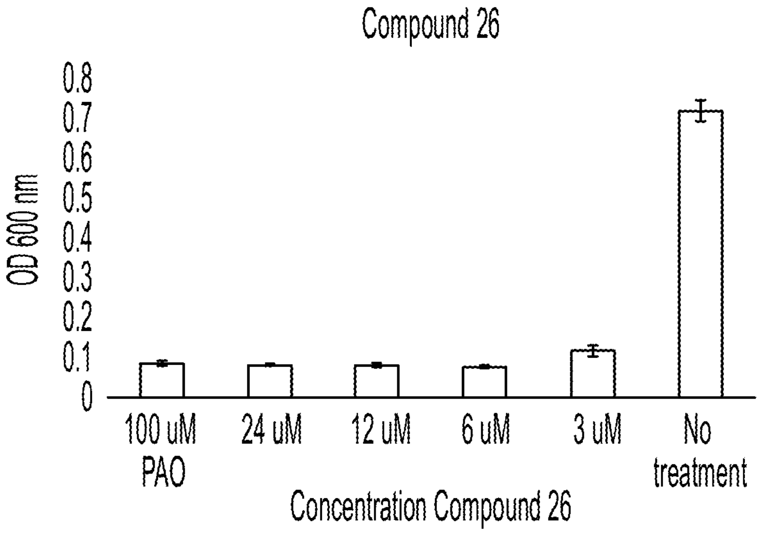

MIC data were collected using the method described in EXAMPLE 3 above. The *A. baumannii* MIC values of compound 14 was 6 μM; the MIC value of compound 15 was 12.5 μM; the MIC value of compound 25 was 3 μM; the MIC value of compound 26 was 3 μM; and the MIC value of compound 27 was 12.5 μM. FIGS. 12A-12C show OD data obtained for compounds 14 (FIG. 12A), 25 (FIG. 12B), and 26 (FIG. 12C) used to determined MIC values.

Figure 13:
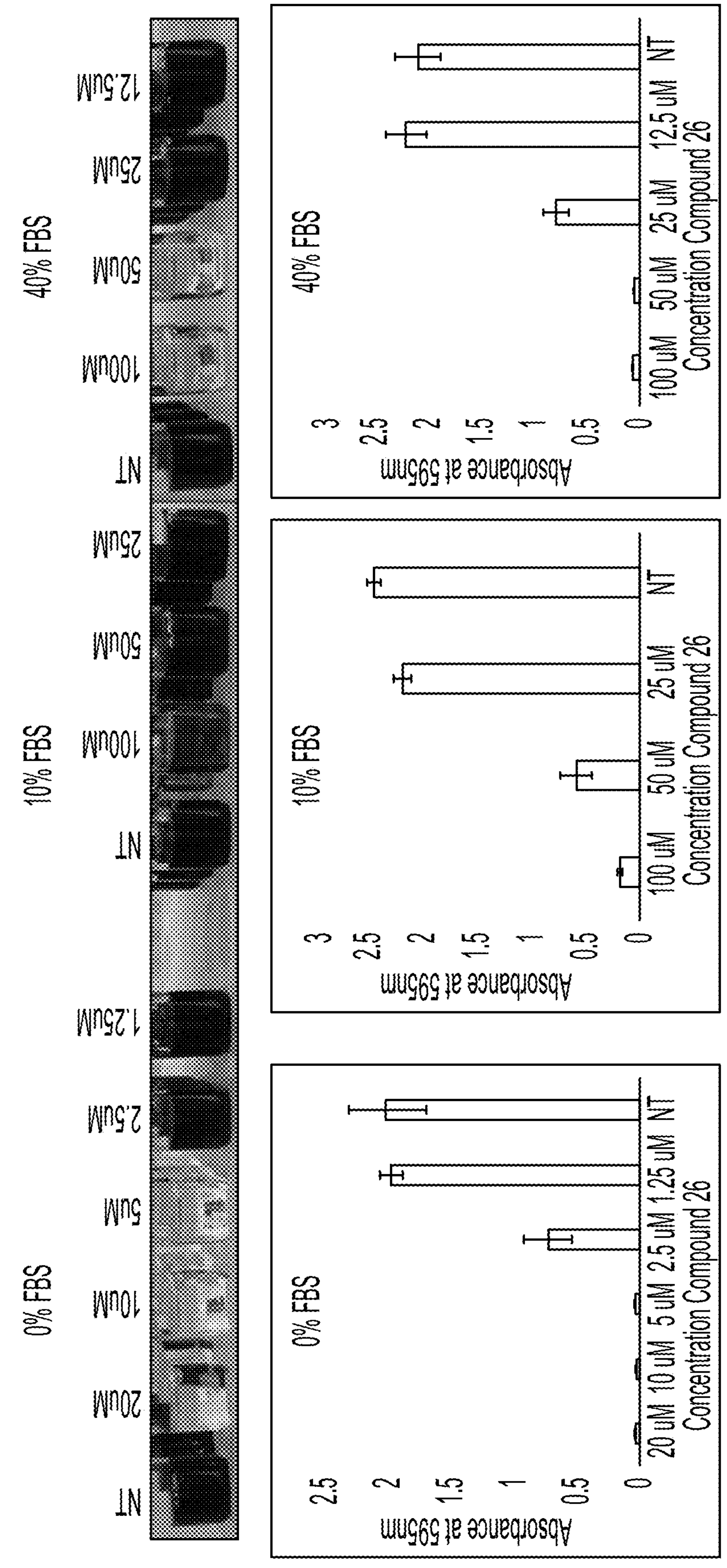
FIG. 13 shows data obtained to determine FBS-concentration-dependent MIC values of Compound 26.

FBS concentration-dependent activity of Compound 26 was determined for *A. baumannii* ATCC BAA-1797. MIC values were obtained using the protocol described in EXAMPLE 3 above. The MIC of Compound 26 in the absence of serum was 5 μM, in the presence of 10% FBS was >100 μM, and in the presence of 40% FBS was 50 μM. FIG. 13 shows data obtained to determine FBS-concentration-dependent MIC values of Compound 26.

Figure 14A:
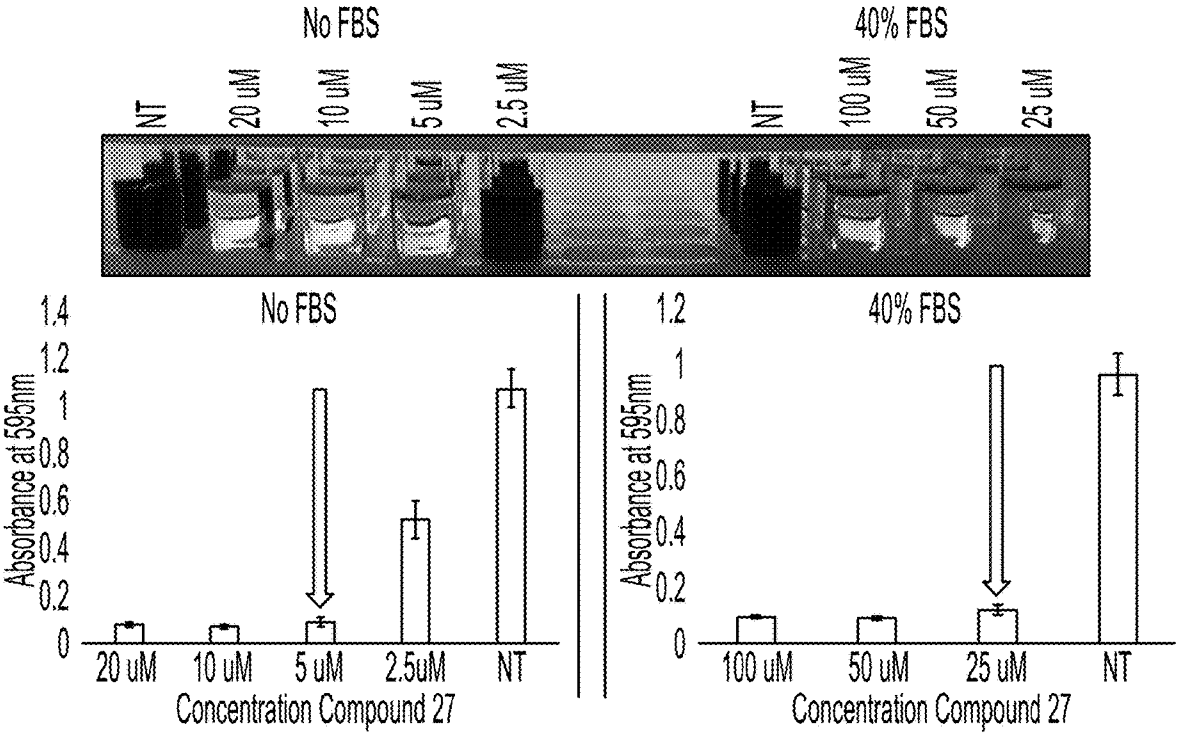
FIGS. 14A and 14B show data obtained to determine the effect of Compounds 27 (FIG. 14A) and 30 (FIG. 14B) on *A. baumannii* ATCC BAA-1797.
Figure 14B:
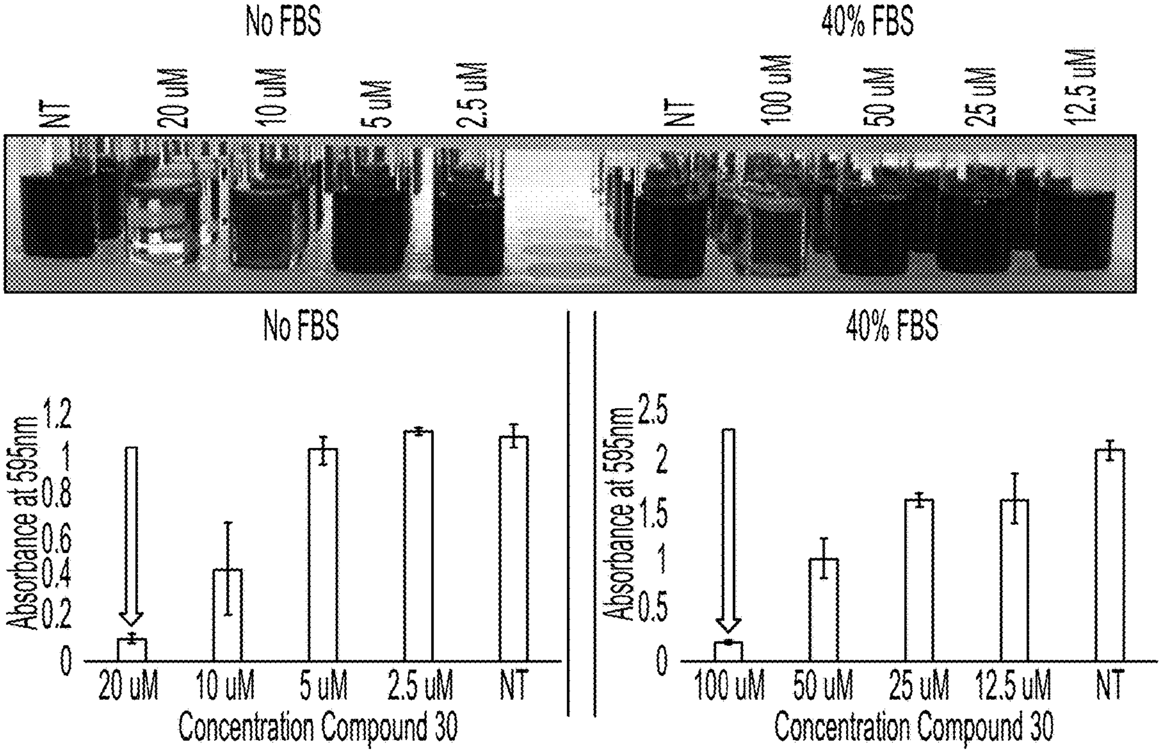

The effects of compounds 15, 27, and 30 on *A. baumannii* ATCC BAA-1797 were determined. MIC values were obtained using the protocol described in EXAMPLE 3 above. The MIC of Compound 15 in the absence of serum was 6 μM and in the presence of 40% FBS was 100 μM. The MIC of Compound 27 in the absence of serum is 5 μM and in the presence of 40% FBS is 25 μM. The MIC of Compound 30 in the absence of serum was 20 μM and in the presence of 40% FBS was 100 μM. FIGS. 14A and 14B show data obtained to determine the effect of Compounds 27 (FIG. 14A) and 30 (FIG. 14B) on *A. baumannii* ATCC BAA-1797.

Figure 15:
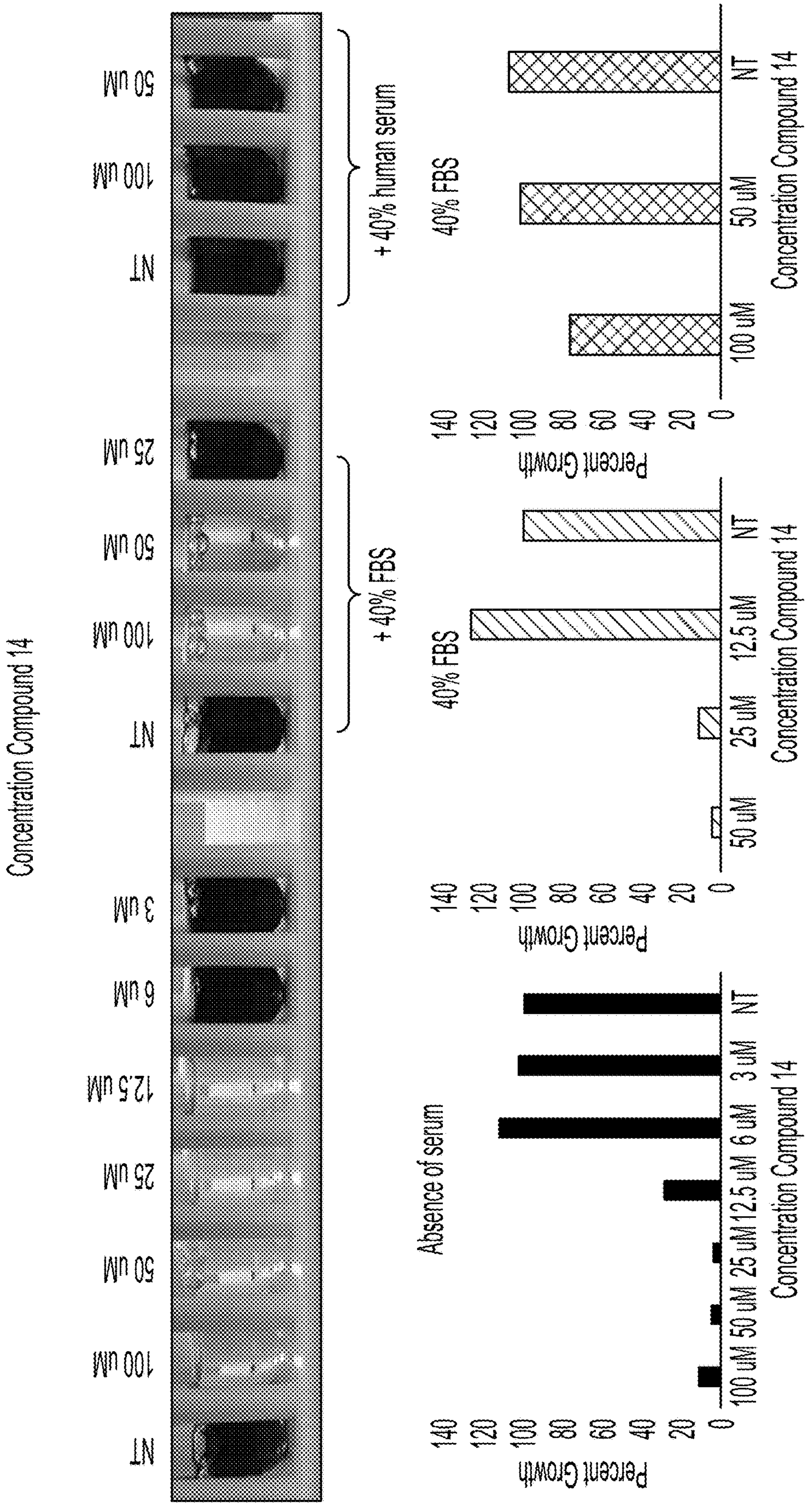
FIG. 15 shows the effects of compound 14 on *A. baumannii* in the absence of serum, 40% FBS, or 40% human serum+MHB.

The effect of compound 14 on *A. baumannii* ATCC BAA-1797 was determined using methods described above. The MIC of Compound 14 in the absence of serum was 12.5 μM, in the presence of 40% FBS was 50 μM, and in the presence of 40% human serum is >100 μM. FIG. 15 shows the effects of compound 14 on *A. baumannii* in the absence of serum, 40% FBS, or 40% human serum+MHB.

The effects of compound 25, 18, and 46 on *A. baumannii* ATCC BAA-1797 in the presence or absence of 40% FBS were determined using methods described above. The MIC of Compound 25 in the absence of serum is 6 μM and in the presence of 40% FBS is <50 μM. The MIC of Compound 18 in the absence of serum is 3 μM and in the presence of 40% FBS is >100 μM. The MIC of Compound 46 in the absence of serum is >100 μM and in the presence of 40% FBS is >100 μM.

Figure 16A:
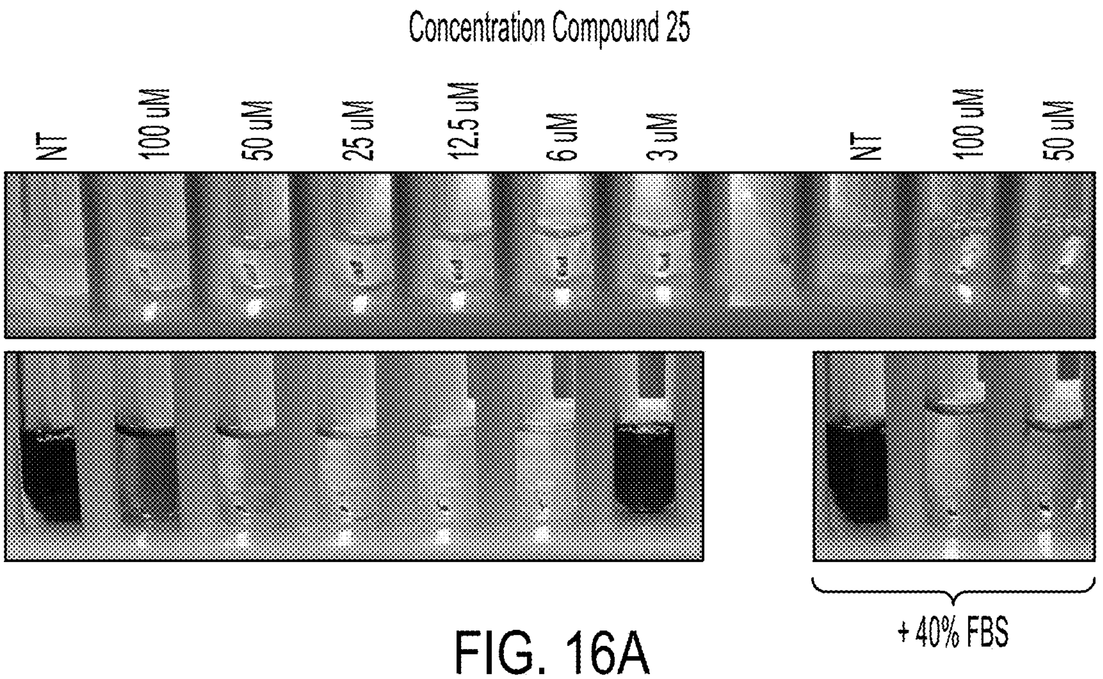
FIG. 16A shows the effects of Compound 25 on *A. baumannii* in the presence or absence of 40% FBS.
Figure 16B:
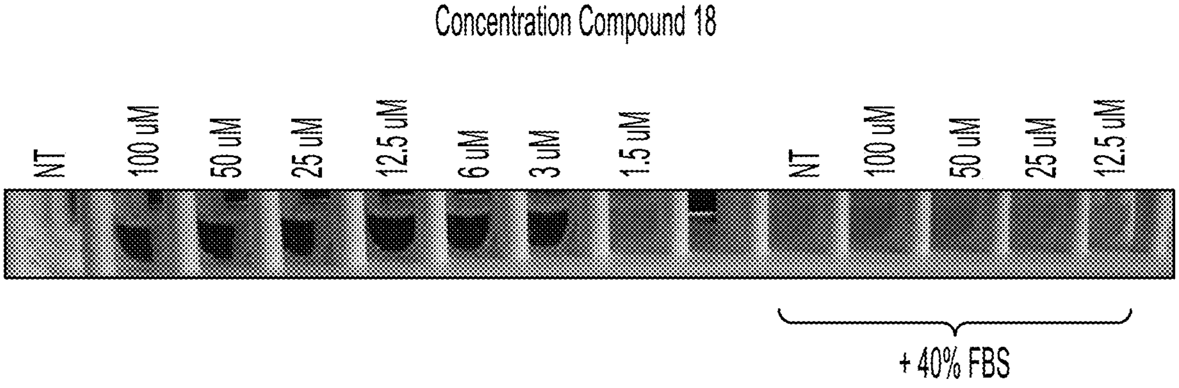
FIG. 16B shows the effects of Compound 18 on *A. baumannii* in the presence or absence of 40% FBS.

FIG. 16A shows the effects of Compound 25 on *A. baumannii* in the presence or absence of 40% FBS. FIG. 16B shows the effects of Compound 18 on *A. baumannii* in the presence or absence of 40% FBS.

TABLE 3 below summarizes the MIC data detailed above.

TABLE 3

| Compound Number | IC50 (μM) in HeLa 10% FBS | MIC (μM) in MDR *A. baumannii* ATCC 1797 0% FBS | 10% FBS | 40% FBS | MIC (μM) in MRSA BAA-44 10% FBS |
|---|---|---|---|---|---|
| 1 | — | 50 | — | — | 1.5 no serum; 12.5 no serum |
| 2 | — | >100 | — | — | >100 |
| 3 | — | >100 | >100 | — | — |
| 5 | — | >100 | >100 | — | — |
| 6 | 0.6 −/+ 0.027 | 25 | >100 | 100 | 25 |
| 7 | 39.6 −/+ 2.1 | 5 | 25 | 50 | 100 |
| 8 | 60.6 −/+ 2.7 | 40 | >100 | 50 | >100 |
| 9 | — | >100 | — | — | — |
| 10 | — | >100 | — | — | 100 in no serum |
| 11 | — | >100 | >100 | >100 | >100 |
| 12 | — | 12.5 | >100 | >100 | 25 (no serum) |
| 13 | — | 5 | 100 | >100 | 100 |
| 14 | 36.7 −/+ 3.8 | 6 | >100 | 50 | — |
| 15 | 20.9 −/+ 1.5 | 12.5 | >100 | 50 | — |
| 16 | 40 −/+ 0.56 | 3 | >100 | >100 | >100 |
| 17 | — | >100 | >100 | >100 | >100 |
| 18 | — | 3 | — | >100 | 12.5 (no serum) |
| 19 | — | >100 | — | >100 | >100 |
| 20 | — | 25 | — | >100 | 25 in no serum; >100in FBS |
| 21 | — | 25 | — | >100 | 25 in no serum; >100in FBS |
| 22 | — | 25 | — | >100 | 25 in no serum; >100in FBS |
| 23 | — | 12.5 | — | <100 in human serum | — |
| 24 | — | <100 | — | >100 | — |
| 25 | 30.4 −/+ 3.3 | 6 | >100 | 50 | 50 no serum |
| 26 | 37.3 −/+ 1.8 | 6 | >100 | 100 | 50 μM no serum |
| 27 | 25.8 −/+ 5.2 | 12.5 | >100 | 50 | 100 no serum |
| 28 | — | 25 | — | 100 | — |
| 29 | — | >100 | — | >100 | — |
| 30 | — | >100 | >100 | >100 | >100 |
| 31 | — | 12.5 | — | — | ~100 |
| 32 | — | >100 | — | — | — |
| 33 | — | >100 | — | >100 | >100 (no serum) |
| 34 | 48.0 −/+ 3.2; 157.4 −/+ 1.6 (40% FBS) | 3 | — | 50 | 25 (no serum) |
| 35 | — | >100 | — | >100 | 50 (no serum) |
| 36 | — | >100 | — | >100 | >100 (no serum) |
| 37 | — | >100 | — | >100 | 12.5 (no serum) |

TABLE 3-continued

| Compound Number | IC50 (μM) in HeLa 10% FBS | MIC (μM) in MDR *A. baumannii* ATCC 1797 0% FBS | 10% FBS | 40% FBS | MIC (μM) in MRSA BAA-44 10% FBS |
|---|---|---|---|---|---|
| 38 | — | >100 | — | >100 | >100 (no serum) |
| 39 | — | >100 | — | >100 | 50 (no serum) |
| 40 | — | >100 | — | >100 | >100 |
| 41 | — | 12.5 | — | >100 | 100 no serum |
| 42 | — | <25 | — | >100 | <25 in no serum; 100 in FBS |
| 43 | — | 6 | — | >100 | 6 in no serum; >100 in 40% FBS |
| 44 | — | <100 | — | | <100 |
| 45 | — | 25 | | 50 | 25 in no serum; >100 in 40% |

Example 10: Colony Counts of *A. Baumannii* ATCC BAA-1797 Treated with 4×MIC of Compound 25, Compound 26, Compound 27, Compound 14, and Compound 15 in Triplicate at 16 Hours Post-Treatment Bacterial cells were treated using methods described above. 500 μL aliquots of the adjusted bacterial cell suspensions were placed into borosilicate glass tubes, where the cell suspensions were treated with 24 μM Compound 25, 24 μM Compound 26, 100 μM Compound 27, 48 μM Compound 14, 100 μM Compound 15, 1 μg/mL PME, 10 μg/mL PME, and 1 mM PAO; all treatments were performed in triplicate. The culture tubes were incubated for 16 hours at 37° C. Colony counts were performed by 10-fold serially diluting the samples into fresh MHB and drip-streaking 10 μL from each dilution series onto MHA. The plates were incubated at 37° C. for 18 hours before the CFU/mL were determined by visual cell counts.

Figure 17:
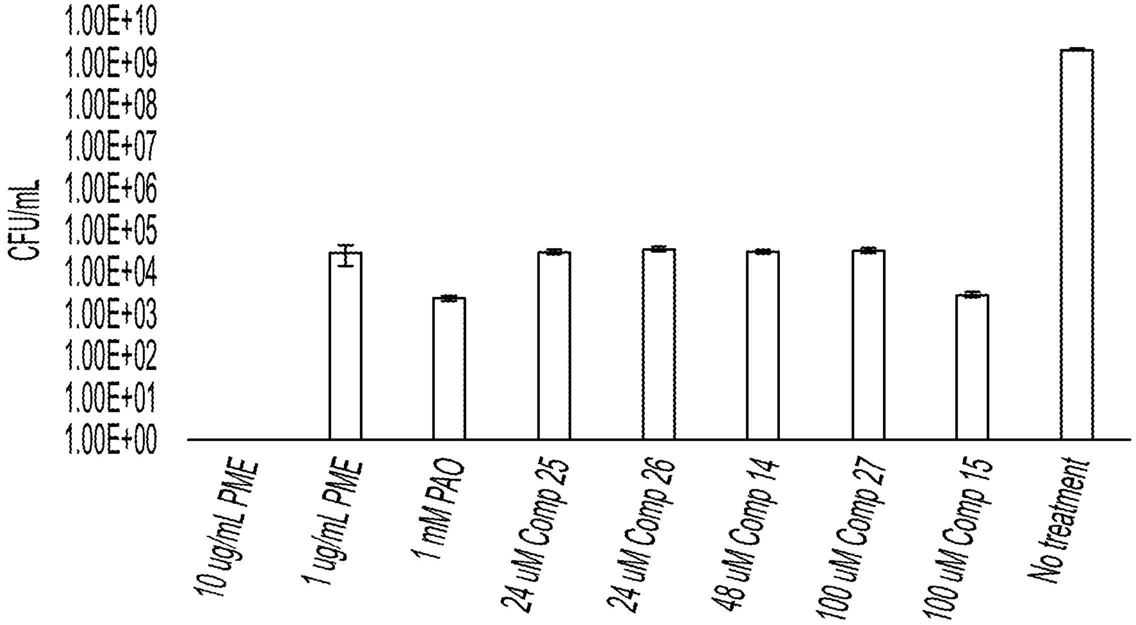
FIG. 17 shows data obtained upon treating *A. baumannii* ATCC BAA-1797 colonies with Compounds 14, 15, 25, 26, 27, PME, or PAO.

Upon treatment with the compounds, 1 μg/mL PME, and PAO, cells were still viable even after 16 hours of treatment. The observation indicated that full cell death required over 16 hours of treatment exposure. 24 μM Compound 25, 24 μM Compound 26, 100 μM Compound 27, 48 μM Compound 14, and 100 μM Compound 15 killed ~5 orders of magnitude *A. baumannii* ATCC BAA-1797. FIG. 17 shows data obtained upon treating *A. baumannii* ATCC BAA-1797 colonies with Compounds 14, 15, 25, 26, 27, PME, or PAO.

Example 11: Effect of Compound 25 on a Panel of Drug-Resistant *A. Baumannii* Strains Obtained from the CDC and Prevention Antimicrobial Isolate Bank TABLE 4 shows the effect of Compound 25 on a panel of drug-resistant *A. baumannii* strains obtained from the CDC and Prevention Antimicrobial Isolate Bank.

TABLE 4

| AR bank # | Resistance Mechanisms | Biosample accession # | Compound 25 MIC (μM) |
|---|---|---|---|
| 33 | NDM-1, OXA-94, sul2 | SAMN04014874 | 6 |
| 35 | ADC-25, aph(3')-Ic, mph(E), msr(E), OXA-66, OXA-72, strA, strB, sul2, TEM-1D | SAMN04014876 | 12.5 |
| 36 | OXA-24, OXA-65, strA, strB, sul2 | SAMN04014877 | 12.5 |
| 37 | NDM-1, OXA-94, sul2 | SAMN04014878 | 6 |
| 45 | aac(3)-Ia, aph(3')-Ic, catA1, OXA-23, OXA-69, TEM-ID, tet(A) | SAMN04014886 | 6 |
| 52 | OXA-100, OXA-58, sul2 | SAMN04014893 | 6 |
| 56 | aac(3)-IIa, aph(3')-Ic, mph(E), msr(E), OXA-23, OXA-66, strA, strB, sul2 | SAMN04014897 | 3 |
| 63 | OXA-23, OXA-24, OXA-65, sul2 | SAMN04014904 | 3 |
| 70 | OXA-100, OXA-58, sul2 | SAMN04014911 | 3 |
| 78 | aac(3)-IIa, aadA11, ADC-25, dfrB1, mph(E), msr(E), OXA-71, SHV-5, sul1 | SAMN04014919 | 6 |
| 83 | aph(3')-Ic, armA, ARR-3, cmlA1, dfrA1, mph(E), msr(E), NDM-1, OXA-23, OXA-69, PER-7, strA, sul1, sul2, tet(B) | SAMN04014924 | 3 |
| 88 | aac(3)-IIa, NDM-1, OXA-64, strA, strB, sul2, tet(B) | SAMN04014929 | 6 |
| 101 | OXA-24, OXA-65, strA, strB, sul2 | SAMN04014942 | 6 |
| 102 | ADC-25, armA, catB8, mph(E), msr(E), OXA-66, strA, strB, sul1 | SAMN04014943 | 6 |

Example 12: Effect of Compound 25, Compound 26, Compound 27, Compound 14, and Compound 15 on *A. baumannii* CDC AR033 and AR083

Bacterial cells were prepared using methods descried above. 500 μL aliquots of the adjusted bacterial cell suspensions were placed into borosilicate glass tubes, where the cell suspensions were treated with 100 μM Compound 25, Compound 26, Compound 27, Compound 14, and Compound 15. The treatments were serially diluted two-fold. The culture tubes were incubated for 18 hours at 37° C. The MIC values for AR033 were as follows: Compound 25=6 M; Compound 26=6 M; Compound 27=25 μM; Compound 14=25 μM; Compound 15=25 μM. The MIC values for AR083 were as follows: Compound 25=<3 μM; Compound 26=6 M; Compound 27=12.5 μM; Compound 14=12.5 M; Compound 15=12.5 μM.

Example 13: Synergistic Effects of Kanamycin and Compound 25 on *A. Baumannii* ATCC 15151

Bacterial cells were prepared using methods described above. 500 μL aliquots of the adjusted bacterial cell suspensions were placed into borosilicate glass tubes, where the cell suspensions were treated with 12.5 μg/mL kanamycin, 1 μM or 2 μM Compound 25, or a combination of 12.5 μg/mL kanamycin plus 1 μM or 2 μM Compound 25. The culture tubes were incubated for 18 hours at 37° C. Colony counts were performed by 10-fold serially diluting the samples into fresh MHB and drip-streaking 10 μL from each dilution series onto MHA. The plates were incubated at 37° C. for 18 hours before the CFU/mL were determined by visual cell counts.

Figure 18:
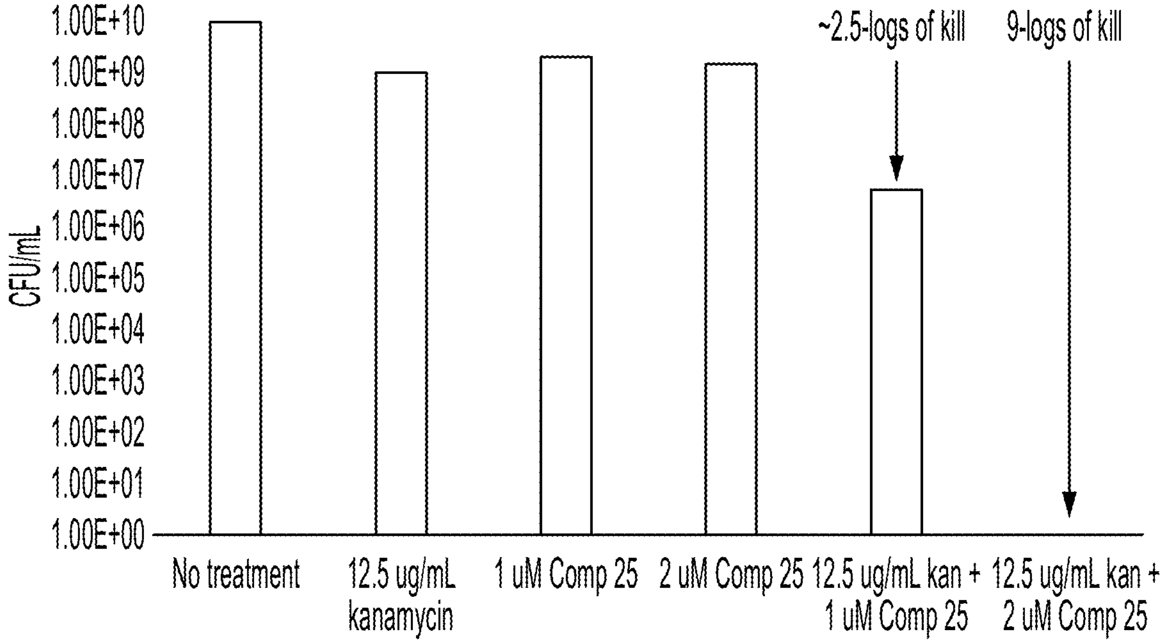
FIG. 18 shows the synergistic effects of kanamycin and compound 25 on *A. baumannii* ATCC 15151.

Treatment of cells with 12.5 μg/mL kanamycin+1 μM Compound 25 resulted in synergy with 2.5 logs of kill, and treatment with 12.5 μg/mL kanamycin+2 μM Compound 25 resulted in synergy with full cell death equal to 9 orders of magnitude. FIG. 18 shows the synergistic effects of kanamycin and compound 25 on *A. baumannii* ATCC 15151.

The synergistic effect of kanamycin and Compound 25 on *A. baumannii* ATCC 15151 in the presence of absence of FBS was also studied. *A. baumannii* ATCC 15151 was grown from a glycerol stock by placing a small volume of cells onto a MHA plate. The MHA plate was incubated overnight at 37° C. A single colony was subsequently used to inoculate MHB to obtain a bacterial broth suspension. The MHB broth suspension was grown at 37° C. on a rotary shaking incubator (100 rpm) for 12 hours. The bacterial cell concentration was adjusted to ~$5\times10^5$ CFU/mL in MHB or MHB+40% FBS using OD at 595 nm. 500 μL aliquots of the adjusted bacterial cell suspensions were placed into borosilicate glass tubes. Cell suspensions were treated with 6 μg/mL or 12.5 μg/mL kanamycin, 1 μM, 2 μM, or 10 μM Compound 25, or a combination of 6 μg/mL or 12.5 μg/mL gentamicin plus 1 μM, 2 μM, or 10 μM Compound 25. The culture tubes were incubated for 18 hours at 37° C. Colony counts were determined by 10-fold serially diluting the samples into fresh MHB and drip-streaking 10 μL from each dilution series onto MHA. The plates were incubated at 37° C. for 18 hours before the CFU/mL were determined by visual cell counts.

Figure 19A:
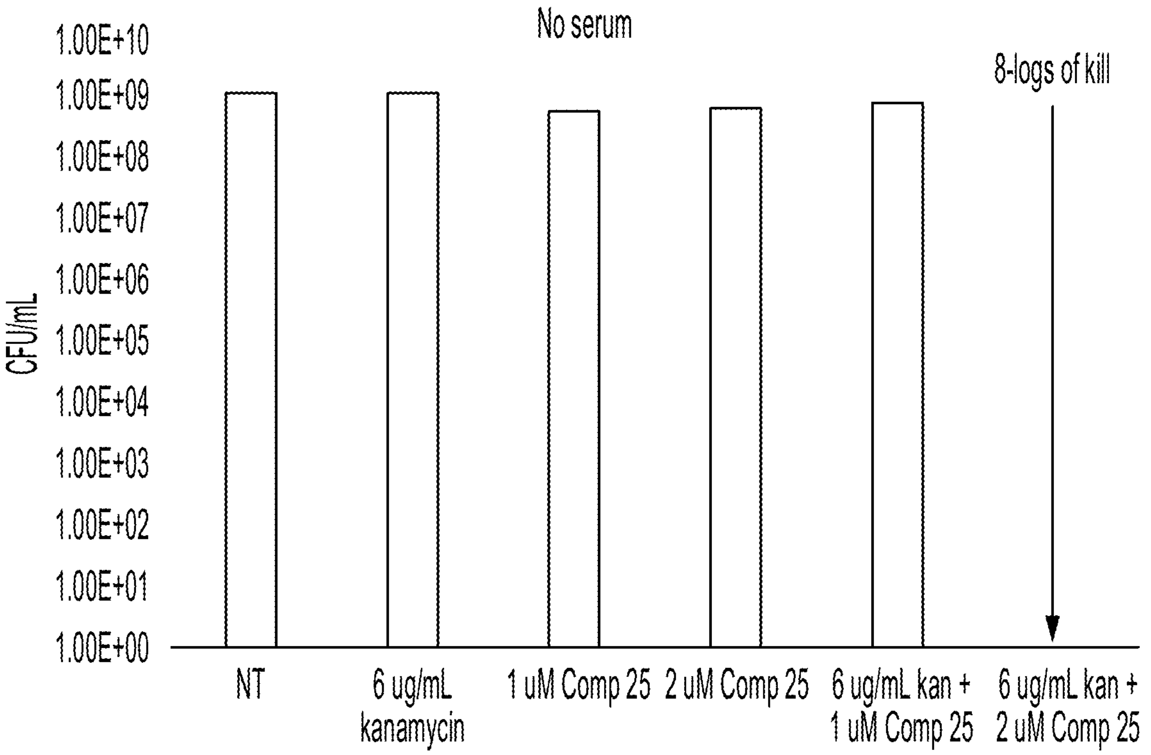
FIGS. 19A and 19B show the synergistic effects of kanamycin and compound 25 on *A. baumannii* ATCC 15151 in the presence (FIG. 19A) or absence (FIG. 19B) of 40% FBS.
Figure 19B:
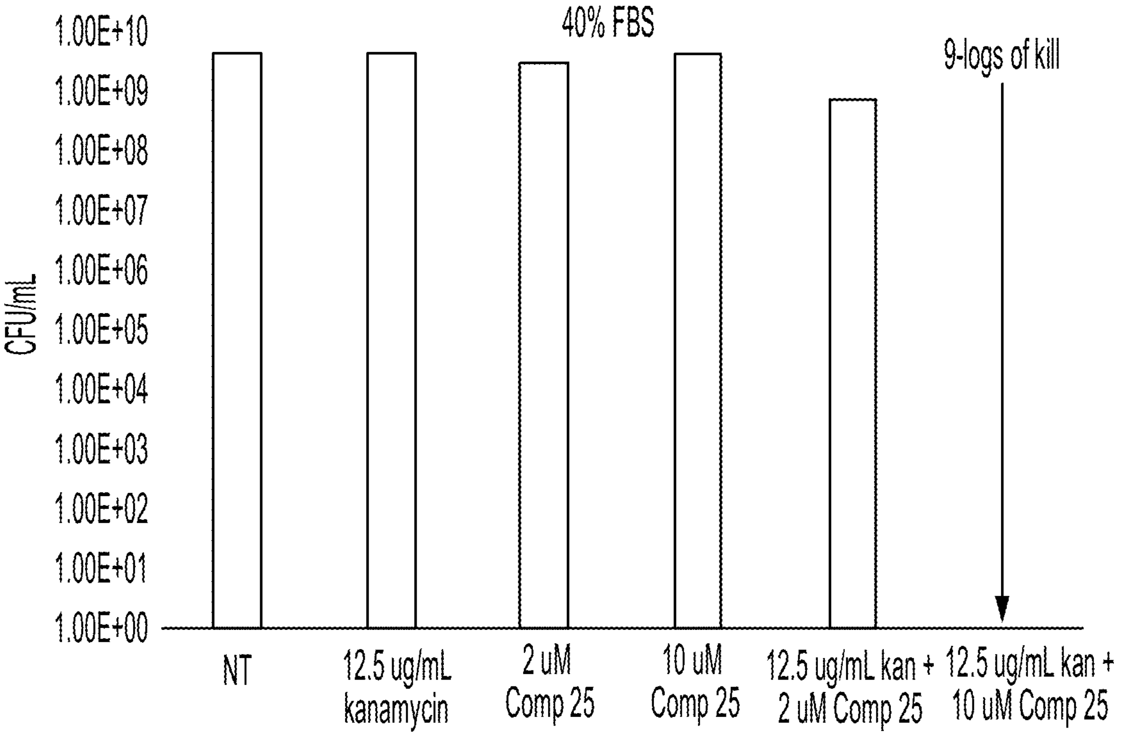

In cell suspensions treated without serum, synergy between 6 μg/mL kanamycin+2 μM Compound 25 equaled 8-logs of kill. In cell suspensions treated with 40% FBS, synergy between 12.5 μg/mL kanamycin+10 μM Compound 25 equaled 9-logs of kill. FIGS. 19A and 19B show the synergistic effects of kanamycin and compound 25 on *A. baumannii* ATCC 15151 in the presence (FIG. 19A) or absence (FIG. 19B) of 40% FBS.

Example 14: Effect of Gentamicin and Compound 25 on *A. Baumannii* ATCC BAA-1797

Cells were cultured using methods described above. 500 μL of the adjusted bacterial cell suspensions were placed into borosilicate glass tubes, where the cell suspensions were treated with 100 μg/mL gentamicin, 2 μM Compound 25, or a combination of 100 μg/mL gentamicin plus 2 μM Compound 25. The culture tubes were incubated for 18 hours at 37° C. Colony counts were performed by 10-fold serially diluting the samples into fresh MHB and drip-streaking 10 μL from each dilution series onto MHA. The plates were incubated at 37° C. for 18 hours before the CFU/mL were determined by visual cell counts.

Figure 20A:
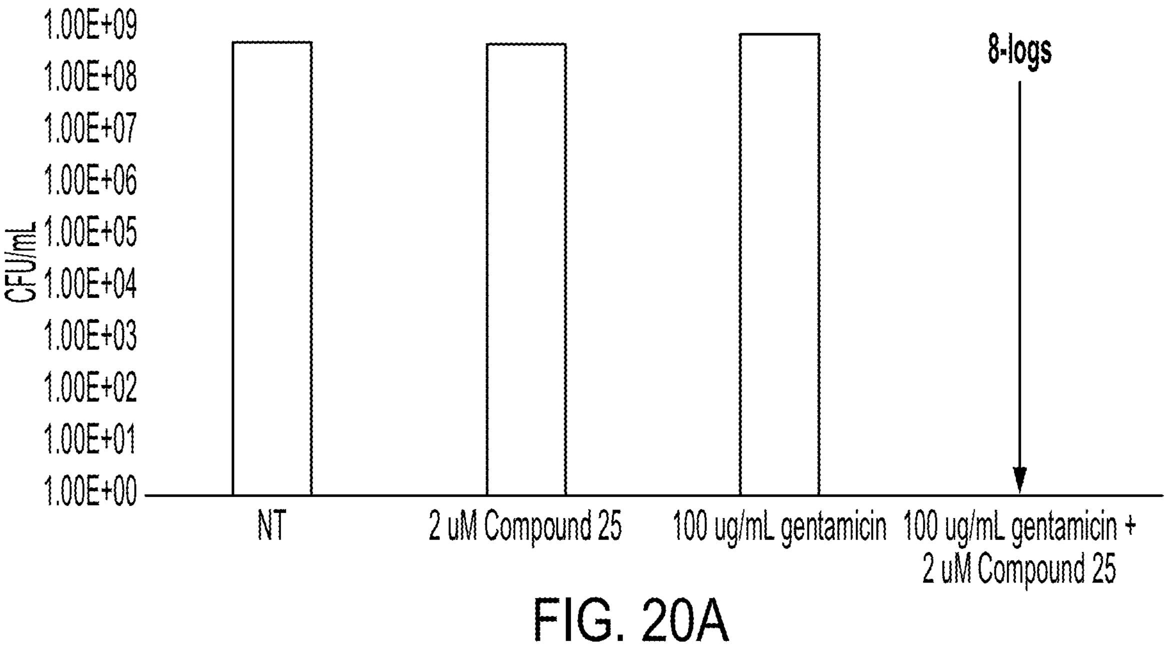
FIG. 20A shows the effect of treating *A. baumannii* ATCC BAA-1797 with 100 μg/mL gentamicin, 2 μM compound 25, or 100 μg/mL gentamicin and 2 μM compound 25.

Treatment of cell suspensions with 100 μg/mL gentamicin+2 μM Compound 25 resulted in remarkable synergy with full cell death equal to 8 orders of magnitude. FIG. 20A shows the effect of treating *A. baumannii* ATCC BAA-1797 with 100 μg/mL gentamicin, 2 μM compound 25, or 100 μg/mL gentamicin and 2 μM compound 25.

Figure 20B:
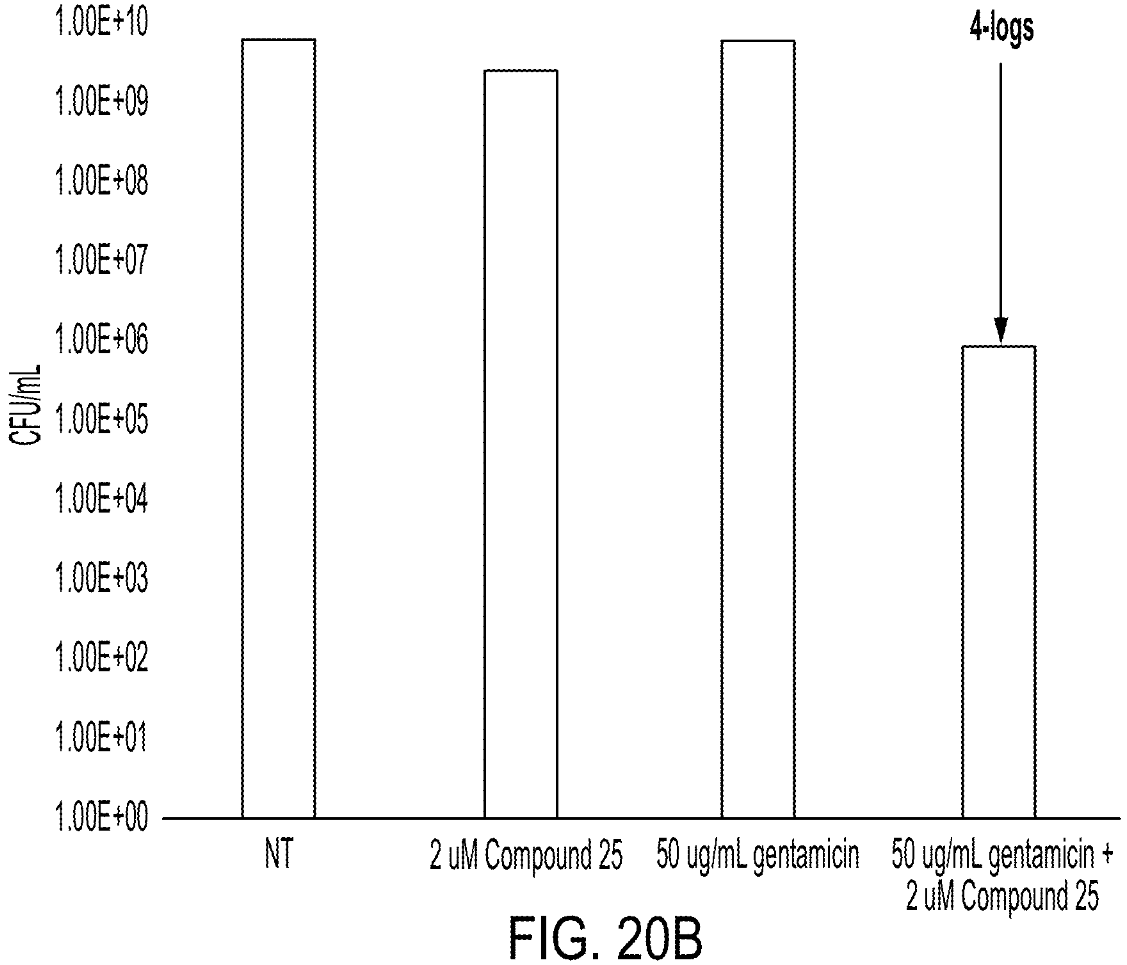
FIG. 20B shows the effect of treating *A. baumannii* ATCC BAA-1797 with 50 μg/mL gentamicin, 2 μM compound 25, or 50 μg/mL gentamicin and 2 μM compound 25.

500 μL aliquots of the adjusted bacterial cell suspensions were placed into borosilicate glass tubes, where the cell suspensions were treated with 50 μg/mL gentamicin, 2 μM Compound 25, or a combination of 50 μg/mL gentamicin plus 2 μM Compound 25. The culture tubes were incubated for 18 hours at 37° C. 50 μg/mL gentamicin+2 μM Compound 25 resulted in synergy with full cell death equal to 4 orders of magnitude. FIG. 20B shows the effect of treating *A. baumannii* ATCC BAA-1797 with 50 μg/mL gentamicin, 2 μM compound 25, or 50 μg/mL gentamicin and 2 μM compound 25.

Example 15: Nitrocefin β-Lactamase Assay on *E. coli* pNMT41 Treated with 10 μg/mL Melittin 6 μM, 12 μM, 24 μM, and 100 μM Compound 25, and 10 μg/mL PME: No Membrane Disruption

Figure 21:
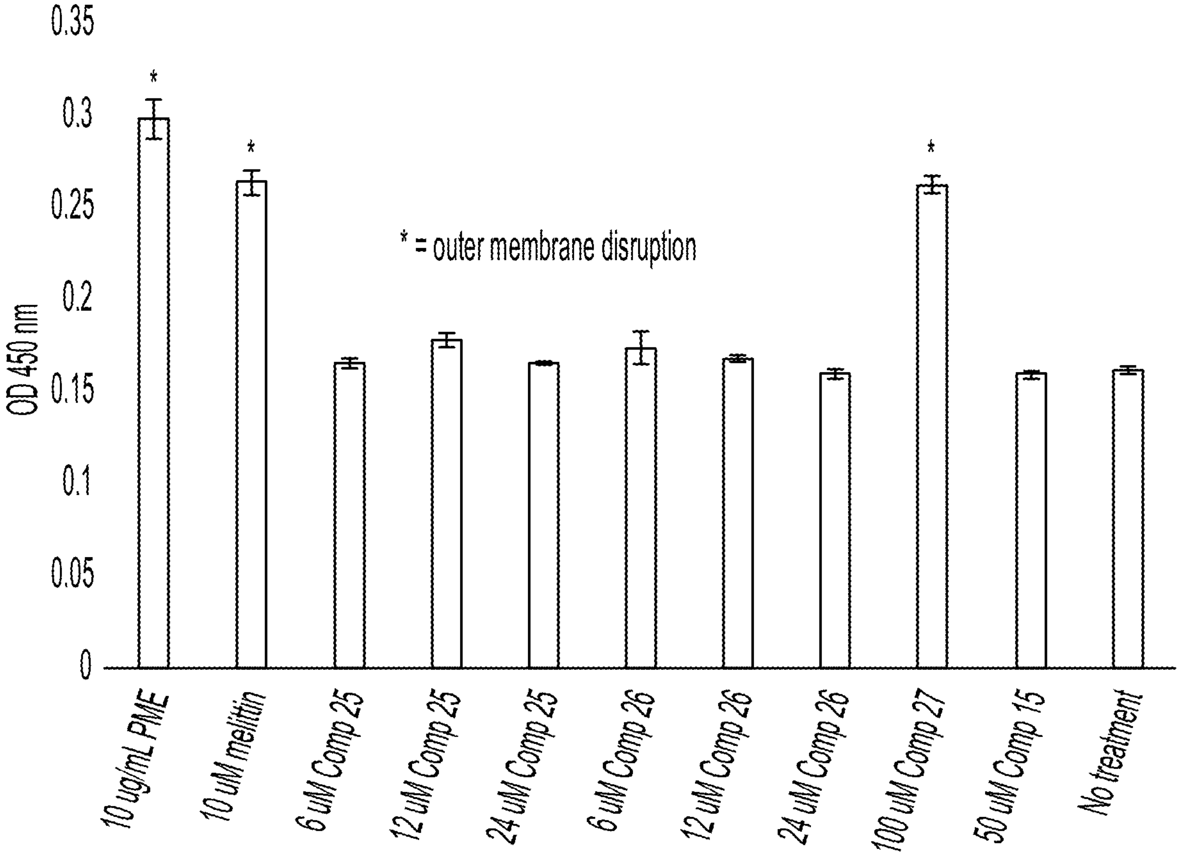
FIG. 21 shows the effect of *E. coli* pNMT41 treated with 10 μg/mL melittin 6, 12, 24, and 100 μM Compound 25, and 10 μg/mL PME.

*E. coli* pUC18 was grown from a glycerol stock by placing a small volume of cells onto a MHA plate. The MHA plate was incubated overnight at 37° C. A single colony was subsequently used to inoculate MHB+100 μg/mL ampicillin to obtain a bacterial broth suspension. The MHB broth suspension was grown at 37° C. on a rotary shaking incubator (100 rpm) for 12 hours. The cells were washed 3× by centrifuging and washing with 1 mL medium 200. The washed bacterial cell concentration was adjusted to ~$1\times10^7$ CFU/mL in medium 200 using OD at 595 nm. The cells were treated cells with 10 μM melittin; 6, 12, 24 μM Compound 25; 6 μM, 12 μM, 24 μM Compound 26; 100 μM Compound 27; 50 μM Compound 15; and 10 μg/mL PME. The cells were incubated at 37° C. for 30 minutes; added 50 μM nitrocefin and incubated 10 minutes at 37° C.

pUC18 *E. coli* carry an ampicillin resistance gene and produce β-lactamase. Cells treated with melittin and PME had a high concentration of β-lactamase in the supernatant (indicated by the orange-red product of the reaction with nitrocefin) due to melittin's and PME's potent membrane activity, thus causing leakage of β-lactamase from within the periplasmic space. The compounds of the disclosure did not disrupt the outer membrane (indicated by no color change), with the exception of Compound 27 which caused outer membrane disruption. FIG. 21 shows the effect of *E. coli* pNMT41 treated with 10 μg/mL melittin 6, 12, 24, and 100 μM Compound 25, and 10 μg/mL PME.

Example 16: 6-Chloro-4-Methyl-Umbelliferyl-β-D-Glucuronide Assay for Beta-Glucuronidase on *E. coli* pNMT41 Treated with Melittin, 6 μM, 12 μM, 24 μM, and 100 μM Compound 25 and PME: Inner Membrane Disruption

Figure 22A:
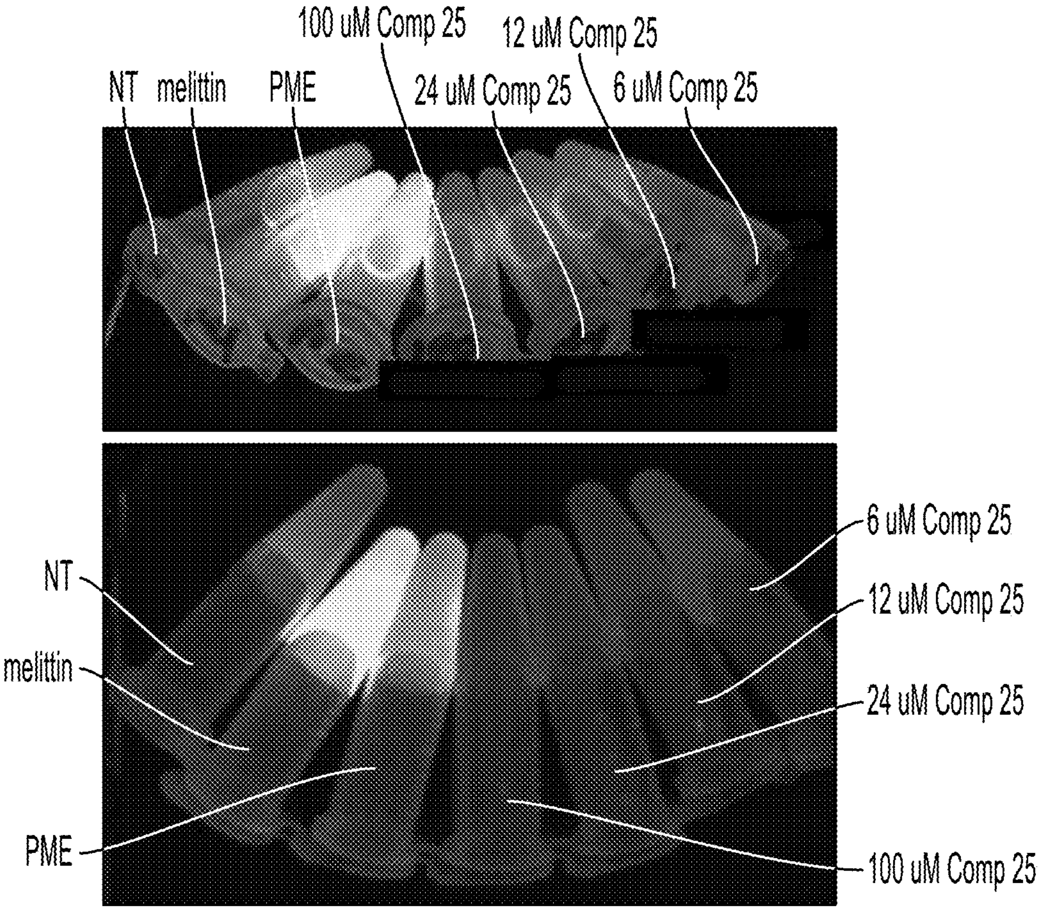
FIG. 22A shows the effects of treating *E. coli* pNMT41 with 10 μM melittin (disrupts PM), 6, 12, 24, and 100 μM Compound 25 and 10 μg/mL PME.

*E. coli* pNMT 41 was grown from a glycerol stock by placing a small volume of cells onto a MHA plate. The MHA plate was incubated overnight at 37° C. A single colony was subsequently used to inoculate MHB+100 μg/mL ampicillin to obtain a bacterial broth suspension. The MHB broth suspension was grown at 37° C. on a rotary shaking incubator (100 rpm) for 12 hours. The bacterial cell concentration was adjusted to ~$1\times10^7$ CFU/mL in MHB using OD at 595 nm. The cells were washed 3× by spinning by centrifuge and washing with 500 μL medium 200. The cells were resuspended in 7 mL medium 200. The cells were treated with 10 μM melittin, 6, 12, 24, and 100 μM Compound 25, and 10 μg/mL PME. The cells were incubated at 37° C. for 30 minutes. 1 μM umbelliferyl was added, and the cells were incubated further for 10 minutes at 37° C.

pNMT41 are producing GUS, and given that pNMT cells treated with 10 μM melittin and 10 μg/mL PME are positively expressing GUS from addition of umbelliferyl and subsequent fluorescence, this result shows that while PME and melittin disrupt inner membrane, Compound 25 did not disrupt the inner membrane. FIG. 22A shows the effects of treating *E. coli* pNMT41 with 10 μM melittin (disrupts PM), 6, 12, 24, and 100 μM Compound 25 and 10 μg/mL PME.

Figure 22B:
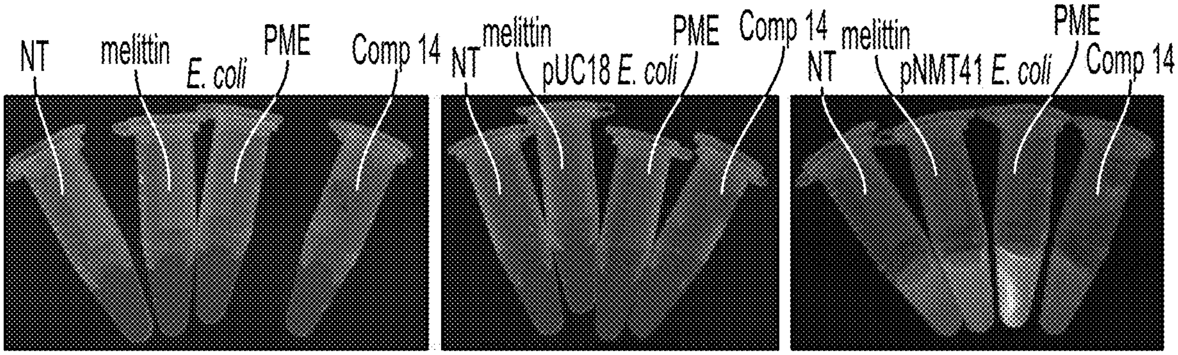
FIG. 22B shows the effects of treating *E. coli* pNMT41 with 1 μM melittin (disrupts inner membrane), 12.5 μM of compound 14 and 10 μg/mL PME.

In a separate experiment, cells were resuspended in medium 200 and treated with 1 μM melittin, 12.5 μM Compound 14, or 10 μg/mL PME. The cells were then incubated at 37° C. for 45 minutes. 1 μM umbelliferyl was added, and the cells were incubated further for 10 minutes at 37° C.

pNMT41 are producing GUS, and given that pNMT cells treated with 10 μM melittin and 10 μg/mL PME are positively expressing GUS from addition of umbelliferyl and subsequent fluorescence, this result shows that PME also disrupts inner membrane. Compound 14 did not disrupt inner membrane. FIG. 22B shows the effects of treating *E. coli* pNMT41 with 1 μM melittin (disrupts inner membrane), 12.5 μM of compound 14 and 10 μg/mL PME.

Example 17: Melittin, PME, Compound 47, Compound 48, Compound 49, Compound 25, Compound 26, Compound 27, Compound 14, and Compound 15 on *A. Baumannii* ATCC BAA-1797: PI Membrane Permeability

*A. baumannii* cells were cultured using the methods described above. Cells were treated with 10 μg/mL PME, 10 μg/mL melittin, 1 mM PAO, 100 μM Compound 47, 100 μM Compound 48, 100 μM Compound 49, 6 μM and 24 μM Compound 25. 6 μM and 24 M Compound 26, 25 μM and 100 μM Compound 27, 12.5 μM and 50 μM Compound 14, and 12.5 μM and 50 μM Compound 15. 1:1000 of 18 mM stock PI (18 μM PI final) was added, and the cells were incubated further for 15 minutes at 37° C. The cells were fixed with 2.5% final paraformaldehyde and read on a flow cytometer.

Figure 23:
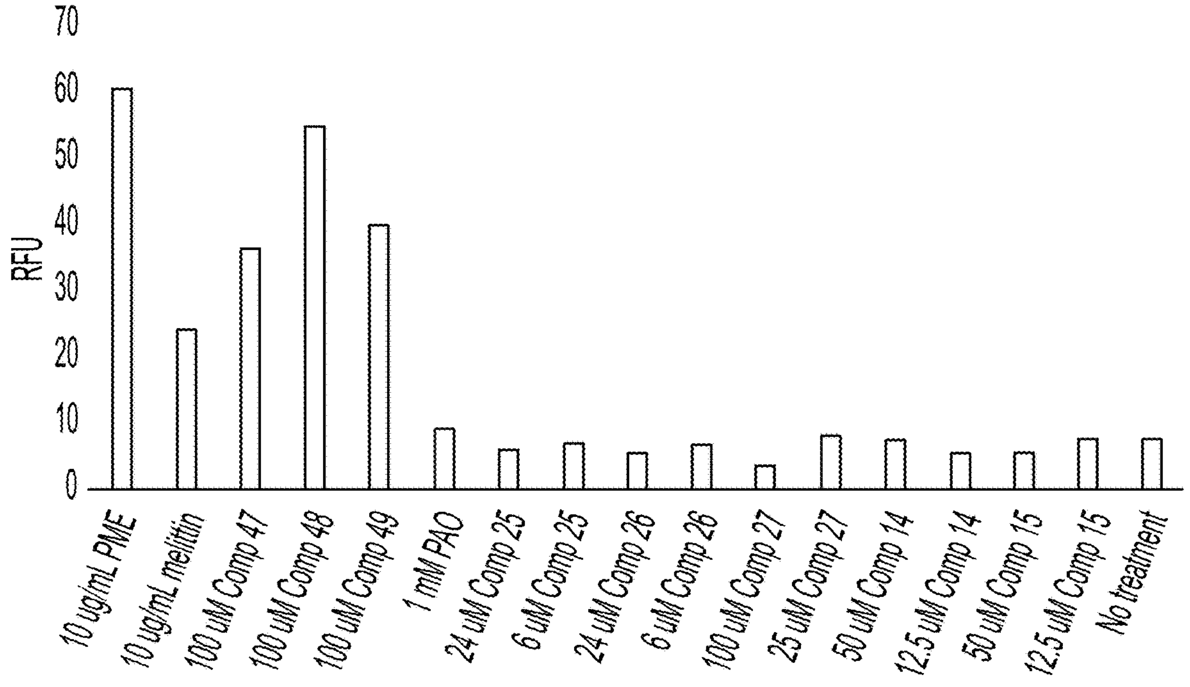
FIG. 23 shows the effect of Melittin, PME, Compound 47, Compound 48, Compound 49, Compound 25, Compound 26, Compound 27, Compound 14, and Compound 15 on *A. baumannii* ATCC BAA-1797 PI membrane permeability.

Melittin, PME, Compound 47, Compound 48, and Compound 49 caused cell permeability as is indicated by the increase in relative fluorescence units (RFU), while Compound 25, Compound 26, Compound 27, Compound 14, and Compound 15 did not permeabilize cells, indicating these are likely not membrane active compounds. FIG. 23 shows the effect of Melittin, PME, Compound 47, Compound 48, Compound 49, Compound 25, Compound 26, Compound 27, Compound 14, and Compound 15 on *A. baumannii* ATCC BAA-1797 PI membrane permeability.

Example 18: ATP Decrease Caused by Treatment with Compound 25, Compound 26, Compound 27, Compound 14, and Compound 15 on *A. Baumannii* ATCC 1515

*A. baumannii* ATCC 15151 was grown from a glycerol stock by placing a small volume of cells onto a MHA plate. The MHA plate was incubated overnight at 37° C. A single colony was subsequently used to inoculate MHB to obtain a bacterial broth suspension. The MHB broth suspension was grown at 37° C. on a rotary shaking incubator (100 rpm) for 12 hours. The bacterial cell concentration was adjusted to ~$5\times10^7$ CFU/mL in MHB using OD at 595 nm. Cells were treated with 1×MIC and 2×MIC e.g. 6 μM and 12 μM Compound 25, 12 and 24 μM Compound 26, and 12.5 μM and 25 μM Compound 27. The cells were incubated further for 25 minutes at 37° C. 200 μL of lysis buffer was added to 200 μL cells. The cells were frozen at −80° C. and thawed at 37° C. 25 μL luciferase was added to 100 μL aliquots of the lysed cell samples. The cells were incubated at 37° C. for 15 minutes before reading on Tecan plate reader using a pre-set luminescence setting.

Figure 24:
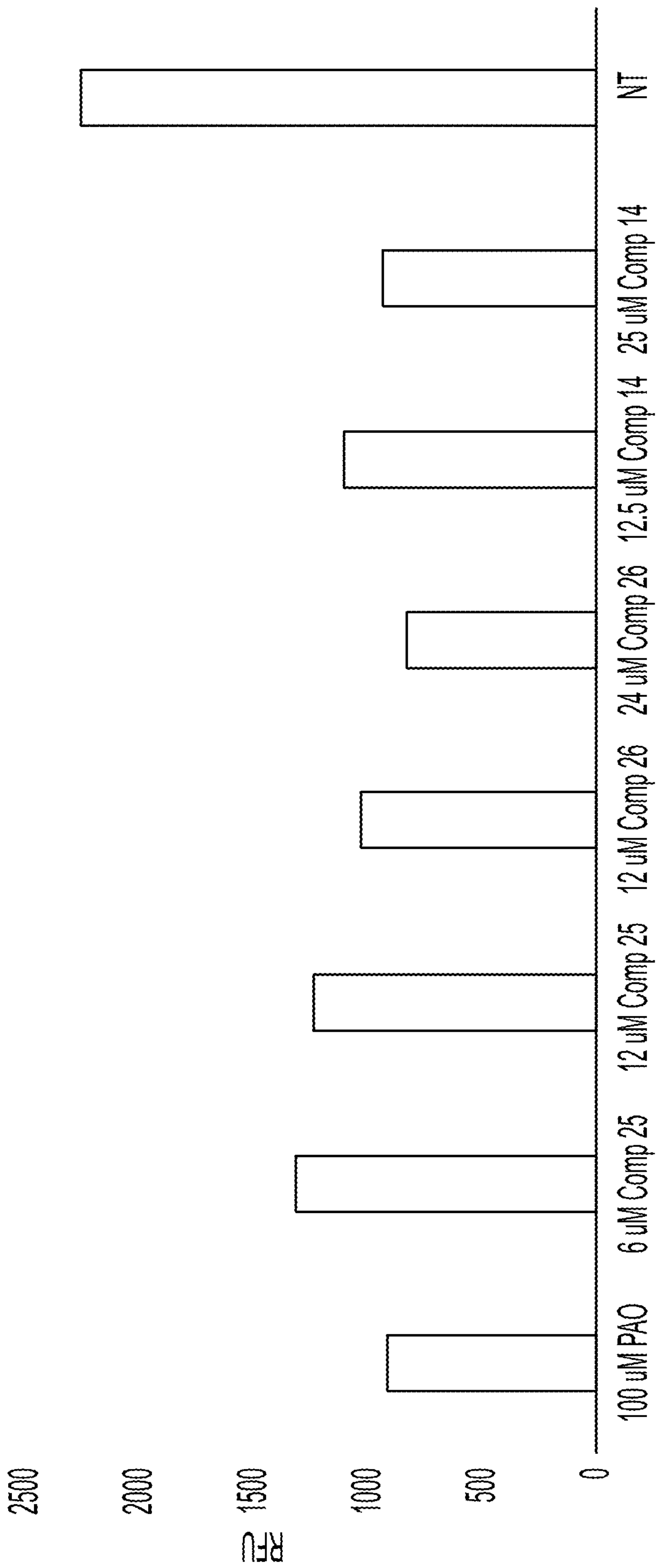
FIG. 24 shows that treatment with Compound 25, Compound 26, Compound 27, Compound 14, and Compound 15 on *A. baumannii* ATCC 1515 caused a decrease in ATP.

A clear dose-dependent decrease in ATP was observed in each treatment. FIG. 24 shows that treatment with Compound 25, Compound 26, Compound 27, Compound 14, and Compound 15 on *A. baumannii* ATCC 1515 caused a decrease in ATP.

Example 19: Membrane Depolarization Detected by DiOC2(3) Caused by Treatment with Compound 25, Compound 26, and Compound 14 on *A. Baumannii* ATCC 1515

Bacterial cells were prepared using the methods described above. Cells were stained with 5 μM DiOC2(3) for 20 minutes. The cells were then treated with 1×MIC (e.g. 6 μM Compound 25, 12 μM Compound 25, 12.5 μM Compound 26, or 20 μM CCCP alone. Cells were incubated for 25 minutes at 37° C., and fixed with 2.5% paraformaldehyde. Cells were read on a flow cytometer (FL2).

Figure 25A:
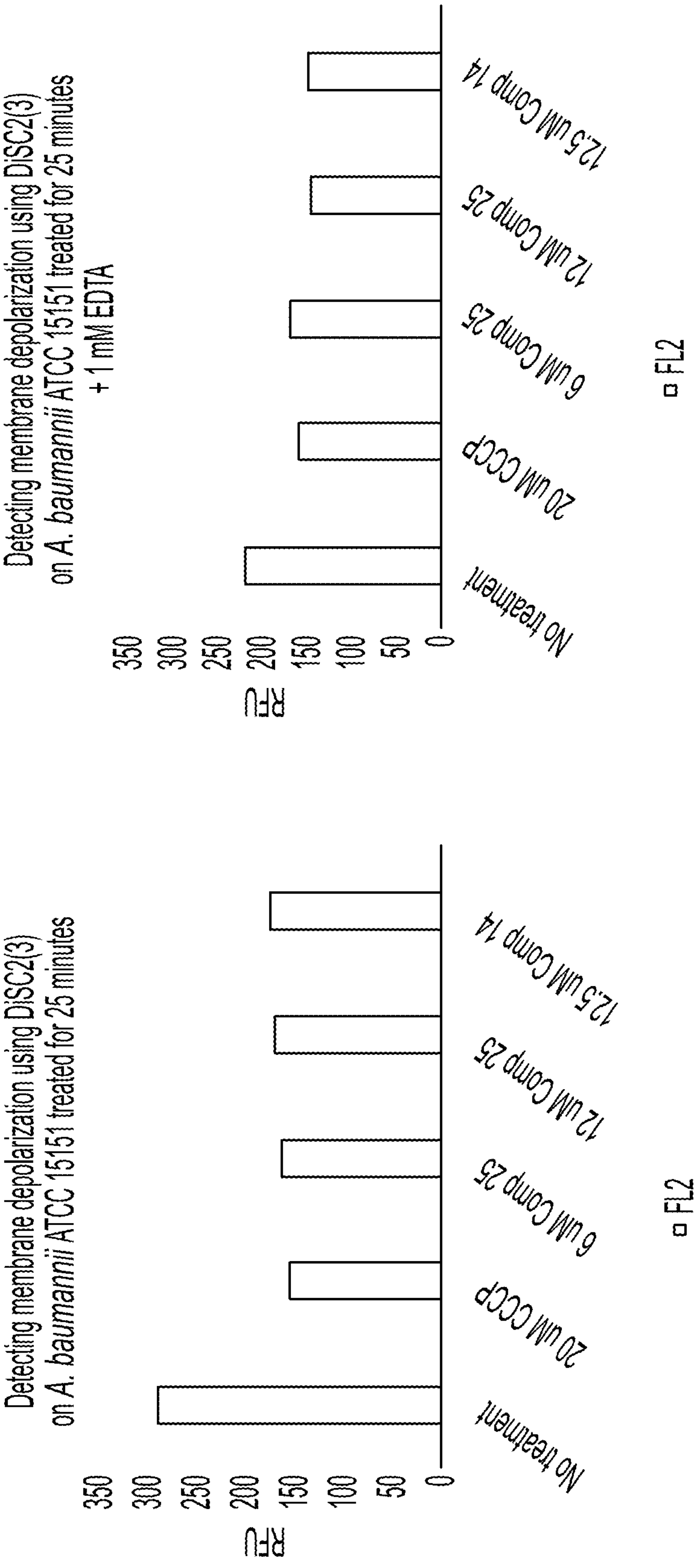
FIGS. 25A and 25B show that *A. baumannii* cells treated with compounds 25, 26, and 14 resulted in cell membrane depolarization.

Compound 25, Compound 26, Compound 14, and CCCP depolarized the cell membrane. FIG. 25A shows *A. baumannii* cells treated with compounds 25, 26, and 14 resulted in cell membrane depolarization.

In a separate experiment, bacterial cells were prepared using methods described above. Cells were stained with 5 μM DiOC2(3) for 20 minutes. Cells were treated with 1×MIC (e.g., 6 μM Compound 25, 12 μM Compound 26, and 12.5 μM Compound 26, or 20 μM CCCP alone. The cells were incubated for 10, 20, 30, and 50 minutes at 37° C. Cells were fixed with 2.5% paraformaldehyde at appropriate time intervals. The cells were read on a flow cytometer (FL2).

Figure 25B:
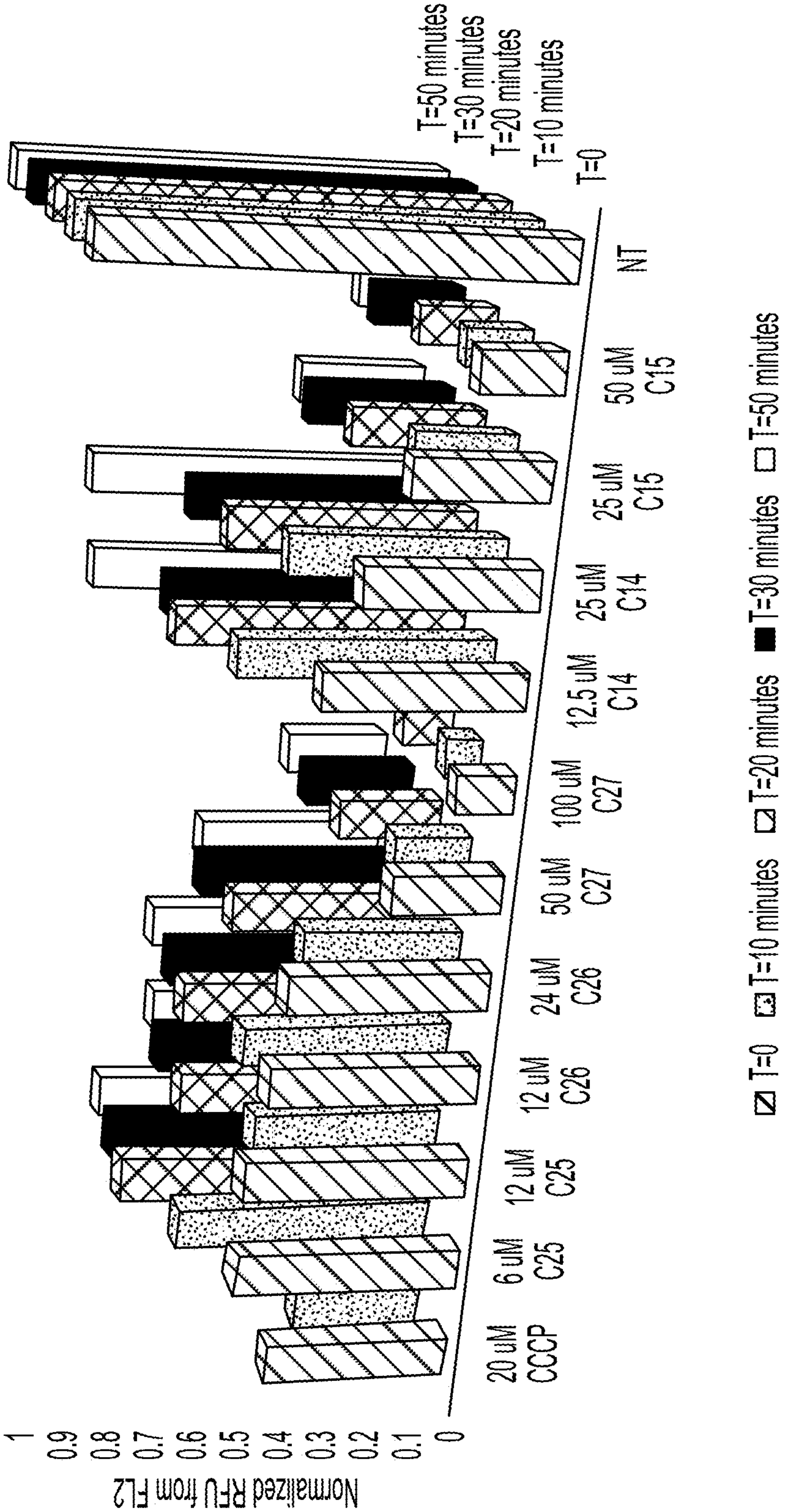

All of the compounds quickly depolarized the cell membrane (0 to 10 minutes). Compound 25 depolarized the membrane the least, while Compound 27 and Compound 15 caused the most depolarization. FIG. 25B shows *A. bau-*

*mannii* cells treated with compounds 25, 26, and 14 resulted in cell membrane depolarization.

Example 20: Red Blood Cell Lysis Capacity of Compound 14–/+40% Human Serum

Diluted red blood cells were aliquoted into clear tissue culture media–/+addition of 40% human serum and added either 2 μL or 40 μL of cell lysis buffer (LB), 50 μM, 40 μM, 20 μM, 15 μM, 10 μM, or 5 μM Compound 14. The samples were agitated by vortex and spun by centrifuge. In no additional serum, 40 μM Compound 14 lysed some red blood cells (RBC), but the effect was less than that caused by lysis buffer. In 40% additional serum, 50 μM Compound 14 did not lyse cells.

Figures 1, 26A:
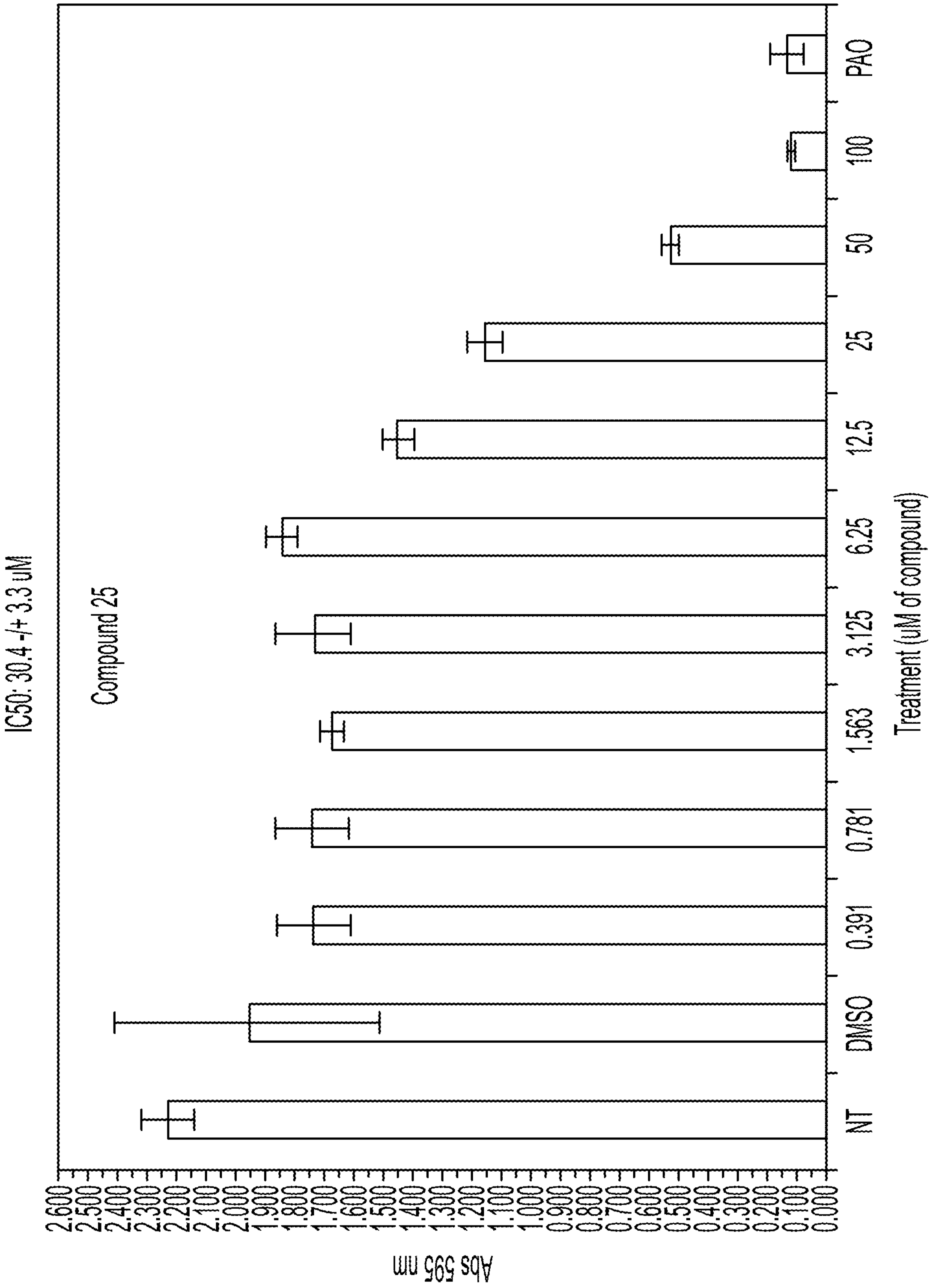
Figures 2, 26A:
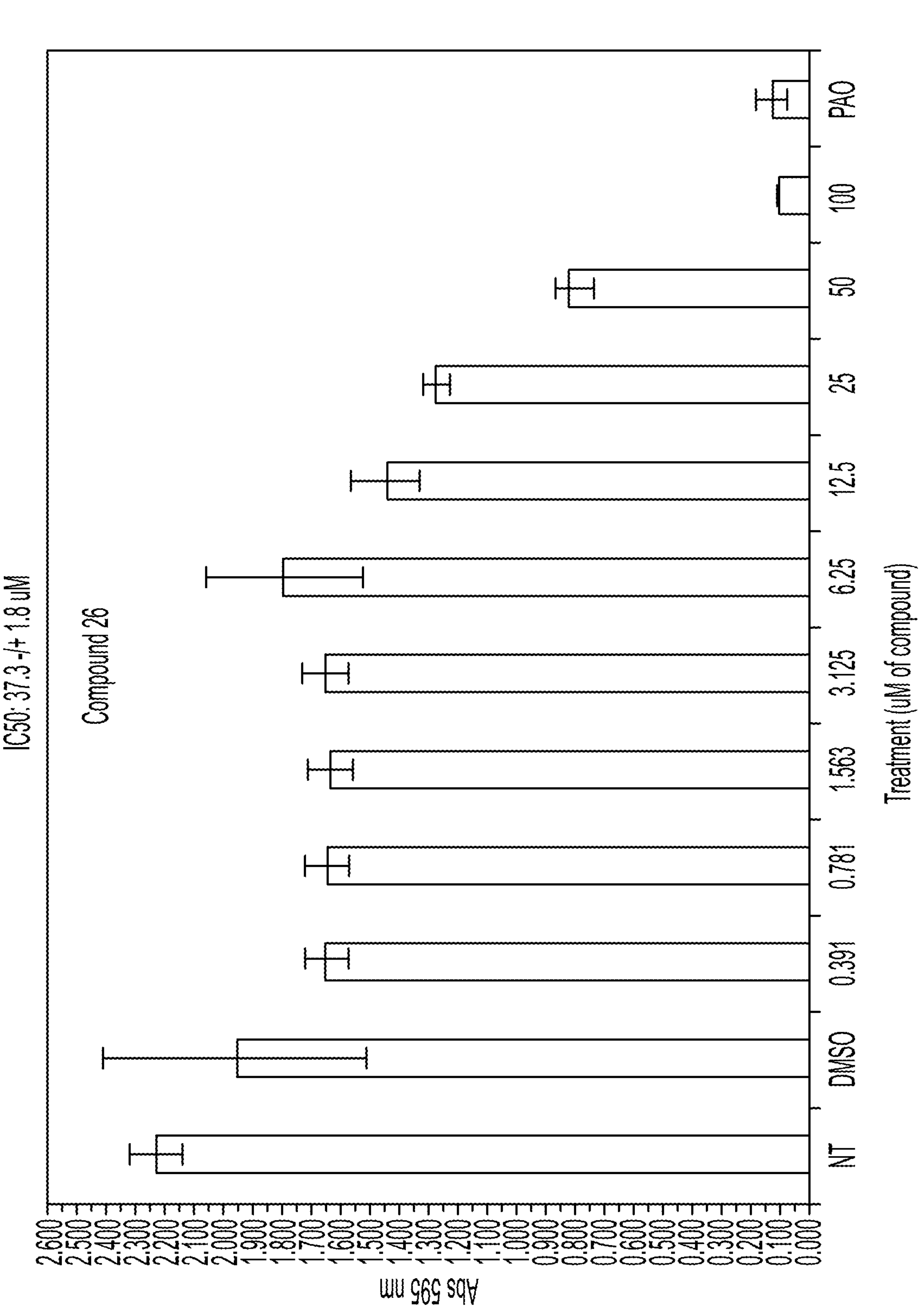
Figures 3, 26A:
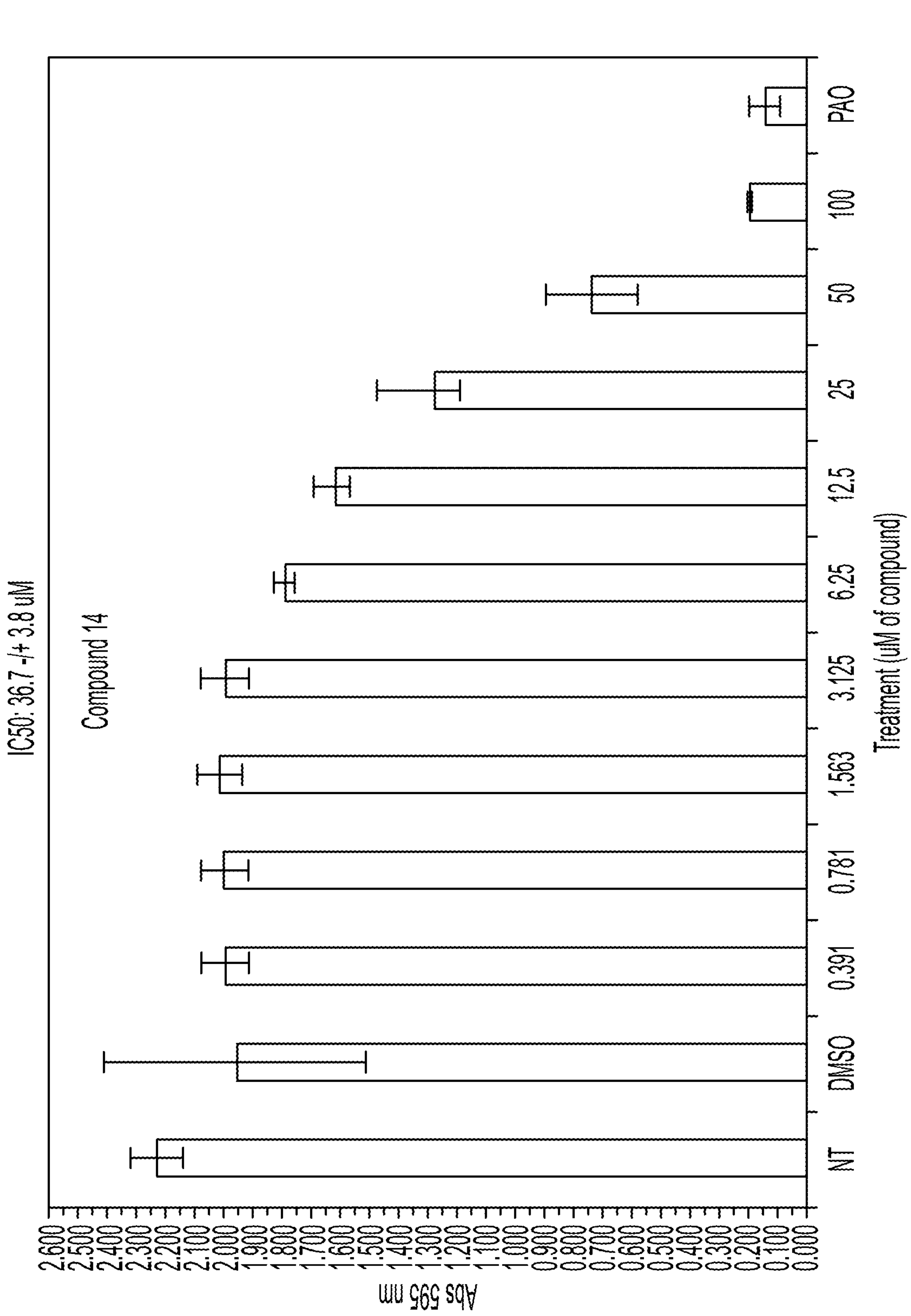
Figures 4, 26A:
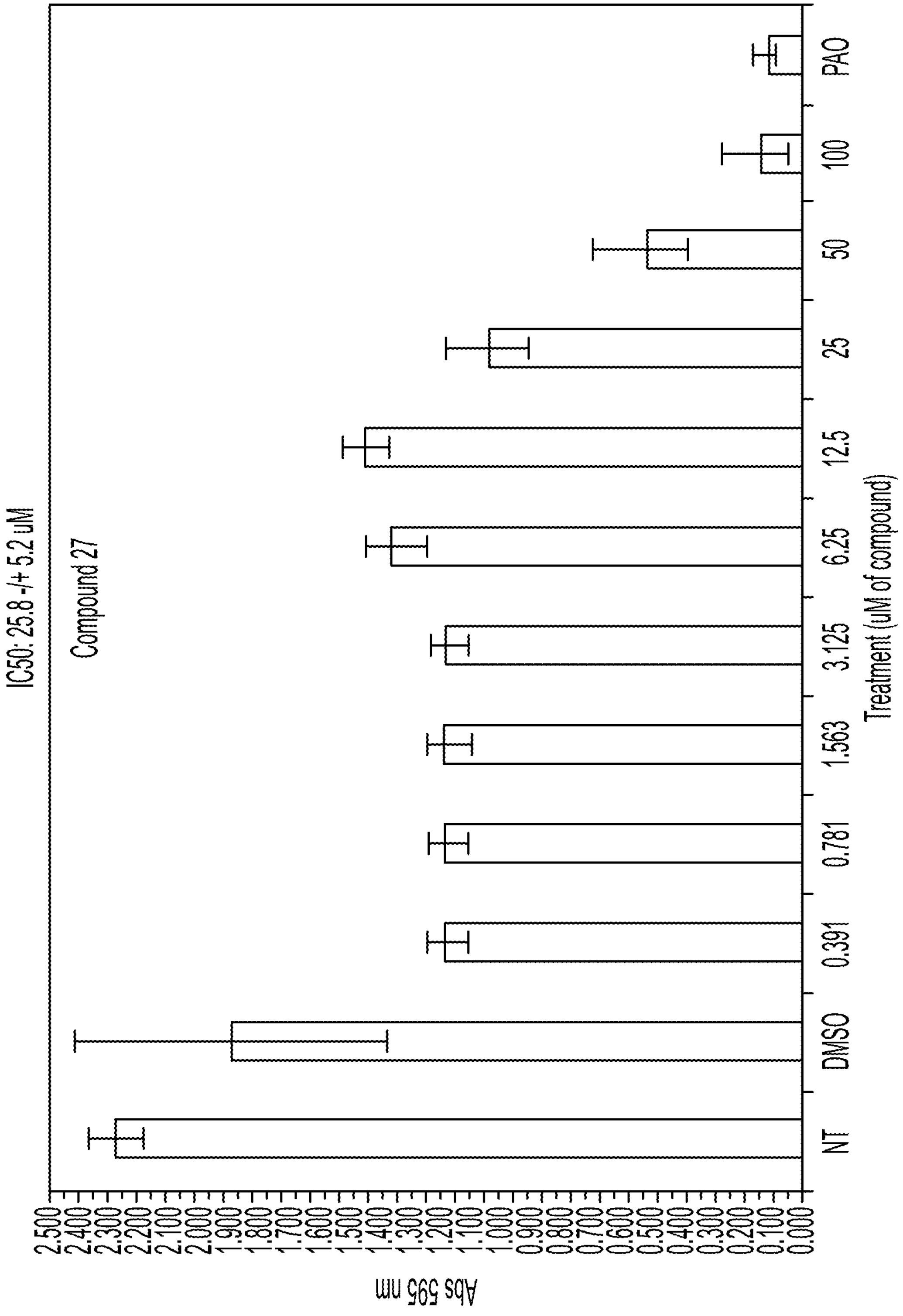
Figures 5, 26A:
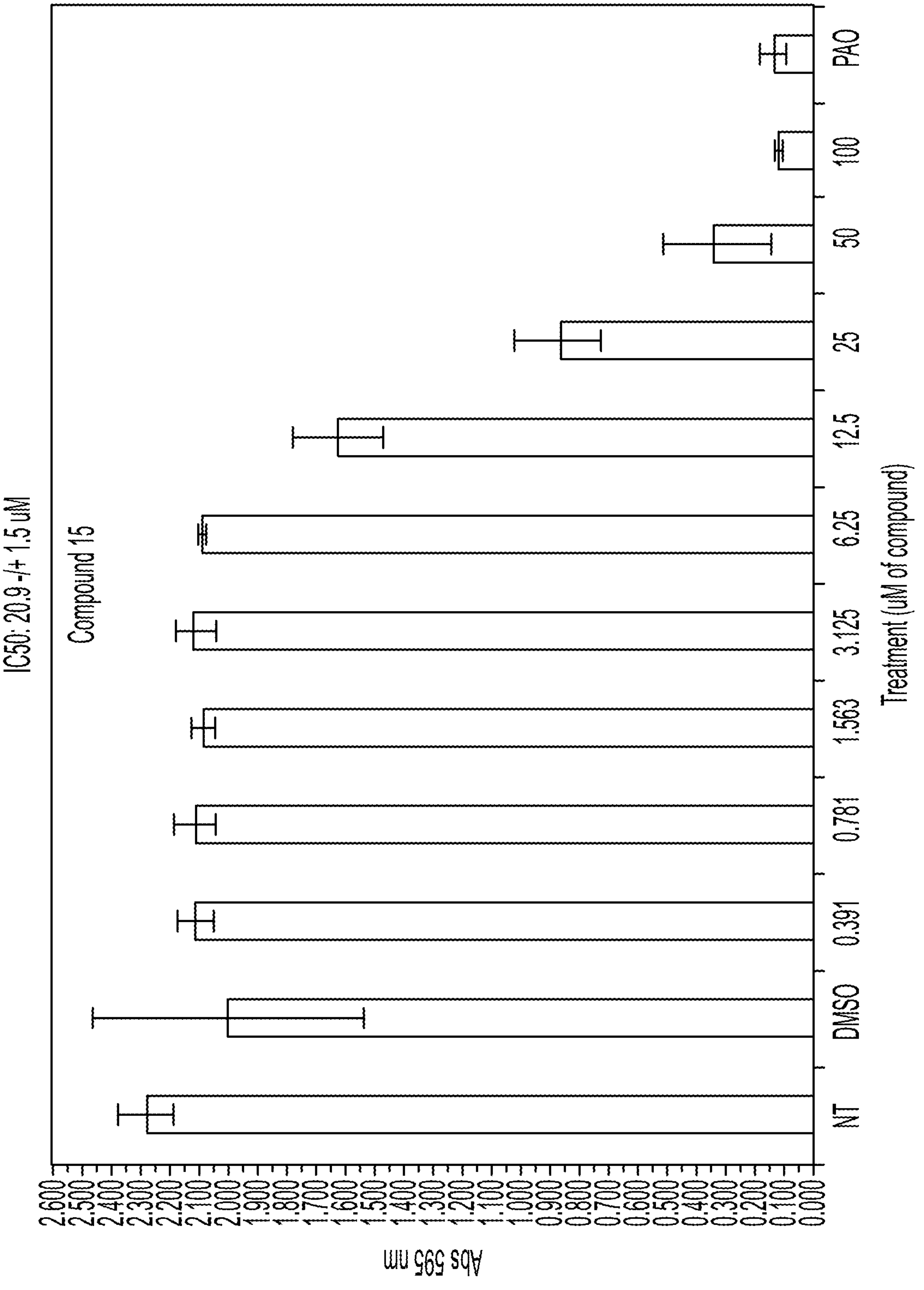
Figures 1, 26B:
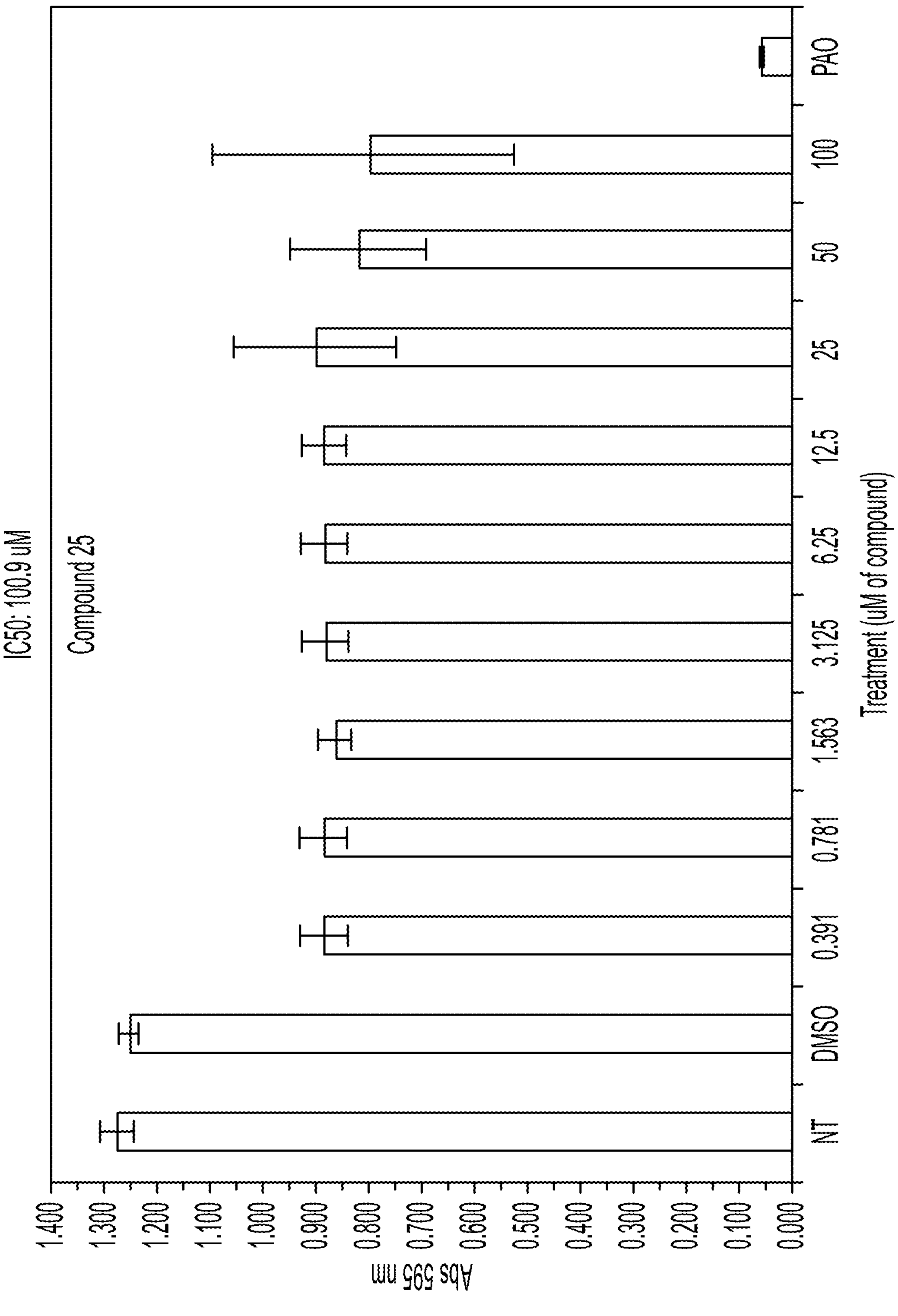
Figures 2, 26B:
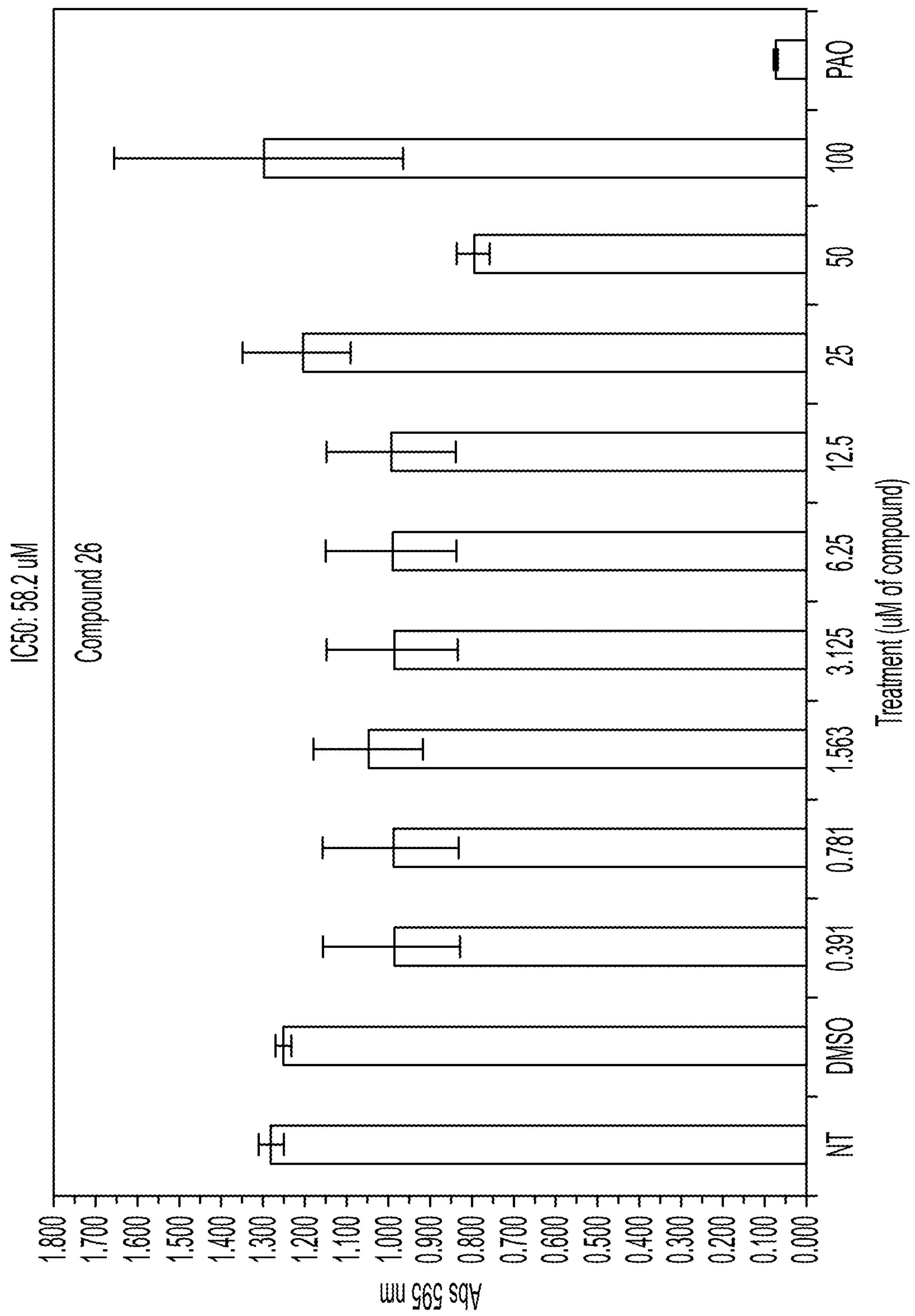
Figures 3, 26B:
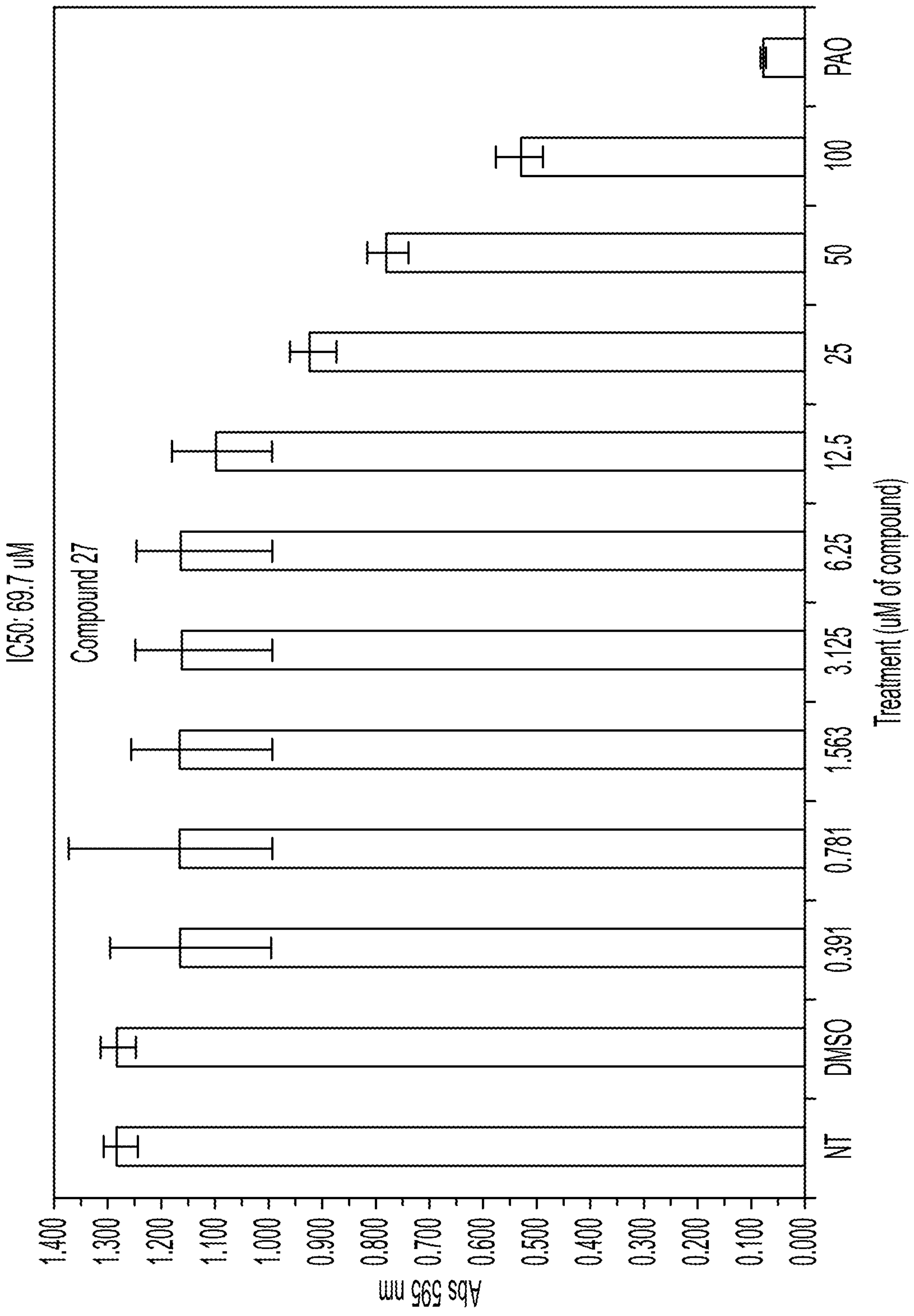
Figures 4, 26B:
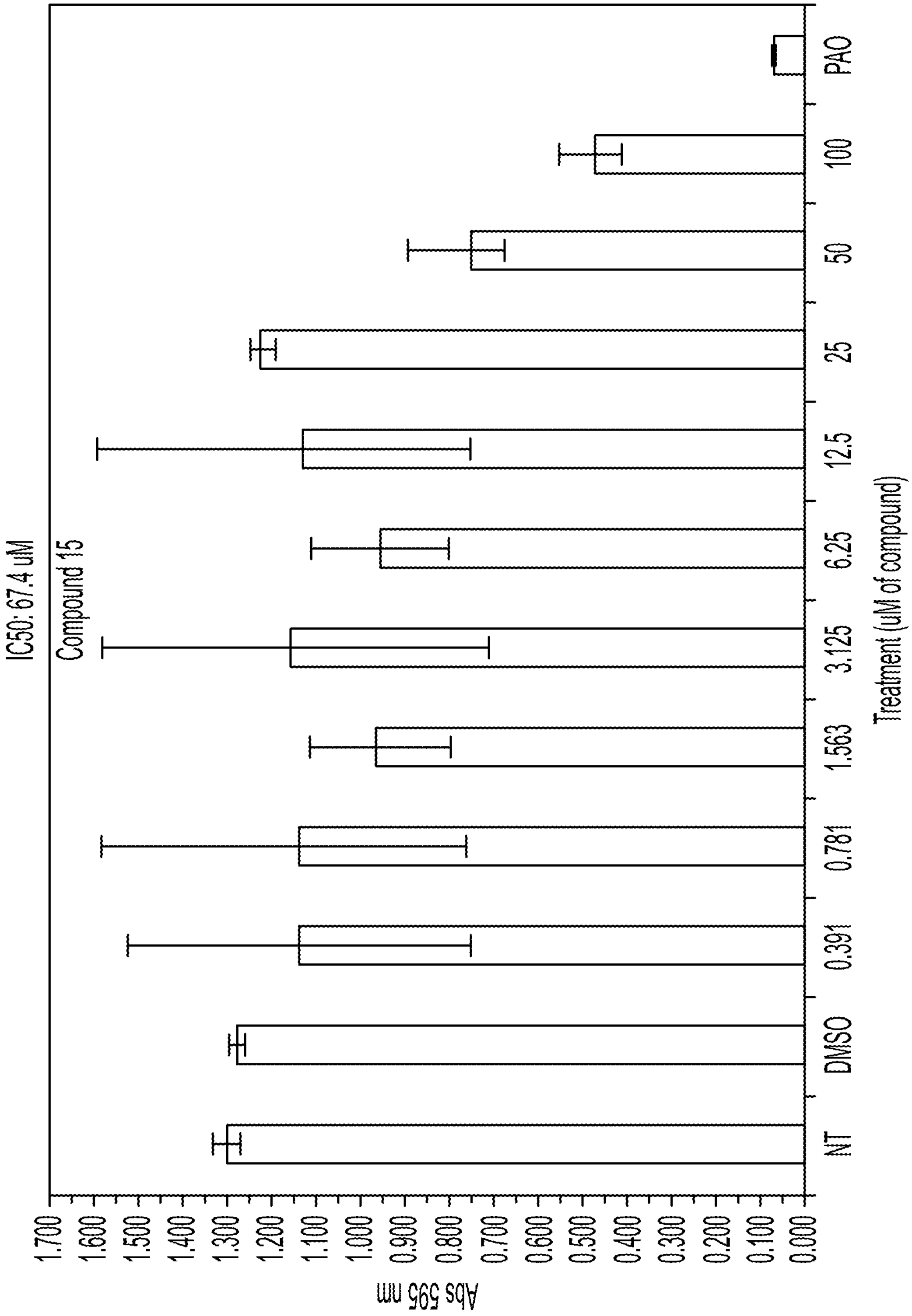
Figures 5, 26B:
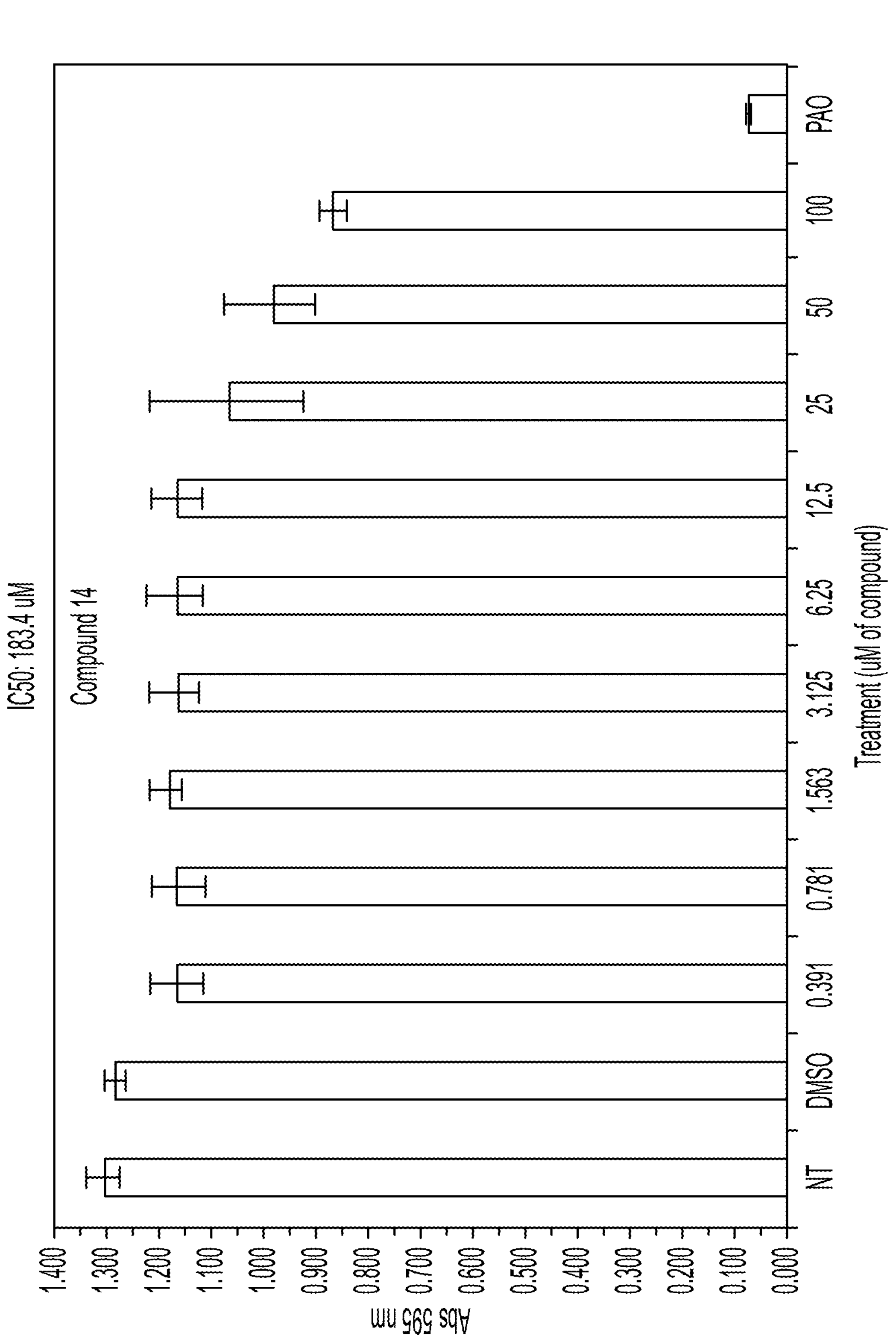

Example 21: Toxicity of Compound 25, Compound 26, Compound 27, Compound 14, and Compound 15 on HeLa Cells in 10% FBS and 40% FBS IC50 values were measured using the methods described above. The IC50 values for the compounds in 10% and 40% FBS are shown in TABLE 5. FIGS. 26A-1 to 26A show IC50 toxicity of Compound 25 (FIG. 26A-1), Compound 26 (FIG. 26A-2), Compound 27 (FIG. 26A-3), Compound 14 (FIG. 26A-4), and Compound 15 (FIG. 26A-5) on HeLa cells in 10% FBS. FIGS. 26B-1 to 26B-5 show IC50 toxicity of Compound 25 (FIG. 26B-1), Compound 26 (FIG. 26B-2), Compound 27 (FIG. 26B-3), Compound 14 (FIG. 26B-4), and Compound 15 (FIG. 26B-5) on HeLa cells in 40% FBS.

TABLE 5

| | IC50 | |
|---|---|---|
| Compound No. | 10% FBS (μM) | 40% FBS (μM) |
| 14 | 36.7 ± 3.8 | 183.4 |
| 15 | 20.9 ± 1.5 | 67.4 |
| 25 | 30.4 ± 3.3 | 100.9 |
| 26 | 37.3 ± 1.8 | 58.2 |
| 27 | 25.8 ± 5.2 | 69.7 |

In a separate experiment, the ability of compound 25 to selectively kill *A. baumannii* ATCC BAA-1797 in a culture of HeLa cells in 40% FBS was studied. Cells were trypsinized, counted (cells/mL) using a hemocytometer, and plated (2×$10^5$ HeLa cells/100 μL) in tissue culture-treated 24-well plate in DMEM+1% penicillin/streptomycin (P/S)+ 10% FBS. Cells were adhered overnight at 37° C. in a humidified incubator with 5% $CO_2$. Media was replaced the following day with DMEM+40% or 50% FBS. Selected wells were treated with 60 μM Compound 26, which included HeLa only and HeLa plus 10,000 *A. baumannii* ATCC BAA-1797—that had been previously grown in MHB for 12 hours in 37° C.—in the appropriate wells. Cells were incubated further for 18 hours at 37° C. 20% v/v MTT reagent (5 mg/mL stock) was added, and the samples were incubated for 10 minutes to observe viable bacteria. Plates were counted after a visual viability assessment.

Figure 27A:
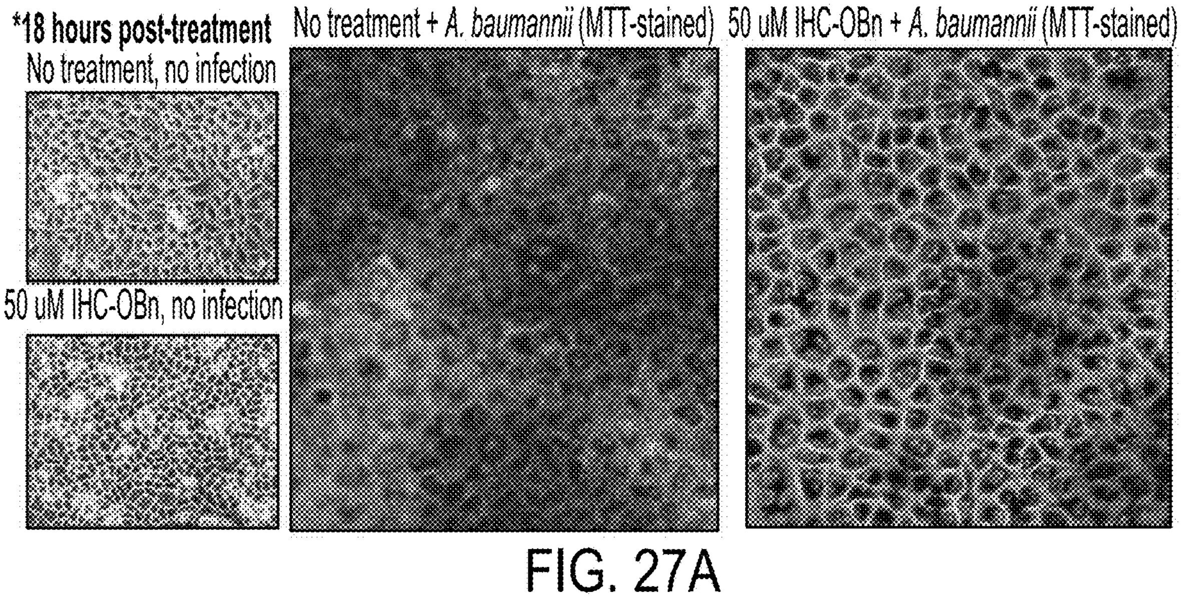
FIGS. 27A and 27B show that Compound 26 selectively eradicated *A. baumannii* ATCC BAA-1797 from HeLa cells, leaving HeLa cells unharmed.

Treatment with 60 μM Compound 26 selectively eradicated *A. baumannii* ATCC BAA-1797 from HeLa cells, leaving HeLa cells unharmed. FIG. 27A shows that Compound 26 selectively eradicated *A. baumannii* ATCC BAA-1797 from HeLa cells, leaving HeLa cells unharmed.

In a separate experiment, the ability of compound 26 to selectively kill *A. baumannii* ATCC BAA-1797 in a culture of HeLa cells in 40% FBS and 50% FBS was studied.

Cells were trypsinized, counted (cells/mL) using a hemocytometer, and plated (2×$10^5$ HeLa cells/100 μL) in tissue culture-treated 24-well plate in DMEM+1% penicillin/streptomycin (P/S)+10% FBS. Cells were adhered overnight at 37° C. in a humidified incubator with 5% $CO_2$. Media was replaced the following day with DMEM+40% or 50% FBS. Selected wells were treated with 60 μM Compound 26, which included HeLa only and HeLa plus 10,000 *A. baumannii* ATCC BAA-1797—that had been previously grown in MHB for 12 hours in 37° C.—in the appropriate wells. Cells were incubated 18 hours at 37° C. 20% v/v MTT reagent (5 mg/mL stock) was added, and the samples were incubated for 10 minutes to observe viable bacteria. Plates were counted after visual viability assessment.

Figure 27B:
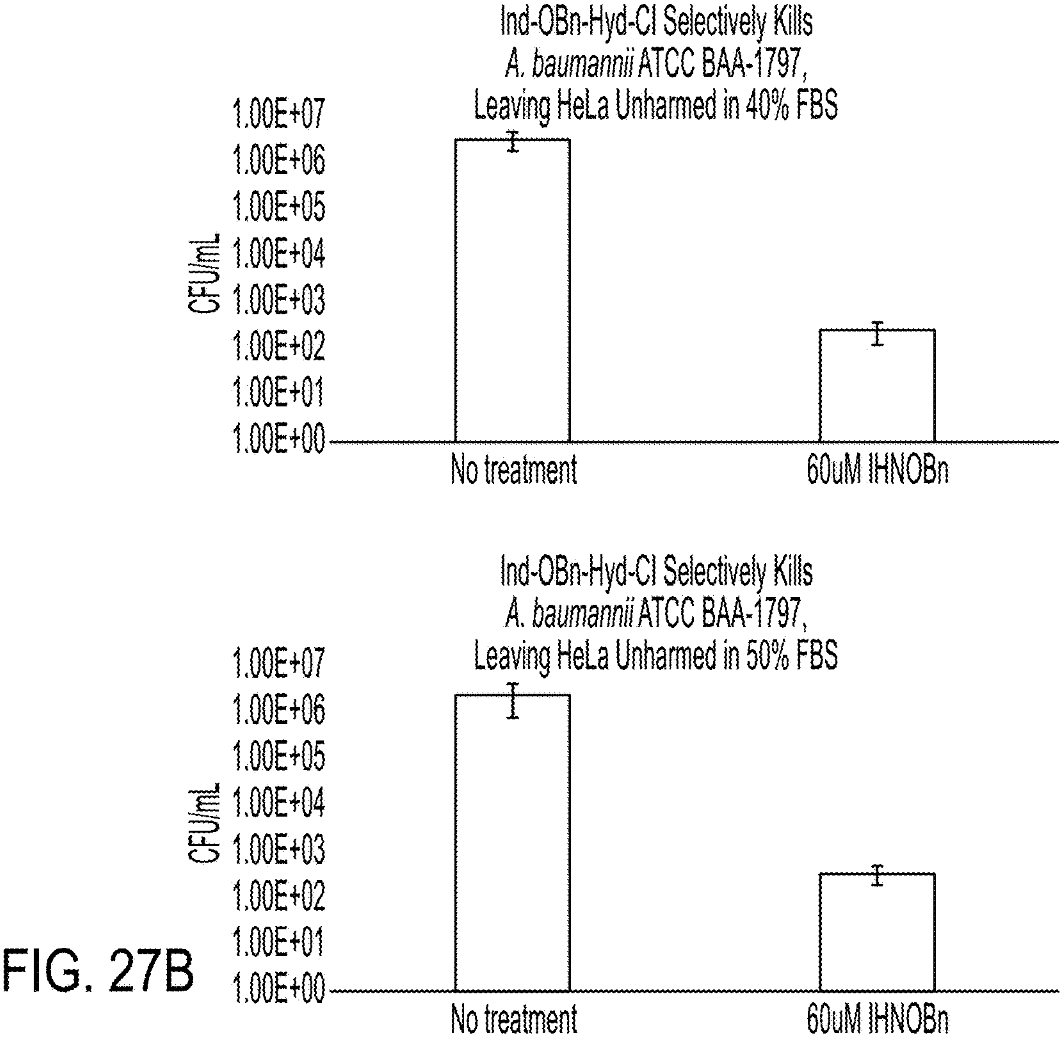

Treatment with 60 μM Compound 26 selectively eradicated *A. baumannii* ATCC BAA-1797 from HeLa cells, leaving HeLa cells unharmed. Treatment with 60 μM Compound 26 killed 4-logs of *A. baumannii* ATCC BAA-1797 in 40% FBS and 50% FBS. FIG. 27B shows that Compound 26 selectively eradicated *A. baumannii* ATCC BAA-1797 from HeLa cells, leaving HeLa cells unharmed.

Example 22: Norfloxacin Plus Compound 25, Compound 26, Compound 27, Compound 14, and Compound 15 for Inhibition of RecA Induction on *E. coli* MG1655 RecA The SOS response is a widely conserved DNA damage repair network that allows bacteria to survive severe DNA damage at the cost of elevated mutagenesis and acquired resistance to genotoxic stressors. The transcription-requiring process repairs DNA lesions through mutagenic DNA polymerization and repair. The LexA protein negatively regulates expression of the SOS response. When DNA-lesion-dependent RecA inactivates a LexA repressor, transcription of the SOS gene products takes place. Among the products is an error-prone DNA polymerase V encoded by UmuC and UmuD genes and a RecA protein. Genetic integrity is sacrificed for cell survival. However, when the recognition of DNA damage by RecA, or expression of the error-prone polymerase or expression the additional RecA is blocked or overwhelmed, the SOS response leads to apoptosis-like cell death.

The compounds of the disclosure can interfere with the RecA/LexA-mediated bacterial SOS response and trigger apoptosis-like death in most gram-negative cells, including, for example, *E. coli*. Blockage of detection of the dsDNA-triggered DNA damage (caused by norfloxacin) SOS response can also subsequently reduce the likelihood of additional expression of RecA. In *A. baumannii*, LexA function can replaced by another protein. Note that in *A. baumannii*, failure of RecA to identify dsDNA damage could also result in the triggering of the full SOS response, including bacterial cell death. Concurrent failure to express the mutator/error-prone DNA polymerase reduces the likelihood of or can slow down the evolution of drug resistance.

Additionally, dsDNA damage (e.g caused by ciprofloxacin) induces bacterial filamentation. In the presence of the compounds of the disclosure, which can in some embodiments interfere with dsDNA damage recognition, filamentation can be suppressed.

*E. coli* MG1655 was grown from a glycerol stock by placing a small volume of cells onto a MHA plate. The MHA plate was incubated overnight at 37° C. A single colony was subsequently used to inoculate MHB+10 μg/mL kanamycin to obtain a bacterial broth suspension. The MHB broth suspension was grown at 37° C. on a rotary shaking incubator (100 rpm) for 12 hours. The bacterial cell concentration was adjusted to ~5x$10^5$ CFU/mL in MHB using OD at 595 nm.

Cells were treated with 0.03 μg/mL and 0.06 μg/mL norfloxacin for 30 minutes at 37° C. Then, 100 μM of the compounds were added. The cells were incubated for 3.5 hours at 37° C. 200 μL aliquots were removed and read by a flow cytometer to detect RecA production and/or shutdown. The cells were incubated for an additional 18 hours at 37° C. to assess overall toxicity.

Figure 28:
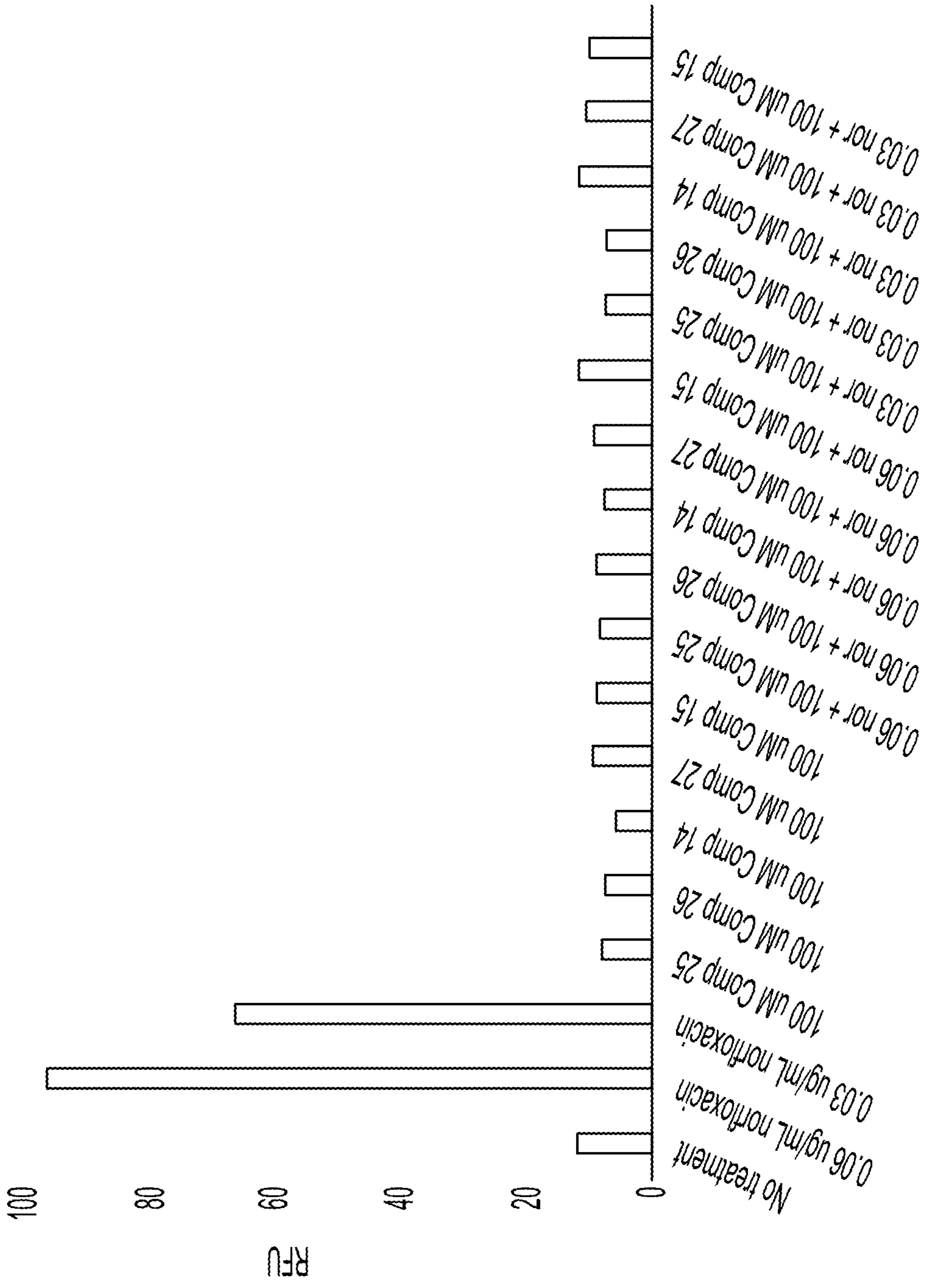
FIG. 28 shows that each of the gram-negative compounds stopped RecA production in *E. coli* at 3.5 hours.
Figure 29A:
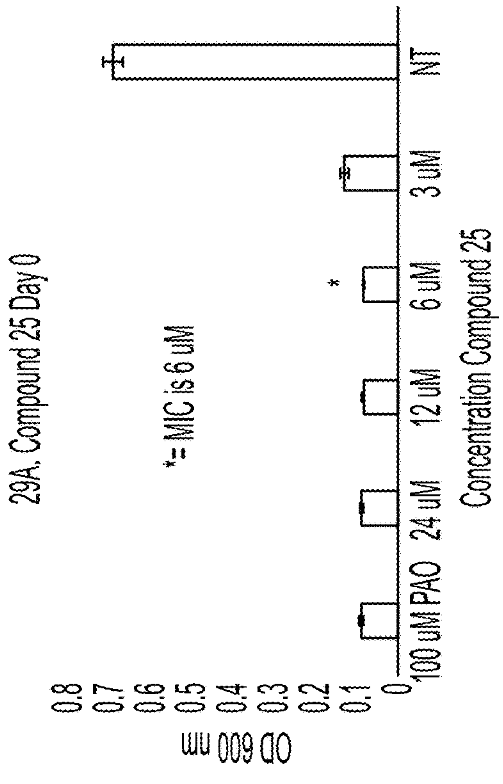
FIGS. 29A-29D show starting MIC values of compounds 25 (FIG. 29A), 26 (FIG. 29B), 14 (FIG. 29C), and ciprofloxacin (FIG. 29D) in *A. baumannii*.
Figure 29B:
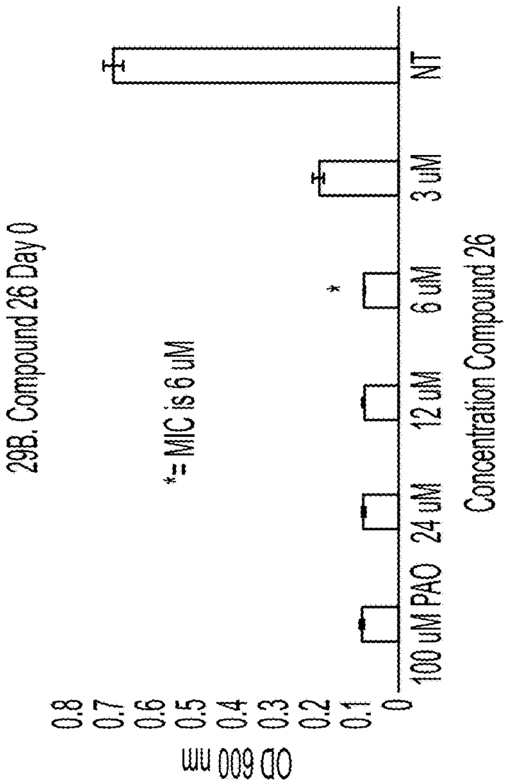
Figure 29C:
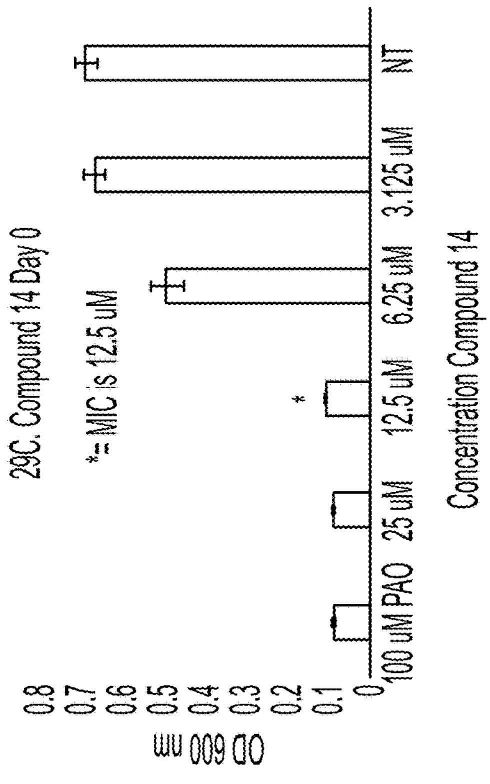
Figure 29D:
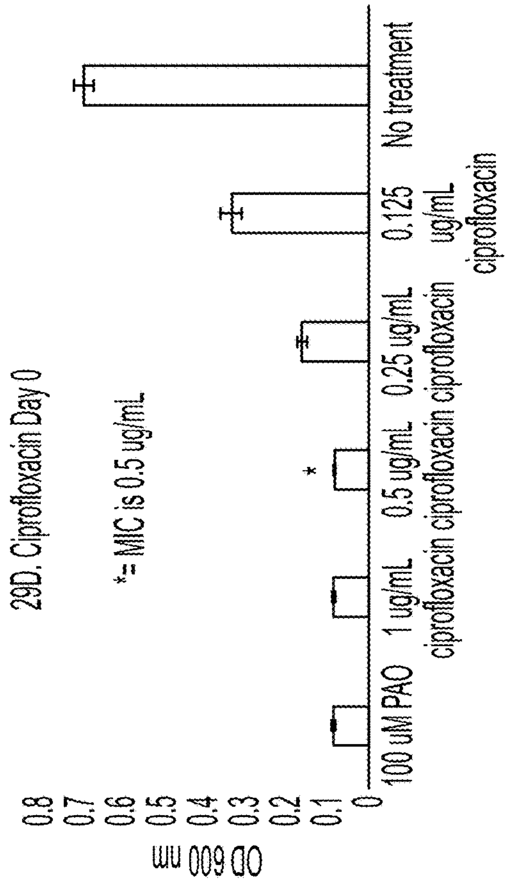
Figure 29F:
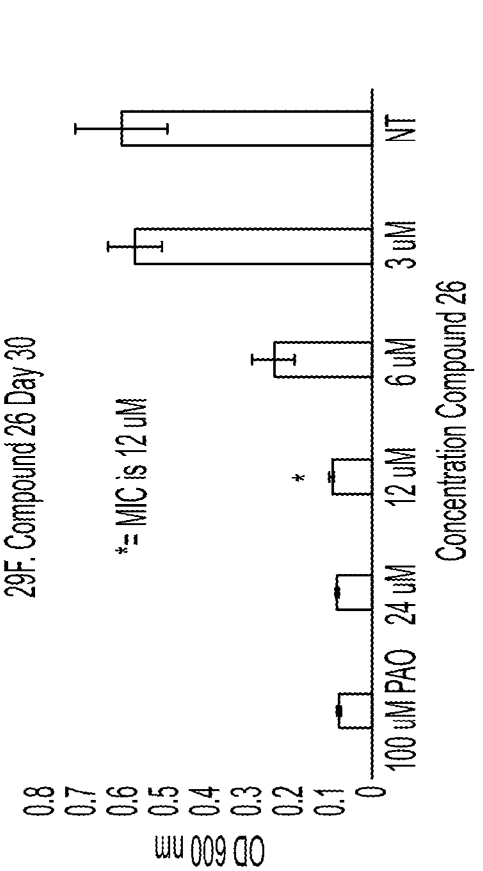
FIGS. 29E-29H show final MIC values of compounds 25 (FIG. 29E), 26 (FIG. 29F), 14 (FIG. 29G), and ciprofloxacin (FIG. 29H) in *A. baumannii.*
Figure 29H:
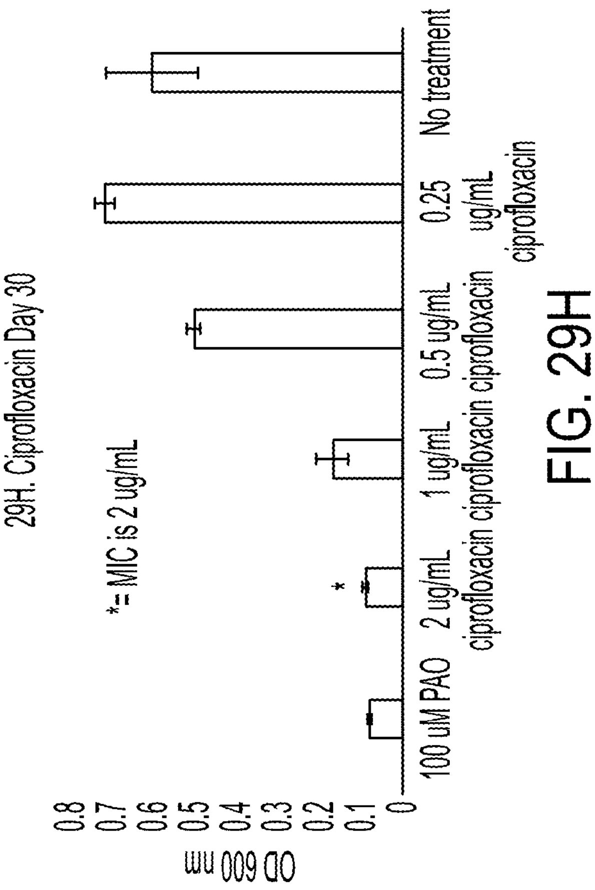
Figure 29E:
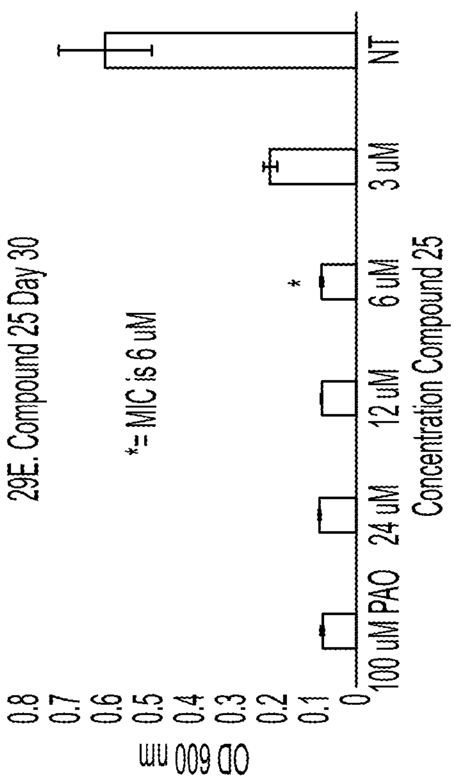
Figure 29G:
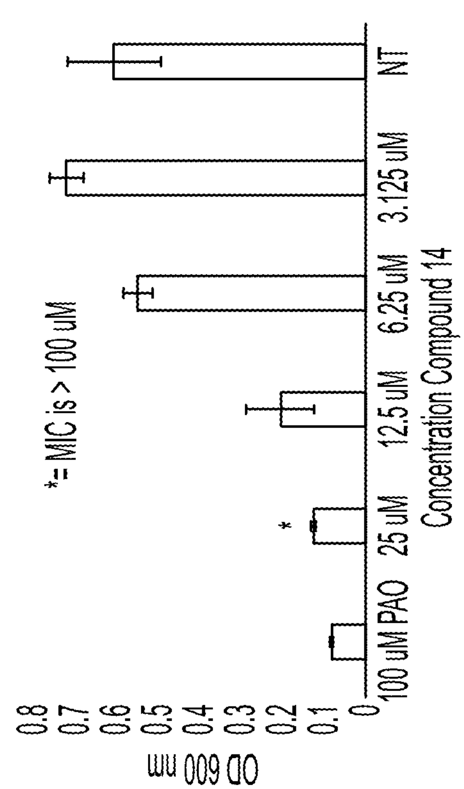

The compounds did not synergize with norfloxacin, but each of the compounds shut off RecA and SOS responses, as can be seen by the low RFU in the graph. FIG. 28 shows that each of the gram-negative compounds stopped RecA production in *E. coli* at 3.5 hours.

Example 23: *A. Baumannii* does not Develop Resistance Against Compound 25

*A. baumannii* ATCC 15151 was grown from a glycerol stock by placing a small volume of cells onto a MHA plate. The MHA plate was incubated overnight at 37° C. A single colony was subsequently used to inoculate MHB to obtain a bacterial broth suspension. The MHB broth suspension was grown at 37° C. on a rotary shaking incubator (100 rpm) for 12 hours. The bacterial cell concentration was adjusted to ~5x$10^5$ CFU/mL in MHB or MHB using OD at 595 nm. 100 μL of the adjusted bacterial cell suspensions were placed into a 96-well plate, where the cell suspensions were treated with 24 μM Compound 25, 24 μM Compound 26, 25 or 100 μM Compound 14, or 1 μg/mL or 2 μg/mL ciprofloxacin; all treatments were serially diluted. The positive control was 100 μM phenylarsine oxide (PAO) and the negative control was non-treated cells. All treatments were performed in triplicate. The plate was incubated for 20 hours at 37° C. in a Tecan plate reader, where the cells were shaken every hour and an OD reading was taken at 600 nm. Following the incubation, cells were taken from wells that were 4-fold lower compound concentration than the MIC and re-diluted to 5x$10^5$ CFU/mL. These cells were again plated in a 96-well plate and incubated as before. This was performed a total of 30 days.

The MIC of Compound 25 remained the same at 6 μM on Day 0 and Day 30, showing that *A. baumannii* had not developed resistance against this compound. The MIC of Compound 26 changed 2-fold from a MIC of 6 μM on Day 0 to a MIC of 12 μM on Day 30, showing that *A. baumannii* had developed slight resistance against this compound. The MIC of Compound 14 increased 8-fold from a MIC of 12.5 μM on Day 0 to a MIC of or above 100 μM on Day 30, showing that *A. baumannii* had developed significant resistance against this compound. The MIC of ciprofloxacin increased 4-fold from a MIC of 0.5 μg/mL on Day 0 to a MIC of 2 μg/mL on Day 30, showing that *A. baumannii* had developed significant resistance against this compound. TABLE 6 shows the starting MIC and final MIC values of the compounds. FIGS. 29A-29D show starting MIC values of compounds 25 (FIG. 29A), 26 (FIG. 29B), 14 (FIG. 29C) and ciprofloxacin (FIG. 29D) in *A. baumannii*. FIGS. 29E-29H show final MIC values of compounds 25 (FIG. 29E), 26 (FIG. 29F), 14 (FIG. 29G), and ciprofloxacin (FIG. 29H) in *A. baumannii*.

TABLE 6

| Compound | Starting MIC Day 0 (μM) | Final MIC Day 30 (μM) |
|---|---|---|
| 25 | 6 | 6 |
| 26 | 6 | 12 |
| 14 | 12.5 | >100 |
| Ciprofloxacin | 0.5 μg/mL | 2 μg/mL |

Example 24: Filamentation with Ciprofloxacin and Compound 25 on *A. Baumannii* ATCC 15151 and *E. coli*

*A. baumannii* ATCC 15151: Bacterial cells were grown using methods described above. 500 μL aliquots of the adjusted bacterial cell suspensions were placed into borosilicate glass tubes, where the cell suspensions were treated with 125 ng/mL ciprofloxacin, 50 ng/mL ciprofloxacin, 2.5 μM Compound 25, or 50 ng/mL ciprofloxacin+2.5 μM Compound 25. The culture tubes were incubated for 18 hours at 37° C. After 18 hours incubation, took 3 μL of cells from each well and plated on microscope slide to observe the following:

Non-treated cells were morphologically normal and full growth was observed. 50 ng/mL ciprofloxacin-treated cells were slightly elongated and some growth inhibition was observed. 2.5 μM Compound 25-treated cells were morphologically normal and full growth was observed—Compound 25 did not cause DNA damage. 2.5 μM Compound 25+50 ng/mL ciprofloxacin-treated cells were elongated in morphology and growth inhibition was observed. 125 ng/mL ciprofloxacin-treated cells were largely elongated in morphology and growth inhibition was observed. If Compound 25 inhibits the ability of RecA to sense DNA damage, then Compound 25 can prevent ciprofloxacin-induced filamentation. Compound 25 only slightly inhibited ciprofloxacin-induced filamentation. FIGS. 30A-30E show filamentation with ciprofloxacin and Compound 25 on *A. baumannii* ATCC 15151.

Figure 30A:
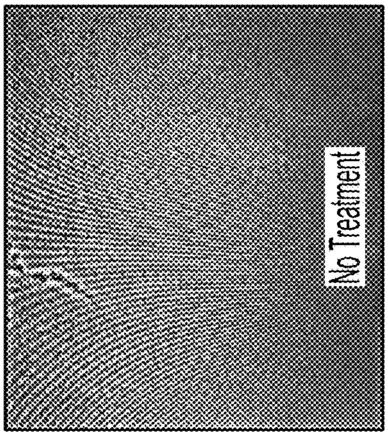
FIGS. 30A-30E show filamentation with ciprofloxacin and Compound 25 on *A. baumannii* ATCC 15151.
Figure 30B:
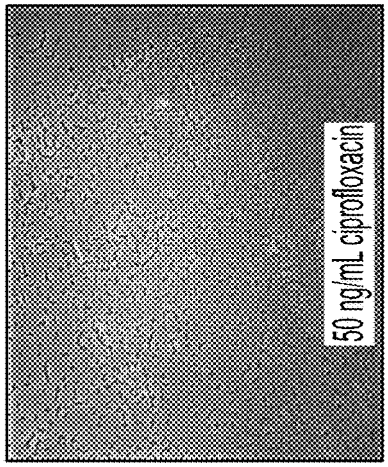
Figure 30C:
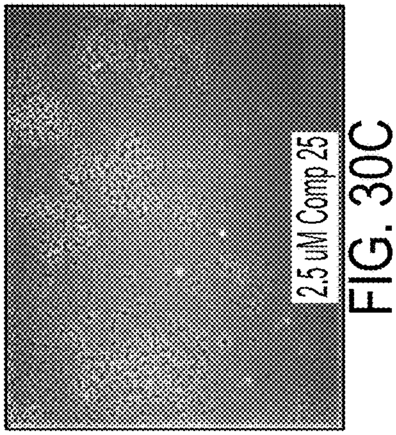
Figure 30D:
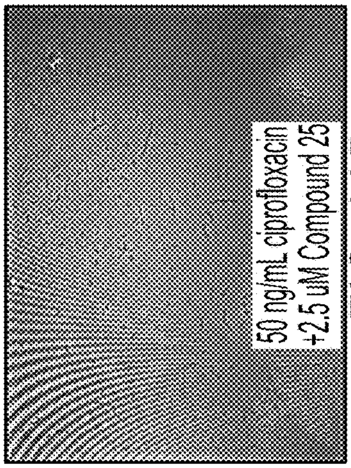
Figure 30E:
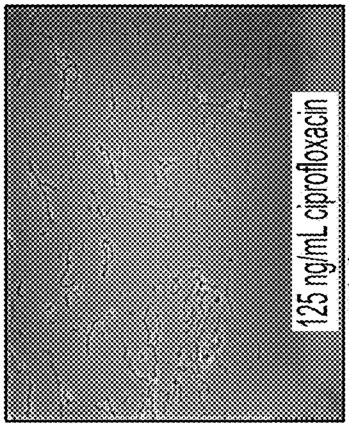
Figure 30F:
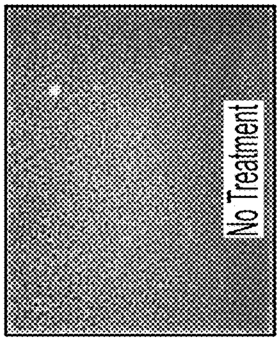
Figure 30G:
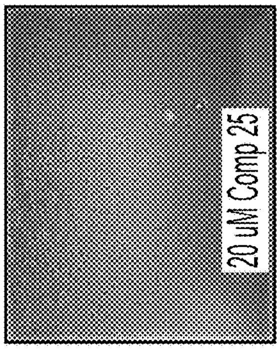
Figure 30H:
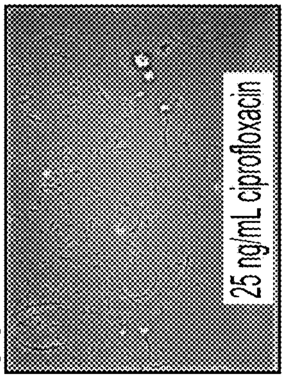
Figure 30I:
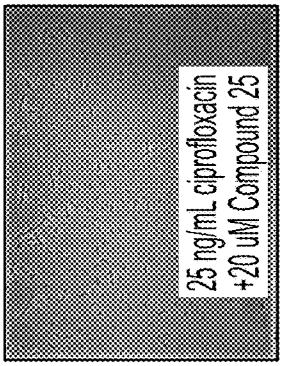

*E. coli*: *E. coli* was grown from a glycerol stock by placing a small volume of cells onto a MHA plate. The MHA plate was incubated overnight at 37° C. A single colony was subsequently used to inoculate MHB to obtain a bacterial broth suspension. The MHB broth suspension was grown at 37° C. on a rotary shaking incubator (100 rpm) for 12 hours. The bacterial cell concentration was adjusted to ~1x$10^7$ CFU/mL in MHB using OD at 595 nm. 500 μL aliquots of the adjusted bacterial cell suspensions were placed into borosilicate glass tubes, where the cell suspensions were treated with 25 ng/mL ciprofloxacin, 20 μM Compound 25, or 25 ng/mL ciprofloxacin+20 μM Compound 25. The culture tubes were incubated for 16 hours at 37° C. After 16 hours incubation, took 3 μL of cells from each well and plated on microscope slide to observe the following:

Non-treated cells were morphologically normal and full growth was observed. 25 ng/mL ciprofloxacin-treated cells were slightly elongated and some growth inhibition was observed. 20 μM Compound 25-treated cells were morphologically normal and growth inhibition was observed. 20 μM Compound 25+25 ng/mL ciprofloxacin-treated cells were elongated in morphology and growth inhibition was observed. If Compound 25 inhibited the ability of RecA to sense DNA damage, then Compound 25 can reduce the likelihood of ciprofloxacin-induced filamentation. Compound 25 only slightly inhibited ciprofloxacin-induced filamentation: the recognition of the dsDNA damage by RecA in the presence of Compound 25 may act downstream of RecA. FIGS. 30F-301 show filamentation with ciprofloxacin and Compound 25 on *E. coli.*

Example 25: DNA Degradation is Caused by $H_2O_2$ and Ciprofloxacin but not by Compound 25 in Drug-Sensitive *A. Baumannii* ATCC 15151. Neither Ciprofloxacin Nor Compound 25 Caused ds DNA Damage on Drug-Resistant ATCC BAA-1797

*A. baumannii* ATCC 15151 and ATCC BAA-1797 were grown from a glycerol stock by placing a small volume of cells onto a MHA plate. The MHA plate was incubated overnight at 37° C. A single colony was subsequently used to inoculate MHB to obtain a bacterial broth suspension. The MHB broth suspension was grown at 37° C. on a rotary shaking incubator (100 rpm) for 12 hours. The bacterial cell concentration was adjusted to ~1×10$^8$ CFU/mL in MHB using OD at 595 nm. 3 mL of cells were spun down and concentrated in 1.5 mL and 2 mL of MHB. 500 μL aliquots of the adjusted bacterial cell suspensions were placed into borosilicate glass tubes, where the cell suspensions were treated with 1.5% hydrogen peroxide ($H_2O_2$), 10 μg/mL ciprofloxacin, or 100 μM Compound 25. The ATCC 1797 cells were treated for 5 hours, and ATCC 15151 cells were treated for 3 hours at 37° C. Cells were spun down and resuspended as a pellet in 185 μL cell suspension buffer. 5 μL of RNase, 10 μL of cell lysis buffer solution, and 5 μL of proteinase K were added. The cells were incubated at 55° C. for 3 hours. The samples were phenol-chloroformed, and 100% ethanol and Na-Acetate were added. The cells were frozen at −20° C. for 2 hours, spun by centrifuge for 1 minute at 10,000 rpm, washed with 70% EtOH, and resuspended in 20 μL water. Sample buffer was added to each of the samples and ran for 1 hour at 100 V on a 0.8% agarose gel.

Figure 31:
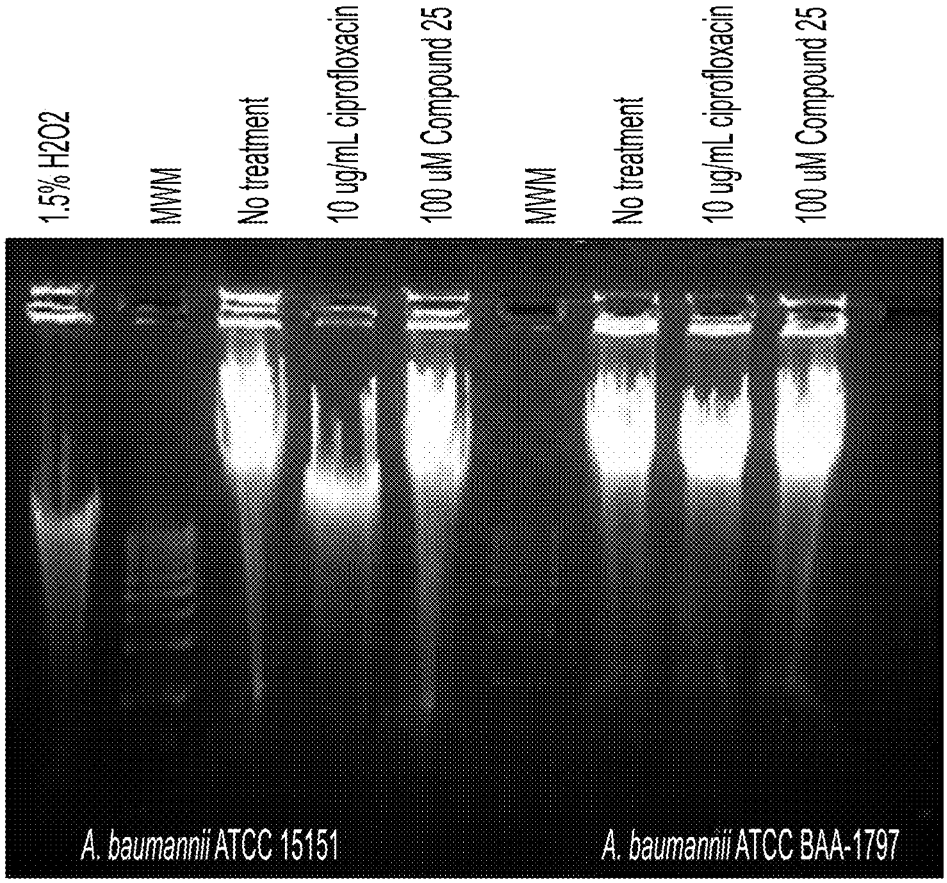
FIG. 31 shows that DNA degradation is caused by $H_2O_2$ and ciprofloxacin but not by Compound 25 in drug-sensitive *A. baumannii* ATCC 15151.

1.5% $H_2O_2$ degraded DNA completely; 10 μg/mL ciprofloxacin also degraded DNA, while Compound 25 did not degrade DNA. FIG. 31 shows that DNA degradation is caused by $H_2O_2$ and ciprofloxacin but not by Compound 25 in drug-sensitive *A. baumannii* ATCC 15151. TABLE 7 summarizes the findings described above.

TABLE 7

| | Comp 14 | Comp 15 | Comp 25 | Comp 26 | Comp 27 |
|---|---|---|---|---|---|
| MIC (μM) | 6 | 12.5 | 6 | 6 | 12.5 |
| Synergize with PME? | Yes, at 4 μM | — | Yes, at 1 μM | Yes, at 1 μM | Yes, at 6 μM |
| MIC in 10% FBS (μM) | >100 | >100 | >100 | >100 | >100 |
| IC50 on HeLa in 10% FBS (μM) | 36.7 ± 3.8 | 20.9 ± 1.5 | 30.4 ± 3.3 | 37.3 ± 1.8 | 25.8 ± 5.2 |
| MIC in 40% FBS (μM) | 50 | >100 | 50 | 100 | 50 |
| IC50 on HeLa in 40% FBS (μM) | 183.4 | 67.4 | 100.9 | 58.2 | 69.7 |
| Membrane permeabilizer with PI | No | No | No | No | No |
| Membrane permeabilizer with LDS-751 | Yes | Yes | Yes | Yes | Yes |
| RecA attenuation with norflox on *E. coli* | Yes | Yes | Yes | Yes | Yes |
| Kill at 4X MIC at 16 hours | 5-logs | 6-logs | 5-logs | 5-logs | 5-logs |
| Evolution of resistance? | Yes; >6-fold | Yes; >4-fold | No | Yes; 2-fold | Yes; 4-fold |

Example 26: Direct Comparison of Compound 26 in 5% FBS on *H. pylori* Hp A-4 and *A. baumannii* BAA-1797

Figure 32A:
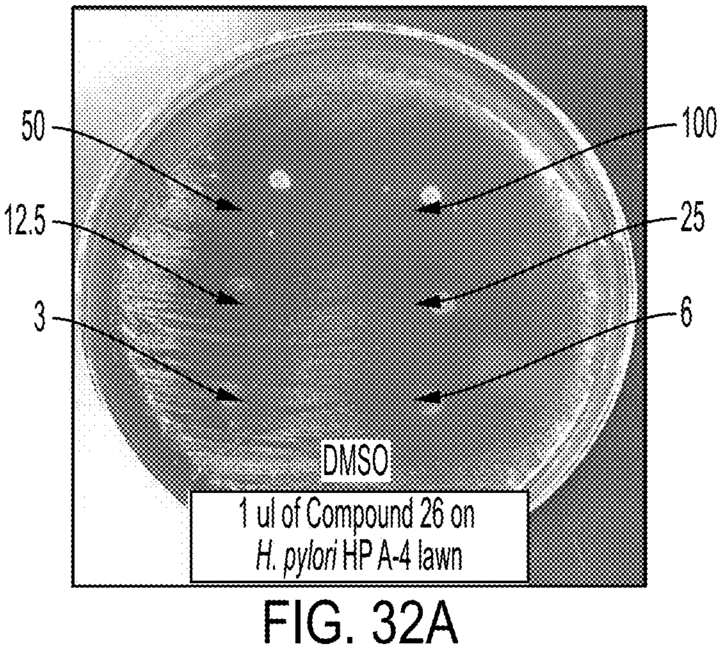
FIG. 32A shows a blood agar plate with a lawn of *H. pylori* used to test the efficacy of Compound 26.
Figure 32B:
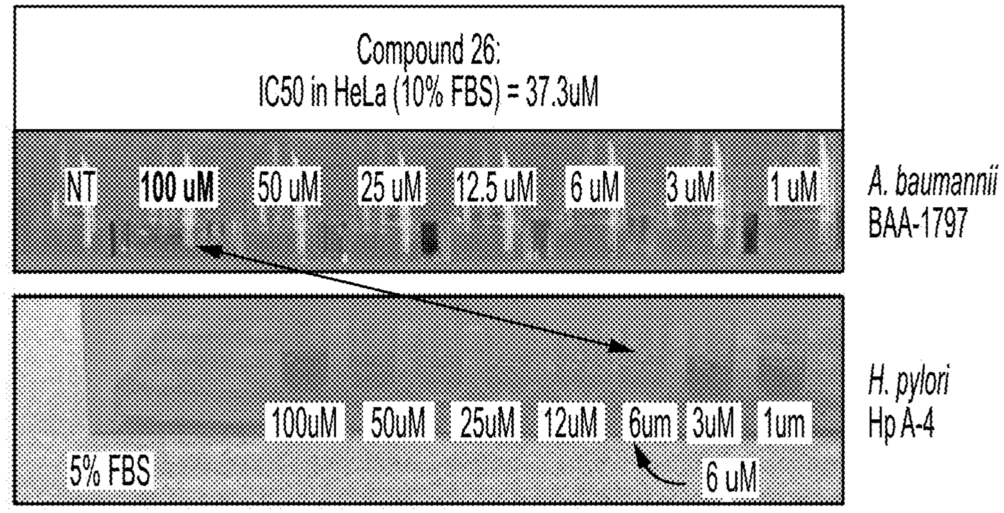
FIG. 32B shows images of a liquid culture samples with *A. baumannii* and *H. pylori* used to determine the efficacy of Compound 26.

A direct comparison of Compound 26 in 5% FBA on *H. pylori* Hp A-4 and *A. baumannii* BAA-1797 was performed. The conditions were standard liquid culture conditions for each organism in 5% FBS. A lawn of *H. pylori* Hp A-4 on a blood agar plate was prepared. 1 μL of Compound 26 at various concentrations and 1 μL of 100% sterile DMSO were spotted on the blood agar plate. The plate was incubated for 4 days at 37° C. in 5% $CO_2$. A 16.6-fold increase in anti-bacterial activity was observed for *H. pylori* compared to *A. baumanii* in 5% FBS. FIG. 32A shows a blood agar plate with a lawn of *H. pylori* used to test the efficacy of Compound 26. FIG. 32B shows images of a liquid culture samples with *A. baumannii* and *H. pylori* used to determine the efficacy of Compound 26.

Embodiments

The following non-limiting embodiments provide illustrative examples of the invention, but do not limit the scope of the invention.

Embodiment 1. A compound of formula:

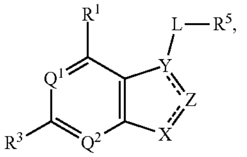

wherein:

- one ═══ is a single bond and the other ═══ is a double bond;
- X is O, S, N, NH, or N($R^N$);
- $R^N$ is alkyl, alkylene, acyl, or alkoxycarbonyl, any of which is substituted or unsubstituted;
- Z is CH, C(alkyl that is substituted or unsubstituted), C(aryl that is substituted or unsubstituted), C(heteroaryl that is substituted or unsubstituted), or N;
- Y is C or N, wherein when Y is N, the ═══ connecting Y and Z is the single bond, and X is N, and wherein when Y is C, the ═══ connecting Y and Z is the double bond, and X is O, S, NH, or N($R^N$);
- L is —CH═N—NH—, —N═N—, or —CH═N—$NHSO_2$—;
- $Q^1$ is N or $CR^2$;
- $Q^2$ is N or $CR^4$;
- $R^1$ is OH, $OR^{1a}$, SH, $SR^{1a}$, $NH_2$, $NHR^{1a}$, $N(R^{1a})_2$, $N(R^{1a})_3$, $OC(O)NH_2$, $OC(O)NHR^{1a}$, $OC(O)N(R^{1a})_2$, $NHC(NH)NH_2$, $NHC(NH)NHR^{1a}$, $NHC(NH)N(R^{1a})_2$, $NHC(O)NH_2$, $NHC(O)NHR^{1a}$, $NHC(O)N(R^{1a})_2$, or H;
- each $R^{1a}$ is independently $C(O)R^{1b}$, alkyl, alkenyl, alkynyl, aryl, cycloalkyl, heterocyclyl, heteroaryl, or an amino acid residue, any of which is substituted or unsubstituted;
- $R^{1b}$ is alkyl, alkenyl, alkynyl, aryl, cycloalkyl, heterocyclyl, or heteroaryl, any of which is substituted or unsubstituted;
- $R^2$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;
- $R^3$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;
- $R^4$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;
- $R^5$ is aryl, cycloalkyl, heterocyclyl, heteroaryl, or $C(O)R^6$, any of which is substituted or unsubstituted; and
- $R^6$ is alkyl, alkenyl, alkynyl, aryl, cycloalkyl, heterocyclyl, or heteroaryl, any of which is substituted or unsubstituted, or a pharmaceutically-acceptable salt thereof.

Embodiment 2. The compound of embodiment 1, wherein $R^2$ is H.

Embodiment 3. The compound of embodiment 1 or 2, wherein the compound is of formula:

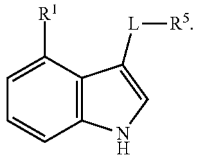

Embodiment 4. The compound of any one of embodiments 1-3, wherein L is —CH═N—NH—.

Embodiment 5. The compound of any one of embodiments 1-4, wherein $R^1$ is OH, $OR^{1a}$, $NH_2$, $NHR^{1a}$, or $N(R^{1a})_2$.

Embodiment 6. The compound of any one of embodiments 1-5, wherein $R^1$ is OH, $NH_2$, $NMe_3$; NH(1H-benzotriazol-1-yl; $NHC(O)CH(NH_2)CH_2C(O)NH_2$, $NHC(O)CH(NH_2)(CH_2)_3NHC(NH)NH_2$, $OC(O)(CH_2)_3Me$, $OC(O)CH(NH_2)(CH_2)_3NHC(NH)NH_2$, $OC(O)CH(NHC(O)OCMe_3)(CH_2)_3NHC(NH)NH_2$, $NHC(O)OCMe_3$, O-benzyl, $OC(O)(CH_2)_3NH_2$, $O(CH_2)_4NMe_3$, 2-(4-methylpipyrazin-1-yl)-ethoxy, 2-(1-methylpipyradin-4-yl)-ethoxy, or 2-(1,1-dimethylpipyradin-4-yl)-ethoxy.

Embodiment 7. The compound of any one of embodiments 1-5, wherein $R^1$ is $OR^{1a}$, and $R^{1a}$ is alkyl that is substituted.

Embodiment 8. The compound of any one of embodiments 1-5 or 7, wherein $R^1$ is $OR^{1a}$, and $R^{1a}$ is alkyl that is substituted with aryl, heteroaryl, or amino.

Embodiment 9. The compound of any one of embodiments 1-5, wherein $R^1$ is O-benzyl.

Embodiment 10. The compound of any one of embodiments 1-9, wherein $R^5$ is phenyl, substituted phenyl, C(O)(substituted alkyl), pyrimidinyl, substituted naphthalene, tetrahydropyrimidine, substituted methyl, substituted quinoline, or C(O)phenyl.

Embodiment 11. The compound of any one of embodiments 1-10, wherein $R^5$ is 4-substituted phenyl, 2,4-disubstituted phenyl, C(O)(substituted methyl), 2-pyrimidinyl, 5-substituted naphthalene, 2-tetrahydropyrimidine, trisubstituted methyl, 7-substituted quinoline-4-yl, or C(O)phenyl.

Embodiment 12. The compound of any one of embodiments 1-10, wherein $R^5$ is bromophenyl, chlorophenyl, dichlorophenyl, fluorophenyl, nitrophenyl, benzoic acid, C(O)(cyanoalkyl), 2-pyrimidinyl, benzonitrile, anisole, aminonaphthalene, 3,4,5,6-tetrahydropyrimidine, fluoromethyl, aniline, bromoquinoline, or —C(O)phenyl.

Embodiment 13. The compound of any one of embodiments 1-12, wherein $R^5$ is 4-bromophenyl, 2-chlorophenyl, 4-chlorophenyl, 4-fluorophenyl, 4-nitrophenyl, 4-benzoic acid, C(O)(cyanomethyl), 2-pyrimidinyl, 4-benzonitrile, 4-anisole, 2,4-dichlorophenyl, 5-aminonaphthalene, 2-(3,4,5,6-tetrahydropyrimidine), trifluoromethyl, 4-aniline, 7-bromoquinolin-4-yl, or C(O)phenyl.

Embodiment 14. The compound of any one of embodiments 1-13, wherein $R^5$ is substituted aryl.

Embodiment 15. The compound of any one of embodiments 1-14, wherein $R^5$ is substituted phenyl.

Embodiment 16. The compound of any one of embodiments 1-15, wherein $R^5$ is 4-substituted phenyl.

Embodiment 17. The compound of any one of embodiments 1-16, wherein $R^5$ is 4-bromophenyl.

Embodiment 18. The compound of any one of embodiments 1-16, wherein $R^5$ is 4-chlorophenyl.

Embodiment 19. The compound of embodiment 1, wherein the compound is:

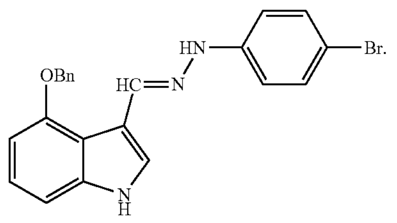 [SMILES: Brc1ccc(N/N=C/c2c[nH]c3cccc(OCc4ccccc4)c23)cc1]

Embodiment 20. The compound of embodiment 1, wherein the compound is:

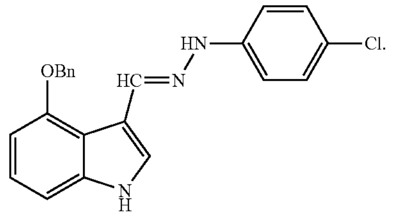 [SMILES: Clc1ccc(N/N=C/c2c[nH]c3cccc(OCc4ccccc4)c23)cc1]

Embodiment 21. A method of treating a condition, the method comprising administering to a subject in need thereof a therapeutically-effective amount of a compound of formula:

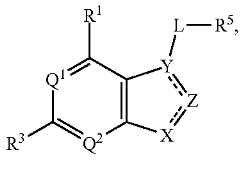

wherein:

- one ------ is a single bond and the other ------ is a double bond;
- X is O, S, N, NH, or $N(R^N)$;
- $R^N$ is alkyl, alkylene, acyl, or alkoxycarbonyl, any of which is substituted or unsubstituted;
- Z is CH, C(alkyl that is substituted or unsubstituted), C(aryl that is substituted or unsubstituted), C(heteroaryl that is substituted or unsubstituted), or N;
- Y is C or N, wherein when Y is N, the ------ connecting Y and Z is the single bond, and X is N, and wherein when Y is C, the ------ connecting Y and Z is the double bond, and X is O, S, NH, or $N(R^N)$;
- L is a linker group;
- $Q^1$ is N or $CR^2$;
- $Q^2$ is N or $CR^4$;
- $R^1$ is OH, $OR^{1a}$, SH, $SR^{1a}$, $NH_2$, $NHR^{1a}$, $N(R^{1a})_2$, $N(R^{1a})_3$, $OC(O)NH_2$, $OC(O)NHR^{1a}$, $OC(O)N(R^{1a})_2$, $NHC(NH)NH_2$, $NHC(NH)NHR^{1a}$, $NHC(NH)N(R^{1a})_2$, $NHC(O)NH_2$, $NHC(O)NHR^{1a}$, $NHC(O)N(R^{1a})_2$, or H;
- each $R^{1a}$ is independently $C(O)R^{1b}$, alkyl, alkenyl, alkynyl, aryl, cycloalkyl, heterocyclyl, heteroaryl, or an amino acid residue, any of which is substituted or unsubstituted;
- $R^{1b}$ is alkyl, alkenyl, alkynyl, aryl, cycloalkyl, heterocyclyl, or heteroaryl, any of which is substituted or unsubstituted;
- $R^2$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;
- $R^3$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;
- $R^4$ is OH, O(alkyl), SH, S(alkyl), CN, $NH_2$, NH(alkyl), N(alkyl)(alkyl), alkyl, F, Cl, Br, I, $NO_2$, formyl, acetyl, propionyl, or H;
- $R^5$ is aryl, cycloalkyl, heterocyclyl, heteroaryl, or $C(O)R^6$, any of which is substituted or unsubstituted; and
- $R^6$ is alkyl, alkenyl, alkynyl, aryl, cycloalkyl, heterocyclyl, or heteroaryl, any of which is substituted or unsubstituted, or a pharmaceutically-acceptable salt thereof.

Embodiment 22. The method of embodiment 21, wherein the compound is of formula:

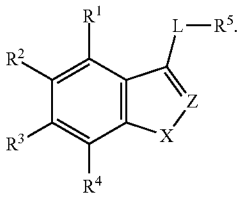

Embodiment 23. The method of embodiment 21 or 22, wherein Z is CH.

Embodiment 24. The method of any one of embodiments 21-23, wherein $R^3$ is H.

Embodiment 25. The method of any one of embodiments 21-24, wherein $R^4$ is H.

Embodiment 26. The method of any one of embodiments 21-25, wherein the compound is of formula:

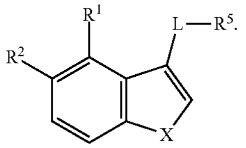

Embodiment 27. The method of any one of embodiments 21-26, wherein X is NH, NMe, NC(O)Me, or N-(2-(N,N-dimethylamino)eth-1-yl).

Embodiment 28. The method of any one of embodiments 21-27, wherein X is NH.

Embodiment 29. The method of any one of embodiments 21-28, wherein the compound is of formula:

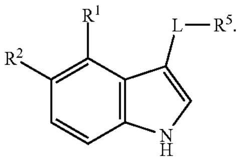

Embodiment 30. The method of any one of embodiments 21-29, wherein $R^2$ is $NH_2$, F, Cl, Br, I, $NO_2$, or H.

Embodiment 31. The method of any one of embodiments 21-30, wherein $R^2$ is H.

Embodiment 32. The method of any one of embodiments 21-31, wherein the compound is of formula:

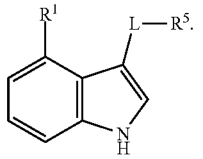

Embodiment 33. The method of any one of embodiments 21-32, wherein $R^1$ is OH, $OR^{1a}$, $NH_2$, $NHR^{1a}$, or $N(R^{1a})_2$.

Embodiment 34. The method of any one of embodiments 21-33, wherein $R^1$ is OH, $NH_2$, $NMe_3$; NH(1H-benzotriazol-1-yl; $NHC(O)CH(NH_2)CH_2C(O)NH_2$, $NHC(O)CH(NH_2)(CH_2)_3NHC(NH)NH_2$, $OC(O)(CH_2)_3Me$, $OC(O)CH(NH_2)(CH_2)_3NHC(NH)NH_2$, $OC(O)CH(NHC(O)OCMe_3)(CH_2)_3NHC(NH)NH_2$, $NHC(O)OCMe_3$, O-benzyl, $OC(O)(CH_2)_3NH_2$, $O(CH_2)_4NMe_3$, 2-(4-methylpipyrazin-1-yl)-ethoxy, 2-(1-methylpipyradin-4-yl)-ethoxy, or 2-(1,1-dimethylpipyradin-4-yl)-ethoxy.

Embodiment 35. The method of any one of embodiments 21-33, wherein $R^1$ is $OR^{1a}$, and $R^{1a}$ is alkyl that is substituted.

Embodiment 36. The method of any one of embodiments 21-33 or 35, wherein $R^1$ is $OR^{1a}$, and $R^{1a}$ is alkyl that is substituted with aryl, heteroaryl, or amino.

Embodiment 37. The method of any one of embodiments 21-33, 35, or 36, wherein R, is O-benzyl.

Embodiment 38. The method of any one of embodiments 21-37, wherein $R^5$ is phenyl, substituted phenyl, C(O)(substituted alkyl), pyrimidinyl, substituted naphthalene, tetrahydropyrimidine, substituted methyl, substituted quinoline, or C(O)phenyl.

Embodiment 39. The method of any one of embodiments 21-38, wherein $R^5$ is 4-substituted phenyl, 2,4-disubstituted phenyl, C(O)(substituted methyl), 2-pyrimidinyl, 5-substituted naphthalene, 2-tetrahydropyrimidine, trisubstituted methyl, 7-substituted quinoline-4-yl, or C(O)phenyl.

Embodiment 40. The method of any one of embodiments 21-39, wherein $R^5$ is bromophenyl, chlorophenyl, dichlorophenyl, fluorophenyl, nitrophenyl, benzoic acid, C(O)(cyanoalkyl), 2-pyrimidinyl, benzonitrile, anisole, aminonaphthalene, 3,4,5,6-tetrahydropyrimidine, fluoromethyl, aniline, bromoquinoline, or C(O)phenyl.

Embodiment 41. The method of any one of embodiments 21-40, wherein $R^5$ is 4-bromophenyl, 2-chlorophenyl, 4-chlorophenyl, 4-fluorophenyl, 4-nitrophenyl, 4-benzoic acid, C(O)(cyanomethyl), 2-pyrimidinyl, 4-benzonitrile, 4-anisole, 2,4-dichlorophenyl, 5-aminonaphthalene, 2-(3,4,5,6-tetrahydropyrimidine), trifluoromethyl, 4-aniline, 7-bromoquinolin-4-yl, or C(O)phenyl.

Embodiment 42. The method of any one of embodiments 21-41, wherein $R^5$ is substituted aryl.

Embodiment 43. The method of any one of embodiments 21-42, wherein $R^5$ is substituted phenyl.

Embodiment 44. The method of any one of embodiments 21-43, wherein $R^5$ is 4-substituted phenyl.

Embodiment 45. The method of any one of embodiments 21-44, wherein $R^5$ is 4-bromophenyl.

Embodiment 46. The method of any one of embodiments 21-44, wherein $R^5$ is 4-chlorophenyl.

Embodiment 47. The method of any one of embodiments 21-46, wherein the linker group is —CH═N—NH—, —N═N—, —CH═N—$NHSO_2$—, or —O—.

Embodiment 48. The method of any one of embodiments 21-47, wherein the linker group is —CH═N—NH—.

Embodiment 49. The method of embodiment 21, wherein the compound is:

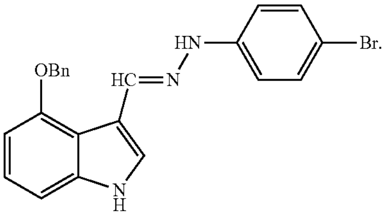 [SMILES: Brc1ccc(N/N=C/c2c[nH]c3cccc(OCc4ccccc4)c23)cc1]

Embodiment 50. The method of embodiment 21, wherein the compound is:

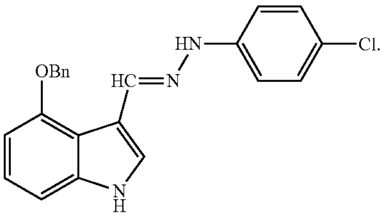 [SMILES: Clc1ccc(N/N=C/c2c[nH]c3cccc(OCc4ccccc4)c23)cc1]

Embodiment 51. The method of any one of embodiments 21-50, wherein the condition is caused by a microbe.

Embodiment 52. The method of embodiment 51, wherein the microbe is a bacterium.

Embodiment 53. The method of embodiment 51, wherein the microbe is a gram-positive bacterium.

Embodiment 54. The method of embodiment 51, wherein the microbe is a gram-negative bacterium.

Embodiment 55. The method of embodiment 51, wherein the microbe is a drug-resistant or drug-sensitive bacterium.

Embodiment 56. The method of embodiment 51, wherein the microbe is methicillin-resistant *Staphylococcus aureus.*

Embodiment 57. The method of embodiment 51, wherein the microbe is *Acinetobacter baumannii.*

Embodiment 58. The method of embodiment 57, wherein the microbe is Carbapenem Resistant *Acinetobacter baumannii.*

Embodiment 59. The method of embodiment 51, wherein the microbe is *Escherichia coli.*

Embodiment 60. The method of embodiment 51, wherein the microbe is *Helicobacter pylori.*

Embodiment 61. The method of embodiment 51, wherein the microbe is *Campylobacter jejuni.*

Embodiment 62. The method of any one of embodiments 51-61, wherein the compound lessens an activity of a drug resistance mechanism in the microbe.

Embodiment 63. The method of any one of embodiments 21-62, wherein the administering is oral.

Embodiment 64. The method of any one of embodiments 21-62, wherein the administering is topical.

Embodiment 65. The method of any one of embodiments 21-62, wherein the administering is intravenous.

Embodiment 66. The method of any one of embodiments 21-62, wherein the administering is subcutaneous.

Embodiment 67. The method of any one of embodiments 21-62, wherein the administering is ocular.

Embodiment 68. The method of any one of embodiments 21-62, wherein the administering is by inhalation.

Embodiment 69. The method of any one of embodiments 21-68, wherein the subject is human.

Embodiment 70. The method of any one of embodiments 21-69, wherein the therapeutically-effective amount is from about 5 mg/kg to about 50 mg/kg.

Embodiment 71. The method of any one of embodiments 21-70, further comprising administering a therapeutic agent to the subject.

Embodiment 72. The method of embodiment 71, wherein the therapeutic agent is an antibiotic.

Embodiment 73. The method of embodiment 71, wherein the therapeutic agent is polymyxin B or a pharmaceutically-acceptable salt thereof.

Embodiment 74. The method of embodiment 71, wherein the therapeutic agent is kanamycin or a pharmaceutically-acceptable salt thereof.

Embodiment 75. The method of embodiment 71, wherein the therapeutic agent is gentamicin or a pharmaceutically-acceptable salt thereof.

Embodiment 76. The method of any one of embodiments 71-73, wherein the compound and the therapeutic agent is administered in a common unit dosage form.

Embodiment 77. The method of any one of embodiments 21-76, wherein the compound blocks a RecA pathway.

Embodiment 78. The method of any one of embodiments 21-77, wherein the compound blocks a MazEF pathway.

Embodiment 79. The method of any one of embodiments 21-78, wherein the compound triggers programmed cell death.

Embodiment 80. The method of any one of embodiments 21-79, wherein the compound triggers error prone DNA polymerase repair.

Embodiment 81. The method of any one of embodiments 21-80, wherein the condition is an infection of the gastro-intestinal tract.

Embodiment 82. The method of any one of embodiments 21-80, wherein the condition is a peptic ulcer, gastroenteritis, urinary tract infection, or a lower respiratory tract infection.

Embodiment 83. The method of any one of embodiments 21-80, wherein the condition is an infection associated with a burn, laceration, abrasion, bite, surgical wound, puncture wound, ulcer, complicated skin and soft tissue infection (cSSTI), skin and skin structure infection (SSSI), venous stasis ulcer, diabetic ulcer, pressure ulcer, post-surgical ulcer, post traumatic ulcer, or spontaneous ulcer.

What is claimed is:

1. A compound of formula:

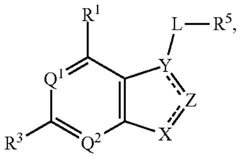

wherein:

one ===== is a single bond and the other ===== is a double bond;

X is NH or $N(R^N)$;

$R^N$ is alkyl, acyl, or alkoxycarbonyl, any of which is substituted or unsubstituted;

Z is CH, C(alkyl that is substituted or unsubstituted), C(aryl that is substituted or unsubstituted), C(heteroaryl that is substituted or unsubstituted), or N;

Y is C, wherein the ===== connecting Y and Z is the double bond;

L is —CH═N—NH—;

$Q^1$ is CH;

$Q^2$ is CH;

$R^1$ is OH, $OR^{1a}$, $OC(O)NH_2$, $OC(O)NHR^{1a}$, or $OC(O)N(R^{1a})_2$;

each $R^{1a}$ is independently $C(O)R^{1b}$, alkyl, alkenyl, alkynyl, aryl, cycloalkyl, heterocyclyl, heteroaryl, or an amino acid residue, any of which is substituted or unsubstituted;

$R^{1b}$ is alkyl, alkenyl, alkynyl, aryl, cycloalkyl, heterocyclyl, or heteroaryl, any of which is substituted or unsubstituted;

$R^3$ is H;

$R^5$ is aryl, cycloalkyl, heterocyclyl, heteroaryl, or $C(O)R^6$, wherein the aryl, cycloalkyl, heterocyclyl, or heteroaryl is substituted with halo, halo-alkyl, amino, cyano, or carboxyl; and $R^6$ is alkyl, alkenyl, alkynyl, aryl, cycloalkyl, heterocyclyl, or heteroaryl, any of which is substituted or unsubstituted, or a pharmaceutically-acceptable salt thereof.

2. The compound of claim 1, wherein $R^f$ is OH or $OR^{1a}$.

3. The compound of claim 1, wherein $R^f$ is OH, $OC(O)CH(NH_2)(CH_2)_3NHC(NH)NH_2$, $OC(O)CH(NHC(O)OCMe_3)(CH_2)_3NHC(NH)NH_2$, O-benzyl, or $OC(O)(CH_2)_3NH_2$.

4. The compound of claim 1, wherein $R^1$ is $OR^{1a}$, and $R^{1a}$ is alkyl that is substituted with aryl, heteroaryl, or amino.

5. The compound of claim 1, wherein $R^f$ is O-benzyl.

6. The compound of claim 1, wherein $R^5$ is 4-substituted phenyl, 2,4-disubstituted phenyl, C(O)(substituted methyl), 2-pyrimidinyl, 5-substituted naphthalene, 2-tetrahydropyrimidine, 7-substituted quinoline-4-yl, or C(O)phenyl.

7. The compound of claim 1, wherein $R^5$ is bromophenyl, chlorophenyl, dichlorophenyl, or fluorophenyl.

8. The compound of claim 1, wherein $R^5$ is 4-bromophenyl, 2-chlorophenyl, 4-chlorophenyl, 4-fluorophenyl, 4-benzoic acid, C(O)(cyanomethyl), 4-benzonitrile, 2,4-dichlorophenyl, 5-aminonaphthalene, 4-aniline, or 7-bromoquinolin-4-yl.

9. The compound of claim 1, wherein $R^5$ is substituted phenyl.

10. The compound of claim 1, wherein $R^5$ is 4-substituted phenyl.

11. The compound of claim 1, wherein $R^5$ is 4-bromophenyl.

12. The compound of claim 1, wherein $R^5$ is 4-chlorophenyl.

13. The compound of claim 1, wherein the compound is:
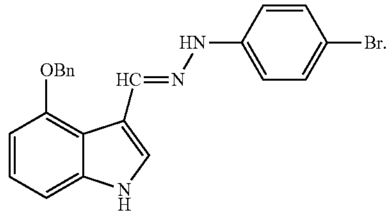 [SMILES: Brc1ccc(N/N=C/c2c[nH]c3cccc(OCc4ccccc4)c23)cc1]
14. The compound of claim 1, wherein the compound is:
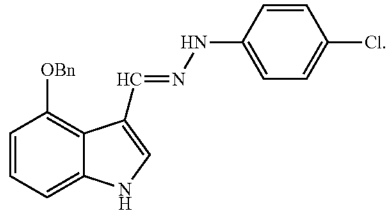 [SMILES: Clc1ccc(N/N=C/c2c[nH]c3cccc(OCc4ccccc4)c23)cc1]
15. The compound of claim 1, wherein $R^1$ is —$OR^{1a}$.
16. The compound of claim 15, wherein $R^{1a}$ is alkyl substituted with aryl.
17. The compound of claim 15, wherein $R^{1a}$ is aryl.
18. The compound of claim 15, wherein, X is NH, $R^{1a}$ is alkyl substituted with aryl, and $R^5$ is 4-substituted phenyl.
* * * * *